United States Patent
Gharib

(10) Patent No.: US 9,392,953 B1
(45) Date of Patent: Jul. 19, 2016

(54) NEUROPHYSIOLOGIC MONITORING

(75) Inventor: James Gharib, San Diego, CA (US)

(73) Assignee: NuVasive, Inc., San Diego, CA (US)

(*) Notice: Subject to any disclaimer, the term of this patent is extended or adjusted under 35 U.S.C. 154(b) by 0 days.

(21) Appl. No.: 13/236,600

(22) Filed: Sep. 19, 2011

Related U.S. Application Data

(60) Provisional application No. 61/384,186, filed on Sep. 17, 2010.

(51) Int. Cl.
*A61B 5/0488* (2006.01)
*A61B 5/04* (2006.01)
*A61B 5/00* (2006.01)
*A61B 18/00* (2006.01)

(52) U.S. Cl.
CPC ............ *A61B 5/0488* (2013.01); *A61B 5/4836* (2013.01); *A61B 2018/00642* (2013.01)

(58) Field of Classification Search
CPC .... A61B 5/4893; A61B 5/489; A61B 5/0488; A61B 2017/0262; A61B 5/04001
USPC ..................................... 600/554, 546; 607/48
See application file for complete search history.

(56) References Cited

U.S. PATENT DOCUMENTS

| | | |
|---|---|---|
| 208,227 A | 9/1878 | Dorr |
| 972,983 A | 10/1910 | Arthur |
| 1,328,624 A | 1/1920 | Graham |
| 1,548,184 A | 8/1925 | Cameron |
| 2,704,064 A | 3/1955 | Fizzell et al. |
| 2,736,002 A | 2/1956 | Oriel |
| 2,808,826 A | 10/1957 | Reiner et al. |
| 3,364,929 A | 1/1968 | Ide et al. |
| 3,664,329 A | 5/1972 | Naylor |
| 3,682,162 A | 8/1972 | Colyer |
| 3,785,368 A | 1/1974 | McCarthy et al. |
| 3,830,226 A | 8/1974 | Staub |
| 3,851,641 A | 12/1974 | Toole et al. |
| 3,957,036 A | 5/1976 | Normann |
| 4,099,519 A | 7/1978 | Warren |
| 4,164,214 A | 8/1979 | Stark et al. |
| 4,207,897 A | 6/1980 | Lloyd et al. |
| 4,224,949 A | 9/1980 | Scott et al. |
| 4,226,228 A | 10/1980 | Shin et al. |
| 4,235,242 A | 11/1980 | Howson et al. |
| 4,252,130 A | 2/1981 | Le Pivert |
| 4,285,347 A | 8/1981 | Hess |
| 4,291,705 A | 9/1981 | Severinghaus et al. |
| 4,461,300 A | 7/1984 | Christensen |
| 4,515,168 A | 5/1985 | Chester et al. |
| 4,519,403 A | 5/1985 | Dickhudt |
| 4,545,374 A | 10/1985 | Jacobson |
| 4,561,445 A | 12/1985 | Berke et al. |
| 4,562,832 A | 1/1986 | Wilder et al. |

(Continued)

OTHER PUBLICATIONS

"Electromyography System," International Search Report from International Application No. PCT/US00/32329, Apr. 27, 2001, 4 pages.

(Continued)

*Primary Examiner* — Sean Dougherty
(74) *Attorney, Agent, or Firm* — Heather Prado

(57) ABSTRACT

The present invention relates generally to a system and methods used for neurophysiologic monitoring, and more particularly to an algorithm capable of discerning between background activity (non-physiologic and physiologic) and evoked neurophysiologic activity.

8 Claims, 34 Drawing Sheets

(56) References Cited

U.S. PATENT DOCUMENTS

| | | | |
|---|---|---|---|
| 4,573,448 A | 3/1986 | Kambin | |
| 4,592,369 A | 6/1986 | Davis et al. | |
| 4,595,018 A | 6/1986 | Rantala | |
| 4,633,889 A | 1/1987 | Talalla et al. | |
| 4,658,835 A | 4/1987 | Pohndorf | |
| 4,744,371 A | 5/1988 | Harris | |
| 4,759,377 A | 7/1988 | Dykstra | |
| 4,784,150 A | 11/1988 | Voorhies et al. | |
| 4,807,642 A | 2/1989 | Brown | |
| 4,892,105 A | 1/1990 | Prass | |
| 4,926,865 A | 5/1990 | Oman | |
| 4,962,766 A | 10/1990 | Herzon | |
| 4,964,411 A | 10/1990 | Johnson et al. | |
| 5,007,902 A | 4/1991 | Witt | |
| 5,058,602 A | 10/1991 | Brody | |
| 5,081,990 A | 1/1992 | Deletis | |
| 5,092,344 A | 3/1992 | Lee | |
| 5,127,403 A | 7/1992 | Brownlee | |
| 5,161,533 A | 11/1992 | Prass et al. | |
| 5,196,015 A | 3/1993 | Neubardt | |
| 5,220,920 A * | 6/1993 | Gharib | 600/345 |
| 5,236,416 A * | 8/1993 | McDaniel et al. | 604/67 |
| RE34,390 E | 9/1993 | Culver | |
| 5,255,691 A | 10/1993 | Otten | |
| 5,282,468 A | 2/1994 | Klepinski | |
| 5,284,153 A | 2/1994 | Raymond et al. | |
| 5,284,154 A | 2/1994 | Raymond et al. | |
| 5,299,563 A | 4/1994 | Seton | |
| 5,312,417 A | 5/1994 | Wilk | |
| 5,313,956 A | 5/1994 | Knutsson et al. | |
| 5,327,902 A | 7/1994 | Lemmen | |
| 5,333,618 A | 8/1994 | Lekhtman et al. | |
| 5,375,067 A | 12/1994 | Berchin | |
| 5,383,876 A | 1/1995 | Nardella | |
| 5,450,845 A | 9/1995 | Axelgaard | |
| 5,474,558 A | 12/1995 | Neubardt | |
| 5,480,440 A | 1/1996 | Kambin | |
| 5,482,038 A | 1/1996 | Ruff | |
| 5,484,437 A | 1/1996 | Michelson | |
| 5,540,235 A | 7/1996 | Wilson | |
| 5,549,656 A | 8/1996 | Reiss | |
| 5,560,372 A | 10/1996 | Cory | |
| 5,566,678 A | 10/1996 | Cadwell | |
| 5,579,781 A | 12/1996 | Cooke | |
| 5,593,429 A | 1/1997 | Ruff | |
| 5,599,279 A | 2/1997 | Slotman | |
| 5,601,608 A | 2/1997 | Mouchawar | |
| 5,630,813 A | 5/1997 | Kieturakis | |
| 5,671,752 A | 9/1997 | Sinderby et al. | |
| 5,707,359 A | 1/1998 | Bufalini | |
| 5,711,307 A | 1/1998 | Smits | |
| 5,728,046 A | 3/1998 | Mayer | |
| 5,741,253 A | 4/1998 | Michelson | |
| 5,758,643 A * | 6/1998 | Wong et al. | 600/309 |
| 5,759,159 A | 6/1998 | Masreliez | |
| 5,772,661 A | 6/1998 | Michelson | |
| 5,775,331 A | 7/1998 | Raymond et al. | |
| 5,776,144 A | 7/1998 | Leysieffer et al. | |
| 5,779,642 A | 7/1998 | Nightengale | |
| 5,785,658 A | 7/1998 | Benaron et al. | |
| 5,797,854 A | 8/1998 | Hedgecock | |
| 5,806,522 A | 9/1998 | Katims | |
| 5,807,272 A | 9/1998 | Kun et al. | |
| 5,814,073 A | 9/1998 | Bonutti | |
| 5,830,151 A | 11/1998 | Hadzic et al. | |
| 5,851,191 A | 12/1998 | Gozani et al. | |
| 5,853,373 A | 12/1998 | Griffith et al. | |
| 5,860,973 A | 1/1999 | Michelson | |
| 5,862,314 A | 1/1999 | Jeddeloh | |
| 5,872,314 A | 2/1999 | Clinton | |
| 5,885,219 A | 3/1999 | Nightengale | |
| 5,888,196 A | 3/1999 | Bonutti | |
| 5,902,231 A | 5/1999 | Foley et al. | |
| 5,928,139 A | 7/1999 | Koros et al. | |
| 5,928,158 A | 7/1999 | Aristides | |
| 5,928,159 A | 7/1999 | Eggers et al. | |
| 5,935,131 A | 8/1999 | Bonutti | |
| 5,938,688 A | 8/1999 | Schiff | |
| 5,947,964 A | 9/1999 | Eggers et al. | |
| 5,976,094 A | 11/1999 | Gozani | |
| 6,004,262 A | 12/1999 | Putz et al. | |
| 6,011,985 A | 1/2000 | Athan | |
| 6,026,323 A | 2/2000 | Skladnev et al. | |
| 6,027,456 A | 2/2000 | Feler et al. | |
| 6,038,469 A | 3/2000 | Karlsson et al. | |
| 6,038,477 A | 3/2000 | Kayyali | |
| 6,050,992 A | 4/2000 | Nichols | |
| 6,074,343 A | 6/2000 | Nathanson et al. | |
| 6,104,957 A | 8/2000 | Alo et al. | |
| 6,104,960 A | 8/2000 | Duysens et al. | |
| 6,119,068 A | 9/2000 | Kannonji | |
| 6,120,503 A | 9/2000 | Michelson | |
| 6,128,576 A | 10/2000 | Nishimoto | |
| 6,132,386 A | 10/2000 | Gozani et al. | |
| 6,132,387 A | 10/2000 | Gozani et al. | |
| 6,135,965 A | 10/2000 | Tumer et al. | |
| 6,139,493 A | 10/2000 | Koros et al. | |
| 6,146,335 A | 11/2000 | Gozani | |
| 6,161,047 A | 12/2000 | King et al. | |
| 6,181,961 B1 | 1/2001 | Prass | |
| 6,206,826 B1 | 3/2001 | Mathews et al. | |
| 6,224,549 B1 | 5/2001 | Drongelen | |
| 6,259,945 B1 | 7/2001 | Epstein et al. | |
| 6,266,558 B1 | 7/2001 | Gozani et al. | |
| 6,273,905 B1 | 8/2001 | Streeter | |
| 6,292,701 B1 | 9/2001 | Prass et al. | |
| 6,306,100 B1 | 10/2001 | Prass | |
| 6,312,392 B1 | 11/2001 | Herzon | |
| 6,325,764 B1 | 12/2001 | Griffith et al. | |
| 6,334,068 B1 | 12/2001 | Hacker | |
| 6,337,994 B1 | 1/2002 | Stoianovici et al. | |
| 6,393,325 B1 | 5/2002 | Mann et al. | |
| 6,407,335 B1 * | 6/2002 | Franklin-Lees et al. | 174/58 |
| 6,425,859 B1 | 7/2002 | Foley et al. | |
| 6,425,901 B1 | 7/2002 | Zhu et al. | |
| 6,451,015 B1 | 9/2002 | Rittman et al. | |
| 6,466,817 B1 | 10/2002 | Kaula et al. | |
| 6,500,128 B2 | 12/2002 | Marino | |
| 6,535,759 B1 | 3/2003 | Epstein et al. | |
| 6,564,078 B1 | 5/2003 | Marino et al. | |
| 6,579,244 B2 | 6/2003 | Goodwin | |
| 6,593,528 B2 * | 7/2003 | Franklin-Lees et al. | 174/58 |
| 6,719,692 B2 | 4/2004 | Kleffner et al. | |
| 6,760,616 B2 | 7/2004 | Hoey et al. | |
| 6,796,985 B2 | 9/2004 | Bolger et al. | |
| 6,819,956 B2 | 11/2004 | DiLorenzo | |
| 6,829,508 B2 | 12/2004 | Schulman et al. | |
| 6,849,047 B2 | 2/2005 | Goodwin | |
| 6,855,105 B2 | 2/2005 | Jackson, III | |
| 6,902,569 B2 | 6/2005 | Parmer et al. | |
| 6,926,728 B2 | 8/2005 | Zucherman et al. | |
| 6,929,606 B2 | 8/2005 | Ritland | |
| 7,047,082 B1 | 5/2006 | Schrom et al. | |
| 7,050,848 B2 | 5/2006 | Hoey et al. | |
| 7,079,883 B2 | 7/2006 | Marino et al. | |
| 7,089,059 B1 | 8/2006 | Pless | |
| D533,875 S * | 12/2006 | Miles et al. | D14/495 |
| 7,177,677 B2 | 2/2007 | Kaula et al. | |
| 7,207,949 B2 | 4/2007 | Miles et al. | |
| 7,255,680 B1 * | 8/2007 | Gharib | 604/67 |
| 7,470,236 B1 | 12/2008 | Kelleher et al. | |
| 7,522,953 B2 * | 4/2009 | Kaula et al. | 600/546 |
| 7,582,058 B1 * | 9/2009 | Miles et al. | 600/202 |
| 7,657,308 B2 * | 2/2010 | Miles et al. | 600/546 |
| 7,664,544 B2 * | 2/2010 | Miles et al. | 600/546 |
| 7,691,057 B2 * | 4/2010 | Miles et al. | 600/219 |
| 7,706,843 B2 | 4/2010 | Kaplan | |
| 7,819,801 B2 * | 10/2010 | Miles et al. | 600/224 |
| 7,857,813 B2 | 12/2010 | Schmitz et al. | |
| 7,878,981 B2 | 2/2011 | Strother et al. | |
| 7,887,538 B2 | 2/2011 | Bleich et al. | |
| 7,892,173 B2 * | 2/2011 | Miles et al. | 600/210 |
| 7,896,815 B2 | 3/2011 | Thrope et al. | |
| 7,905,840 B2 | 3/2011 | Pimenta et al. | |

(56) References Cited

U.S. PATENT DOCUMENTS

| | | | |
|---|---|---|---|
| 7,920,922 B2* | 4/2011 | Gharib et al. | 607/48 |
| 7,935,051 B2* | 5/2011 | Miles et al. | 600/202 |
| 7,938,830 B2 | 5/2011 | Saadat et al. | |
| D639,243 S * | 6/2011 | Gharib et al. | D13/133 |
| D639,741 S * | 6/2011 | Gharib et al. | D13/133 |
| 7,963,927 B2 | 6/2011 | Kelleher et al. | |
| 8,000,782 B2* | 8/2011 | Gharib et al. | 600/546 |
| 8,005,535 B2* | 8/2011 | Gharib et al. | 600/546 |
| 8,027,716 B2* | 9/2011 | Gharib et al. | 600/546 |
| 8,050,769 B2* | 11/2011 | Gharib et al. | 607/48 |
| 8,055,349 B2* | 11/2011 | Gharib et al. | 607/48 |
| 8,068,912 B2* | 11/2011 | Kaula et al. | 607/48 |
| 8,114,019 B2* | 2/2012 | Miles et al. | 600/224 |
| 8,133,173 B2* | 3/2012 | Miles et al. | 600/202 |
| 8,137,284 B2* | 3/2012 | Miles et al. | 600/554 |
| 8,147,421 B2* | 4/2012 | Farquhar et al. | 600/554 |
| 8,172,750 B2* | 5/2012 | Miles et al. | 600/202 |
| 8,182,423 B2* | 5/2012 | Miles et al. | 600/214 |
| 8,187,179 B2* | 5/2012 | Miles et al. | 600/210 |
| 8,192,356 B2* | 6/2012 | Miles et al. | 600/202 |
| 8,192,357 B2* | 6/2012 | Miles et al. | 600/202 |
| 8,244,343 B2* | 8/2012 | Gharib et al. | 600/546 |
| 8,255,044 B2* | 8/2012 | Miles et al. | 600/546 |
| 8,255,045 B2* | 8/2012 | Gharib et al. | 600/547 |
| 8,265,744 B2* | 9/2012 | Gharib et al. | 600/546 |
| 8,303,498 B2* | 11/2012 | Miles et al. | 600/224 |
| 2001/0039949 A1 | 11/2001 | Loubser | |
| 2001/0056280 A1 | 12/2001 | Underwood et al. | |
| 2002/0007129 A1 | 1/2002 | Marino | |
| 2002/0072686 A1 | 6/2002 | Hoey et al. | |
| 2002/0123780 A1 | 9/2002 | Grill et al. | |
| 2002/0134570 A1* | 9/2002 | Franklin-Lees et al. | 174/58 |
| 2002/0161415 A1 | 10/2002 | Cohen et al. | |
| 2002/0193843 A1 | 12/2002 | Hill | |
| 2003/0032966 A1 | 2/2003 | Foley et al. | |
| 2003/0105503 A1 | 6/2003 | Marino | |
| 2004/0199084 A1 | 10/2004 | Kelleher et al. | |
| 2004/0203490 A1 | 10/2004 | Kaplan | |
| 2004/0225228 A1 | 11/2004 | Ferree | |
| 2005/0004593 A1 | 1/2005 | Simonson | |
| 2005/0004623 A1* | 1/2005 | Miles et al. | 607/48 |
| 2005/0033380 A1 | 2/2005 | Tanner et al. | |
| 2005/0075578 A1* | 4/2005 | Gharib et al. | 600/546 |
| 2005/0149035 A1 | 7/2005 | Pimenta et al. | |
| 2005/0182454 A1* | 8/2005 | Gharib et al. | 607/48 |
| 2005/0192575 A1 | 9/2005 | Pacheco | |
| 2006/0025703 A1* | 2/2006 | Miles et al. | 600/554 |
| 2006/0052828 A1 | 3/2006 | Kim et al. | |
| 2006/0069315 A1 | 3/2006 | Miles et al. | |
| 2006/0224078 A1 | 10/2006 | Hoey et al. | |
| 2007/0016097 A1* | 1/2007 | Farquhar et al. | 600/546 |
| 2007/0021682 A1* | 1/2007 | Gharib et al. | 600/546 |
| 2007/0198062 A1 | 8/2007 | Miles et al. | |
| 2007/0293782 A1 | 12/2007 | Marino | |
| 2008/0058606 A1* | 3/2008 | Miles et al. | 600/214 |
| 2008/0064976 A1 | 3/2008 | Kelleher et al. | |
| 2008/0064977 A1 | 3/2008 | Kelleher et al. | |
| 2008/0065178 A1 | 3/2008 | Kelleher et al. | |
| 2008/0071191 A1 | 3/2008 | Kelleher et al. | |
| 2008/0097164 A1* | 4/2008 | Miles et al. | 600/219 |
| 2008/0167574 A1 | 7/2008 | Farquhar et al. | |
| 2008/0221473 A1* | 9/2008 | Calancie et al. | 600/546 |
| 2009/0018399 A1 | 1/2009 | Martinelli | |
| 2009/0018610 A1* | 1/2009 | Gharib et al. | 607/48 |
| 2009/0054804 A1* | 2/2009 | Gharib et al. | 600/554 |
| 2009/0105604 A1* | 4/2009 | Bertagnoli et al. | 600/546 |
| 2009/0124860 A1* | 5/2009 | Miles et al. | 600/202 |
| 2009/0177112 A1* | 7/2009 | Gharib et al. | 600/554 |
| 2009/0192403 A1* | 7/2009 | Gharib et al. | 600/546 |
| 2009/0204016 A1* | 8/2009 | Gharib et al. | 600/546 |
| 2009/0204176 A1* | 8/2009 | Miles et al. | 607/48 |
| 2009/0209879 A1* | 8/2009 | Kaula et al. | 600/546 |
| 2009/0259108 A1* | 10/2009 | Miles et al. | 600/202 |
| 2010/0010367 A1* | 1/2010 | Foley et al. | 600/546 |
| 2010/0036384 A1 | 2/2010 | Gorek et al. | |
| 2010/0069783 A1 | 3/2010 | Miles et al. | |
| 2010/0076335 A1* | 3/2010 | Gharib et al. | 600/546 |
| 2010/0094093 A1* | 4/2010 | Miles et al. | 600/202 |
| 2010/0105986 A1* | 4/2010 | Miles et al. | 600/214 |
| 2010/0105987 A1 | 4/2010 | Miles et al. | |
| 2010/0113884 A1* | 5/2010 | Miles et al. | 600/210 |
| 2010/0130827 A1 | 5/2010 | Pimenta et al. | |
| 2010/0137690 A1* | 6/2010 | Miles et al. | 600/202 |
| 2010/0152603 A1* | 6/2010 | Miles et al. | 600/546 |
| 2010/0152604 A1* | 6/2010 | Kaula et al. | 600/546 |
| 2010/0160738 A1* | 6/2010 | Miles et al. | 600/202 |
| 2010/0174146 A1* | 7/2010 | Miles et al. | 600/202 |
| 2010/0174147 A1* | 7/2010 | Miles et al. | 600/202 |
| 2010/0174148 A1* | 7/2010 | Miles et al. | 600/202 |
| 2010/0249644 A1* | 9/2010 | Miles et al. | 600/554 |
| 2010/0273738 A1* | 10/2010 | Valcke et al. | 514/56 |
| 2010/0312103 A1 | 12/2010 | Gorek et al. | |
| 2010/0317989 A1* | 12/2010 | Gharib et al. | 600/554 |
| 2011/0144439 A1* | 6/2011 | Miles et al. | 600/202 |
| 2011/0184308 A1* | 7/2011 | Kaula et al. | 600/546 |
| 2011/0196210 A1* | 8/2011 | Miles et al. | 600/224 |
| 2011/0301631 A1* | 12/2011 | Gharib et al. | 606/191 |
| 2011/0313530 A1* | 12/2011 | Gharib et al. | 623/17.16 |
| 2012/0095360 A1* | 4/2012 | Runney et al. | 600/546 |

OTHER PUBLICATIONS

"Nerve Proximity and Status Detection System and Method," International Search Report from International Application No. PCT/US01/18606, Oct. 18, 2001, 2 pages.

"Relative Nerve Movement and Status Detection System and Method," International Search Report from International Application No. PCT/US01/18579, Jan. 15, 2002, 3 pages.

"System and Method for Determining Nerve Proximity Direction and Pathology During Surgery," International Search Report from International Application No. PCT/US02/22247, Mar. 27, 2003, 4 pages.

"System and Methods for Determining Nerve Direction to a Surgical Instrument," International Search Report from International Application No. PCT/US03/02056, Aug. 12, 2003, 2 pages.

"Systems and Methods for Performing Percutaneous Pedicle Integrity Assessments," International Search Report from International Application No. PCT/US02/35047, Aug. 11, 2003, 3 pages.

"Systems and Methods for Performing Surgery Procedures and Assessments," International Search Report from International Application No. PCT/US02/30617, Jun. 5, 2003, 4 pages.

"Systems and Methods for Performing Neurophysiologic Assessments During Spine Surgery," International Search Report from International Application No. PCT/US06/03966, Oct. 23, 2006, 3 pages.

"Multi-Channel Stimulation Threshold Detection Algorithm for Use in Neurophysiology Monitoring," International Search Report from International Application No. PCT/US06/37013, Mar. 19, 2007, 5 pages.

"Neurophysiologic Monitoring System," International Search Report and the Written Opinion from International Application No. PCT/US08/04427, Jul. 28, 2008, 6 pages.

"Neurovision SE Nerve Locator/Monitor," RLN Systems Inc. Operator's Manual, 1999, 22 pages.

Calancie et al., "Stimulus-Evoked EMG Monitoring During Transpedicular Lumbosacral Spine Instrumentation," *Spine*, 1994, 19(24): 2780-2786.

Holland et al., "Higher Electrical Stimulus Intensities are Required to Activate Chronically Compressed Nerve Roots. Implications for Intraoperative Electromyographic Pedicle Screw Testing," *Spine*, 1998, 23(2): 224-227.

* cited by examiner

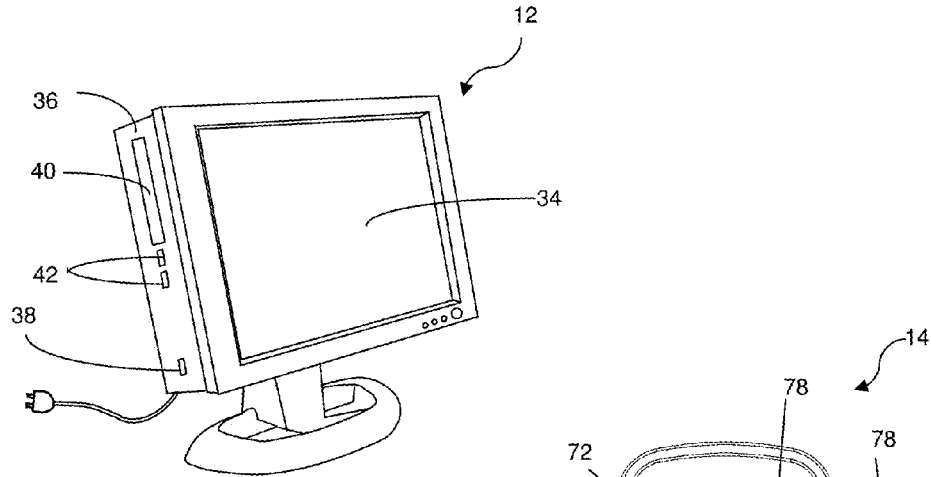
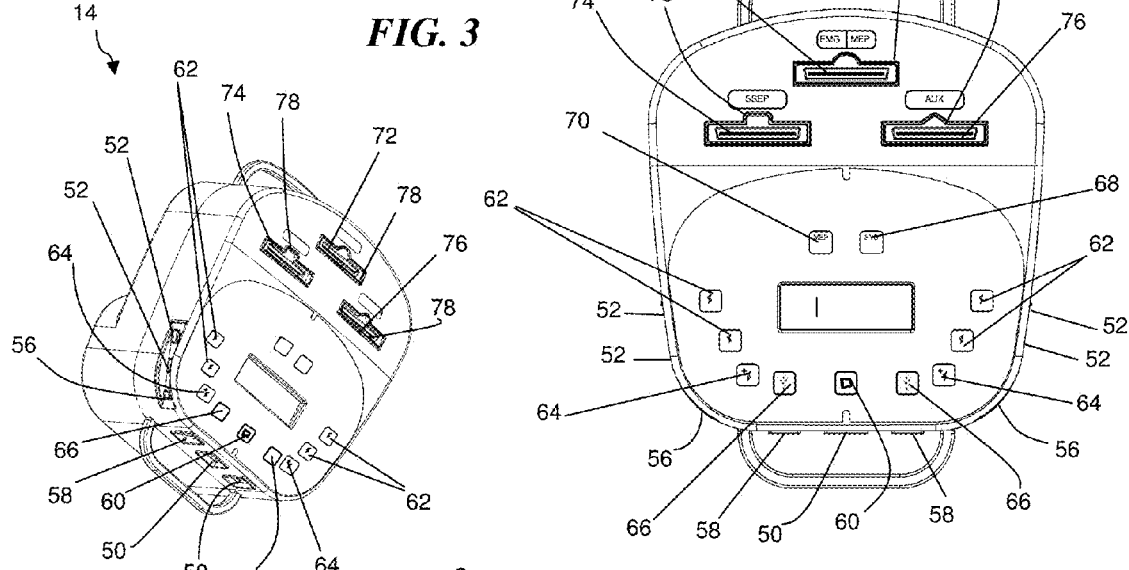
FIG. 3
FIG. 4
FIG. 5
FIG. 6

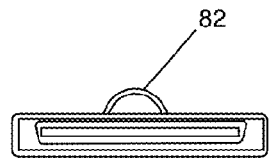
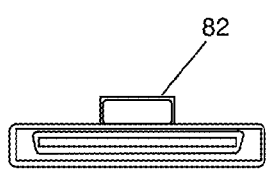
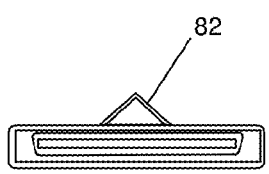
*FIG. 8A*  *FIG. 8B*  *FIG. 8C*
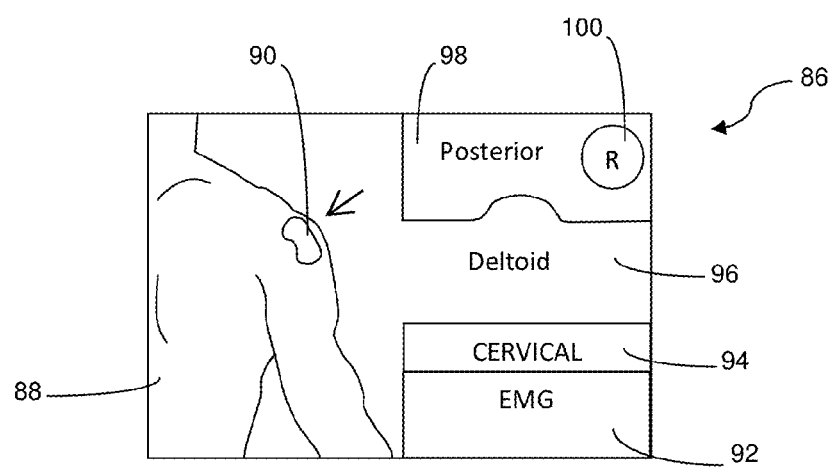
*FIG. 9*
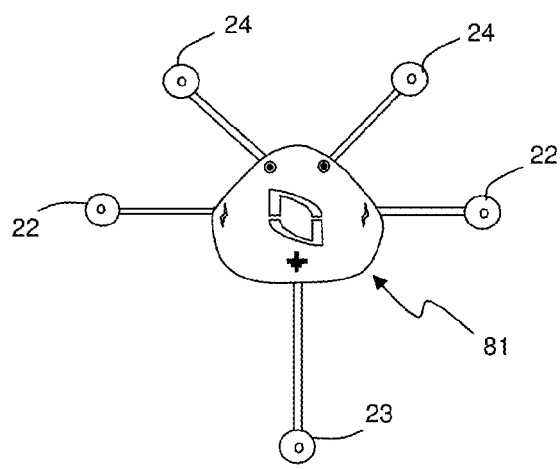
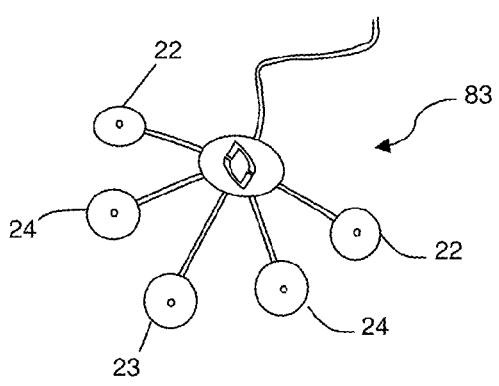
*FIG. 10A*  *FIG. 10B*

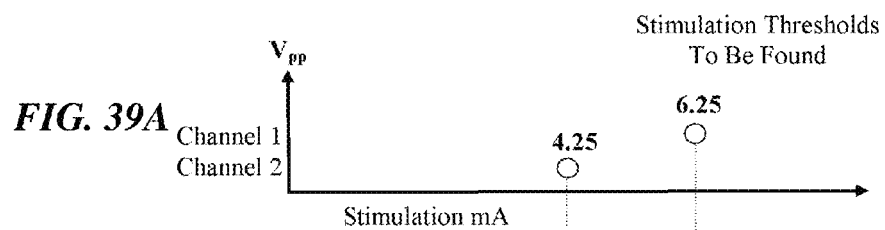
FIG. 39A
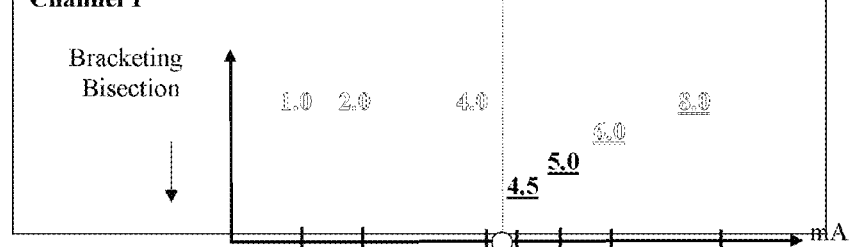
FIG. 39B
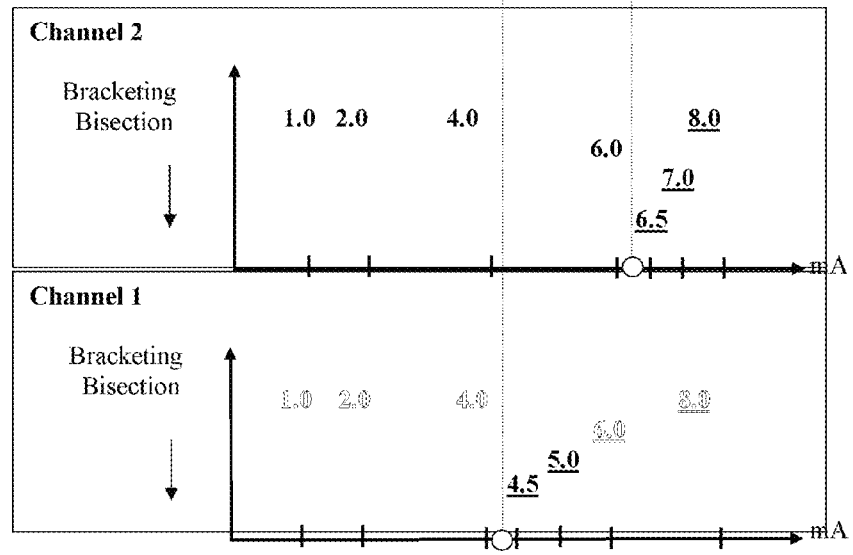
FIG. 39C
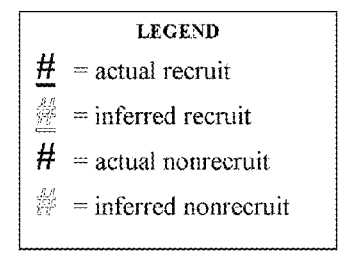

NEUROPHYSIOLOGIC MONITORING

CROSS-REFERENCE TO RELATED APPLICATIONS

This application is a non-provisional patent application claiming the benefit of priority from commonly owned and U.S. Provisional Patent Application Ser. No. 61/384,186, entitled "Amplitude Discrimination Algorithm for Use in Neurophysiologic Monitoring," filed on Sep. 17, 2010, the entire contents of which is hereby expressly incorporated by reference into this disclosure as if set forth in its entirety herein.

FIELD

The present application relates generally to neurophysiologic monitoring, and more particularly, to a system and methods for neurophysiologic monitoring that are capable of discerning between simultaneous background activity (non-physiologic or physiologic) and evoked neurophysiologic activity.

BACKGROUND

Neurophysiologic monitoring has become an increasingly important adjunct to surgical procedures in which neural tissue may be at risk. Spinal surgery, in particular, involves working close to delicate neural tissue in and surrounding the spine, which can be damaged in any number of different ways. Because of the complex structure of the spine and nervous system, no single neurophysiologic monitoring technique has been developed that adequately assesses the risk to nervous tissue in all situations. For this reason, two or more complex techniques are often used concurrently during surgery. Examples of such techniques include free-run (spontaneous) electromyography (EMG), stimulated (evoked) EMG, and motor evoked potentials (MEP).

Free-run EMG, stimulated EMG, and MEP testing have historically required specially-trained neurophysiologists to perform the testing. Even though performed by specialists, interpreting the complex waveforms in this fashion is nonetheless disadvantageously prone to human error and can be disadvantageously time consuming, adding to the duration of the operation and translating into increased health care costs. Even more costly is the fact that the neurophysiologist is required in addition to the surgeon performing the spinal operation.

Surgeon-operable systems have attempted to overcome some of these difficulties. However, performing multiple techniques simultaneously can still be a challenge because optimal signal response characteristics may vary between the different techniques, but the response activity associated with one technique may comingle with the response activity associated with another technique. For example, performing free-run EMG testing during a posterior lumbar fusion procedure is advantageous in that it provides a surgeon with continuous, real-time feedback regarding the health of the nerve roots during the procedure. Additionally, static pedicle screw testing is also advantageous in the same procedure because it can verify proper positioning of the screw within the pedicle. However when performing both techniques simultaneously, background noise and/or neurophysiologic activity from the free-run EMG technique may comingle with the compound muscle action potential (CMAP) responses evoked by, for example, the static pedicle screw testing. Such comingling could affect the static pedicle screw testing results in such a way as to lead to a false positive result.

The system and methods described herein are directed at eliminating, or at least reducing, the effects of the above-described problems.

SUMMARY OF THE INVENTION

The present invention provides a surgeon with valuable information that allows for the efficient assessment of risk to neural tissue before, during, and/or after a surgical procedure.

According to one aspect, the present invention comprises a neurophysiology system that includes a control unit, a patient module, and a plurality of surgical accessories designed to couple to the patient module. The control unit includes a power supply and is programmed to receive user commands, activate stimulation in a plurality of predetermined modes, process signal data according to defined algorithms, display received parameters and processed data, and monitor system status. The patient module is in communication with the control unit. The patient module includes signal conditioning circuitry, stimulation drive circuitry, and signal conditioning circuitry required to perform said stimulation in said predetermined modes. The system includes a plurality of processors programmed to perform a plurality of predetermined functions including at least two of static pedicle integrity testing, dynamic pedicle integrity testing, nerve proximity detection, neuromuscular pathway assessment, manual motor evoked potential monitoring, automatic motor evoked potential monitoring, manual somatosensory evoked potential monitoring, automatic somatosensory evoked potential monitoring, non-evoked monitoring including free-run EMG, and surgical navigation.

One or more of the predetermined functions rely (either in whole or in part) on the stimulation threshold technique to provide neurophysiologic assessments. Using this technique, stimulation thresholds are determined by electrically stimulating nerve tissue and analyzing the resulting muscle activity to determine the stimulation current level at which nerve tissue depolarizes. To make stimulation threshold determinations, muscle activity may be monitored by measuring electrical signals associated with muscle contraction (EMG). EMG responses can be characterized by a peak-to-peak voltage of $V_{pp}=V_{max}-V_{min}$. Characteristics of the electrical stimulation signal used may vary depending on several factors, including the particular nerve assessment performed, the spinal target level, the type of neural tissue stimulated (e.g. nerve root, spinal cord, brain, etc.), among others.

A basic premise underlying the stimulation threshold technique is that nerves have a characteristic threshold current level ($I_{Thresh}$) at which they will depolarize and cause a significant EMG response. A significant EMG response may be defined as having a $V_{pp}$ greater than a predetermined threshold voltage ($V_{Thresh}$). By way of example only, the $V_{Thresh}$ may be selected from a range including 20 µV-300 µV. Stimulation with a current below the threshold level, $I_{Thresh}$, will not evoke a significant EMG response, while stimulation with a current at or above the threshold level will evoke a significant EMG response. This relationship between the stimulation current and the EMG response may be represented via a "recruitment curve." When stimulation does not evoke a significant EMG response the stimulation current is said to have not "recruited." When stimulation does evoke a significant EMG response the stimulation current is said to have "recruited." $I_{Thresh}$ is the lowest stimulation current that recruits a significant EMG response. The recruitment curve further demonstrates a linear region, in which increasing the stimulus intensity (mA) leads to a corresponding increase in threshold response amplitude ($V_{pp}$) until there is saturation, in which increasing the stimulus intensity (mA) will not lead to any further increase in threshold response amplitude ($V_{pp}$).

According to another aspect, the present invention includes an amplitude discrimination algorithm for quickly and accurately discerning between background noise or activity and an evoked neurophysiologic response when two or more monitoring functions, or modalities, are concurrently employed.

According to one embodiment, the amplitude discrimination algorithm may be employed whenever free-run EMG testing is performed concurrently with a stimulated EMG threshold technique. In particular, the amplitude discrimination algorithm may be particularly advantageous when stimulated EMG is employed for static dynamic pedicle integrity testing, dynamic pedicle integrity testing, nerve proximity detection, and neuromuscular pathway assessments. The amplitude discrimination algorithm may also be advantageously utilized during manual and automatic MEP monitoring.

According to one embodiment, prior to commencing monitoring, the sensitivity setting on the neurophysiology system is increased until there is no background noise in the EMG recording channels. This sensitivity setting represents the setpoint. The free-run EMG sensitivity setting is automatically set to the setpoint sensitivity. Then, the stimulated EMG sensitivity setting is automatically increased to a predetermined level above the setpoint. This predetermined level can be a fixed increase (a predetermined voltage increase from the setpoint, for example 40 µV) or, it can be a percent increase (a predetermined percentage increase in voltage from the set point, for example 50%). The amplitude discrimination boundary represents the difference in sensitivity between the free-run and stimulated EMG sensitivity settings.

According to another embodiment, prior to commencing monitoring, the sensitivity setting on the neurophysiology system is increased until there is no background noise or background neurophysiologic activity in the EMG recording channels. This sensitivity setting represents the setpoint. From the setpoint and after a brief delay, the free-run EMG sensitivity setting is automatically decreased to a predetermined level below the setpoint. Then, the stimulated EMG sensitivity setting is automatically increased to a predetermined level above the setpoint. This predetermined level can be a fixed offset (a predetermined voltage value from the setpoint, for example 20 µV) or, it can be a percent offset (a predetermined percentage difference in voltage from the set point, for example 20%). The amplitude discrimination boundary represents the difference in sensitivity between the free-run and stimulated EMG sensitivity settings.

According to one or more additional embodiments, the amplitude discrimination algorithm may be further configured to adjust the stimulated EMG results to account for the effects that the sensitivity setting increases may have on the response threshold values.

Using the amplitude discrimination algorithm in accordance with any embodiment disclosed herein, the likelihood of false positives in stimulated EMG recordings associated with background noise "contamination' and background neurophysiologic activity is decreased because the sensitivity settings are increased to attenuate such background activity. Use of the algorithm also decreases the likelihood of false negatives in free-run EMG recordings because the optimal sensitivity setting for free-run EMG recordings is not sacrificed for high-quality stimulated EMG responses. Decreasing the incidence of false positives and negatives promotes confidence in the neurophysiology system and provides opportunities for improved patient outcomes.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIG. 3 is a perspective view of an example of a control unit forming part of the neurophysiology system of FIG. 1;

FIGS. 4-6 are perspective, top, and side views, respectively, of an example of a patient module forming part of the neurophysiology system of FIG. 1;

FIGS. 8A-8C are side views of various examples of harness ports forming part of the neurophysiology system of FIG. 1;

FIG. 9 is a plan view of an example of a label affixed to an electrode connector forming part of the neurophysiology system of FIG. 1;

FIGS. 10A-10B are top views of examples of electrode caps forming part of the neurophysiology system of FIG. 1;

FIG. 39 A-C are graphs illustrating use of the threshold hunting algorithm of FIG. 38 and further omitting stimulations when the likely result is already clear from previous data;

DETAILED DESCRIPTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The systems disclosed herein boast a variety of inventive features and components that warrant patent protection, both individually and in combination. It is also expressly noted that, although described largely in terms of use in spinal surgery, the surgical system and related methods described herein are suitable for use in any number of additional procedures, surgical or otherwise, wherein assessing the health of spinal nerves, the spinal cord, and/or various other nerve tissue may prove beneficial.

Figure 1:
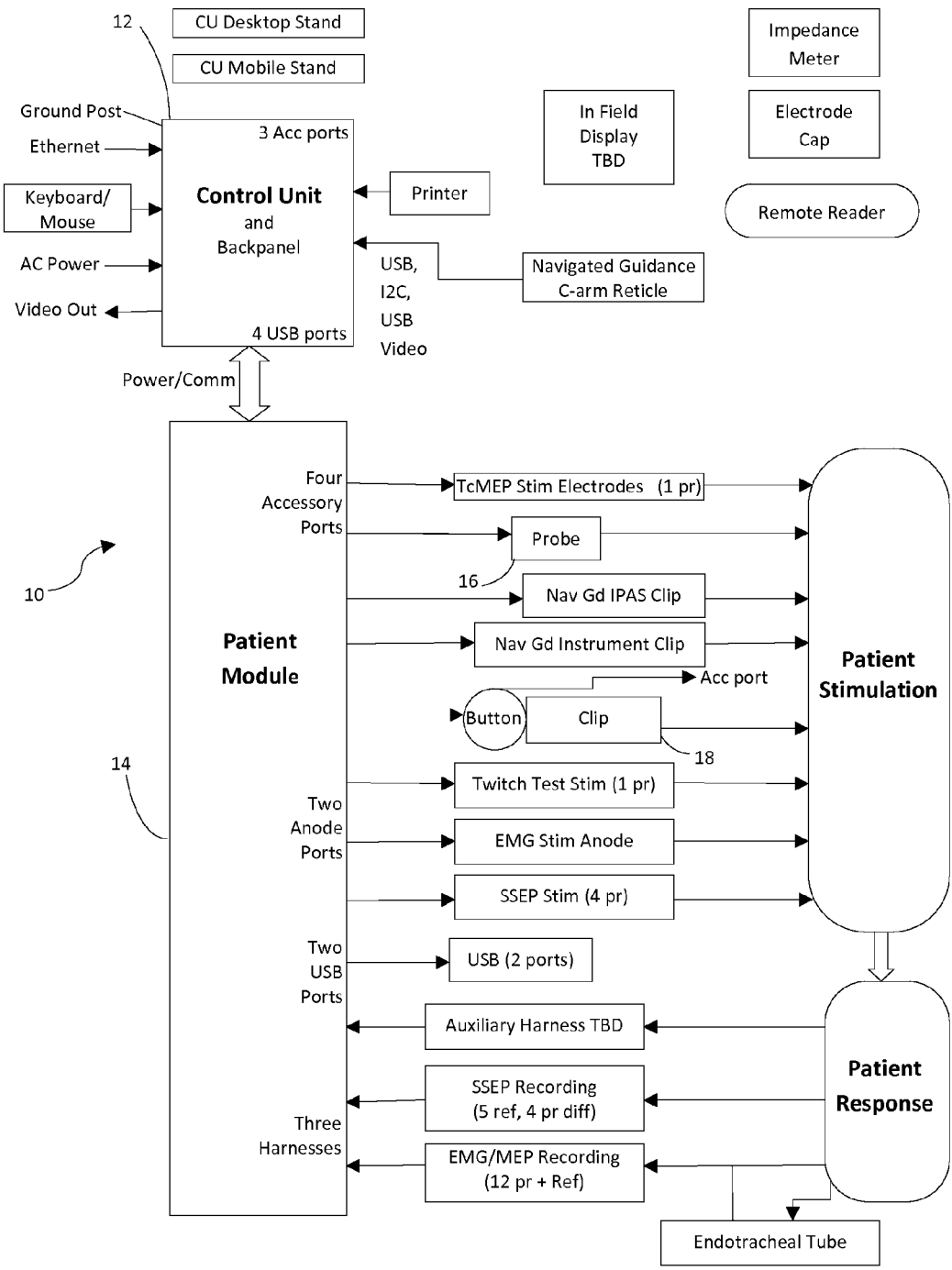
FIG. 1 is a block diagram of an exemplary surgical system capable of conducting multiple nerve and spinal cord monitoring functions including but not necessarily limited to static pedicle integrity testing, dynamic pedicle integrity testing, nerve proximity detection, free-run EMG, stimulated EMG, neuromuscular pathway assessment, Manual MEP monitoring, Automatic MEP monitoring, Manual SSEP monitoring, Automatic SSEP monitoring, and surgical navigation.
Figure 2:
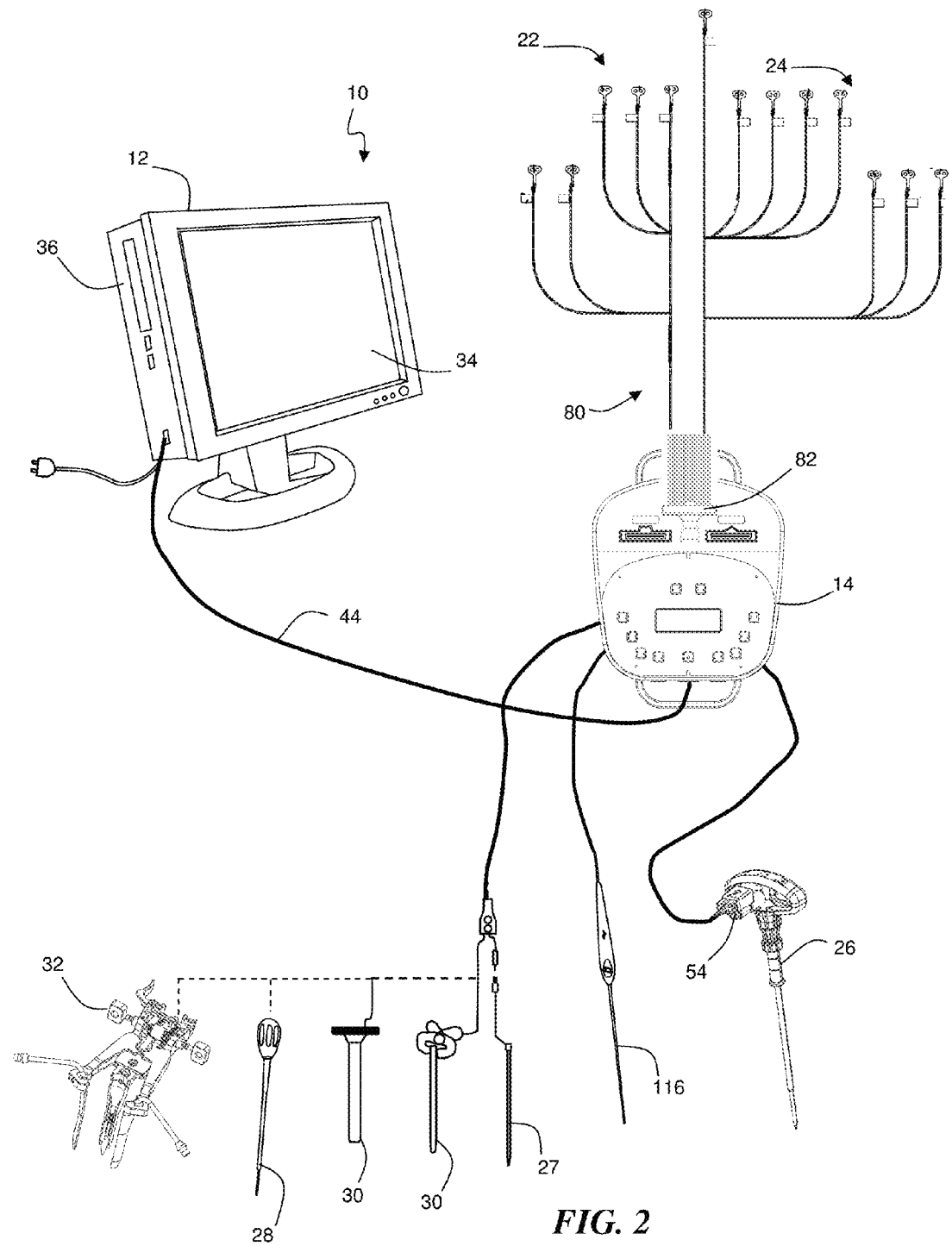
FIG. 2 is a perspective view showing examples of several components of the neurophysiology system of FIG. 1.

A surgeon operable neurophysiology system 10 is described herein and is capable of performing a number of neurophysiologic and/or guidance assessments at the direction of the surgeon (and/or other members of the surgical team). By way of example only, FIGS. 1-2 illustrate the basic components of the neurophysiology system 10. The system comprises a control unit 12 (including a main display 34 preferably equipped with a graphical user interface (GUI) and a processing unit 36 that collectively contain the essential processing capabilities for controlling the system 10), a patient module 14, a stimulation accessory (e.g. a stimulation probe 16, a stimulation clip 18 for connection to various surgical instruments, an inline stimulation hub 20, and stimulation electrodes 22), and a plurality of recording electrodes 24 for detecting electrical potentials. The stimulation clip 18 may be used to connect any of a variety of surgical instruments to the system 10, including, but not necessarily limited to a pedicle access needle 26, k-wire 27, tap 28, dilator(s) 30, tissue retractor 32, etc. One or more secondary feedback devices (e.g. secondary display 46 in FIG. 11-12) may also be provided for additional expression of output to a user and/or receiving input from the user.

In one embodiment, the neurophysiology system 10 may be configured to execute any of the functional modes including, but not necessarily limited to, static pedicle integrity testing ("Basic Stimulated EMG"), dynamic pedicle integrity testing ("Dynamic Stimulated EMG"), nerve proximity detection ("XLIF®"), neuromuscular pathway assessment ("Twitch Test"), motor evoked potential monitoring ("MEP Manual" and "MEP Automatic"), somatosensory evoked potential monitoring ("SSEP Manual" and "SSEP Automatic"), non-evoked monitoring ("Free-run EMG") and surgical navigation ("Navigated Guidance"). The neurophysiology system 10 may also be configured for performance in any of the lumbar, thoracolumbar, and cervical regions of the spine.

Before further addressing the various functional modes of the surgical system 10, the hardware components and features of the system 10 will be described in further detail. The control unit 12 of the neurophysiology system 10, illustrated by way of example only in FIG. 3, includes a main display 34 and a processing unit 36, which collectively contain the essential processing capabilities for controlling the neurophysiology system 10. The main display 34 is preferably equipped with a graphical user interface (GUI) capable of graphically communicating information to the user and receiving instructions from the user. The processing unit 36 contains computer hardware and software that commands the stimulation source (e.g. patient module 14, FIGS. 4-6), receives digital and/or analog signals and other information from the patient module 14, processes EMG, MEP, and SSEP response signals, and displays the processed data to the operator via the display 34. The primary functions of the software within the control unit 12 include receiving user commands via the touch screen main display 34, activating stimulation in the appropriate mode (Basic Stimulated EMG, Dynamic Stimulated EMG, XLIF®, MEP automatic, MEP manual, SSEP automatic, SSEP manual, and Twitch Test), processing signal data according to defined algorithms, displaying received parameters and processed data, and monitoring system status. According to one example embodiment, the main display 34 may comprise a 15" LCD display equipped with suitable touch screen technology and the processing unit 36 may comprise a 2 GHz processor. The processing unit 36 shown in FIG. 3 further includes a powered USB port 38 for connection to the patient module 14, a media drive 40 (e.g. CD, CD-RW, DVD, DVD-RW, etc.), a network port, wireless network card, and a plurality of additional ports 42 (e.g. USB, IEEE 1394, infrared, etc.) for attaching additional accessories, such as for example only, navigated guidance sensors, auxiliary stimulation anodes, and external devices (e.g. printer, keyboard, mouse, etc.). Preferably, during use the control unit 12 sits near the surgical table but outside the surgical field, such as for example, on a table top or a mobile stand. It will be appreciated, however, that if properly draped and protected, the control unit 12 may be located within the surgical (sterile) field.

The patient module 14, shown by way of example only in FIGS. 4-6, is communicatively linked to the control unit 12. In this embodiment the patient module 14 is communicatively linked with and receives power from the control unit 12 via a USB data cable 44. However, it will be appreciated that the patient module 14 may be supplied with its own power source and other known data cables, as well as wireless technology, may be utilized to establish communication between the patient module 14 and control unit 12. The patient module 14 contains a digital communications interface to communicate with the control unit 12, as well as the electrical connections to all recording and stimulation electrodes, signal conditioning circuitry, stimulator drive and steering circuitry, and signal conditioning circuitry required to perform all of the functional modes of the neurophysiology system 10, including but not necessarily limited to Basic Stimulated EMG, Dynamic Stimulated EMG, XLIF®, Twitch Test, MEP Manual and MEP Automatic, and SSEP. In one example, the patient module 14 includes thirty-two recording channels and eleven stimulation channels. A display (e.g. an LCD screen) may be provided on the face of the patient module 14, and may be utilized for showing simple status readouts (for example, results of a power on test, the electrode harnesses attached, and impedance data, etc.) or more procedure related data (for example, a stimulation threshold result, current stimulation level, selected function, etc.). The patient module 14 may be positioned near the patient in the sterile field during surgery. By way of example, the patient module 14 may be attached to bed rail with the aid of a hook 48 attached to, or forming a part of, the patient module 14 casing.

With reference to FIGS. 4-6, patient module 14 comprises a multitude of ports and indicators for connecting and verifying connections between the patient module 14 and other system components. A control unit port 50 is provided for data and power communication with the control unit 12, via USB data cable 44 as previously described. There are four accessory ports 52 provided for connecting up to the same number of surgical accessories, including, but not necessarily limited to, stimulation probe 16, stimulation clip 18, inline stimulation hub 20, and navigated guidance sensor (or tilt sensor) 54. The accessory ports 52 include a stimulation cathode and transmit digital communication signals, tri-color LED drive signals, button status signals, identification signals, and power between the patient module 14 and the attached accessory. A pair of anode ports 56, preferably comprising 2 wire DIN connectors, may be used to attach auxiliary stimulation anodes should it become desirable or necessary to do so during a procedure. A pair of USB ports 58 are connected as a USB hub to the control unit 12 and may be used to make any number of connections, such as for example only, a portable storage drive.

As soon as a device is plugged into any one of ports 50, 52, 56, or 58, the neurophysiology system 10 automatically performs a circuit continuity check to ensure the associated device will work properly. Each device forms a separate closed circuit with the patient module such that the devices may be checked independent of each other. If one device is not working properly the device may be identified individually while the remaining devices continue to indicate their valid status. An indicator LED is provided for each port to convey the results of the continuity check to the user. Thus, according to the example embodiment of FIGS. 7-9, the patient module 14 includes one control unit indicator 60, four accessory indicators 62, two anode indicators 64, and two USB indicators 66. According to a preferred embodiment, if the system detects an incomplete circuit during the continuity check, the appropriate indicator will turn red alerting the user that the device might not work properly. On the other hand, if a complete circuit is detected, the indicator will appear green signifying that the device should work as desired. Additional indicator LEDs are provided to indicate the status of the system and the MEP stimulation. The system indicator 68 will appear green when the system is ready and red when the system is not ready. The MEP stim indicator 70 lights up when the patient module is ready to deliver and MEP stimulation signal. In one embodiment, the MEP stim indicator 68 appears yellow to indicate a ready status.

To connect the array of recording electrodes 24 and stimulation electrodes 22 utilized by the system 10, the patient module 14 also includes a plurality of electrode harness ports. In the embodiment shown, the patient module 14 includes an EMG/MEP harness port 72, SSEP harness port 74, and an Auxiliary harness port 76 (for expansion and/or custom harnesses). Each harness port 72, 74, and 76 includes a shaped socket 78 that corresponds to a matching shaped connector 82 on the appropriate electrode harness 80. In addition, the neurophysiology system 10 may preferably employ a color code system wherein each modality (e.g. EMG, EMG/MEP, and SSEP) has a unique color associated with it. By way of example only and as shown herein, EMG monitoring (including, screw tests, detection, and nerve retractor) may be associated with the color green, MEP monitoring with the color blue, and SSEP monitoring may be associated with the color orange. Thus, each harness port 72, 74, 76 is marked with the appropriate color which also corresponds to the appropriate harness 80. Utilizing the combination of the dedicated color code and the shaped socket/connector interface simplifies the setup of the system, reduces errors, and can greatly minimize the amount of pre-operative preparation necessary. The patient module 14, and especially the configuration of quantity and layout of the various ports and indicators, has been described according to one example embodiment of the present invention. It should be appreciated, however, that the patient module 14 could be configured with any number of different arrangements without departing from the scope of the invention.

Figure 7:
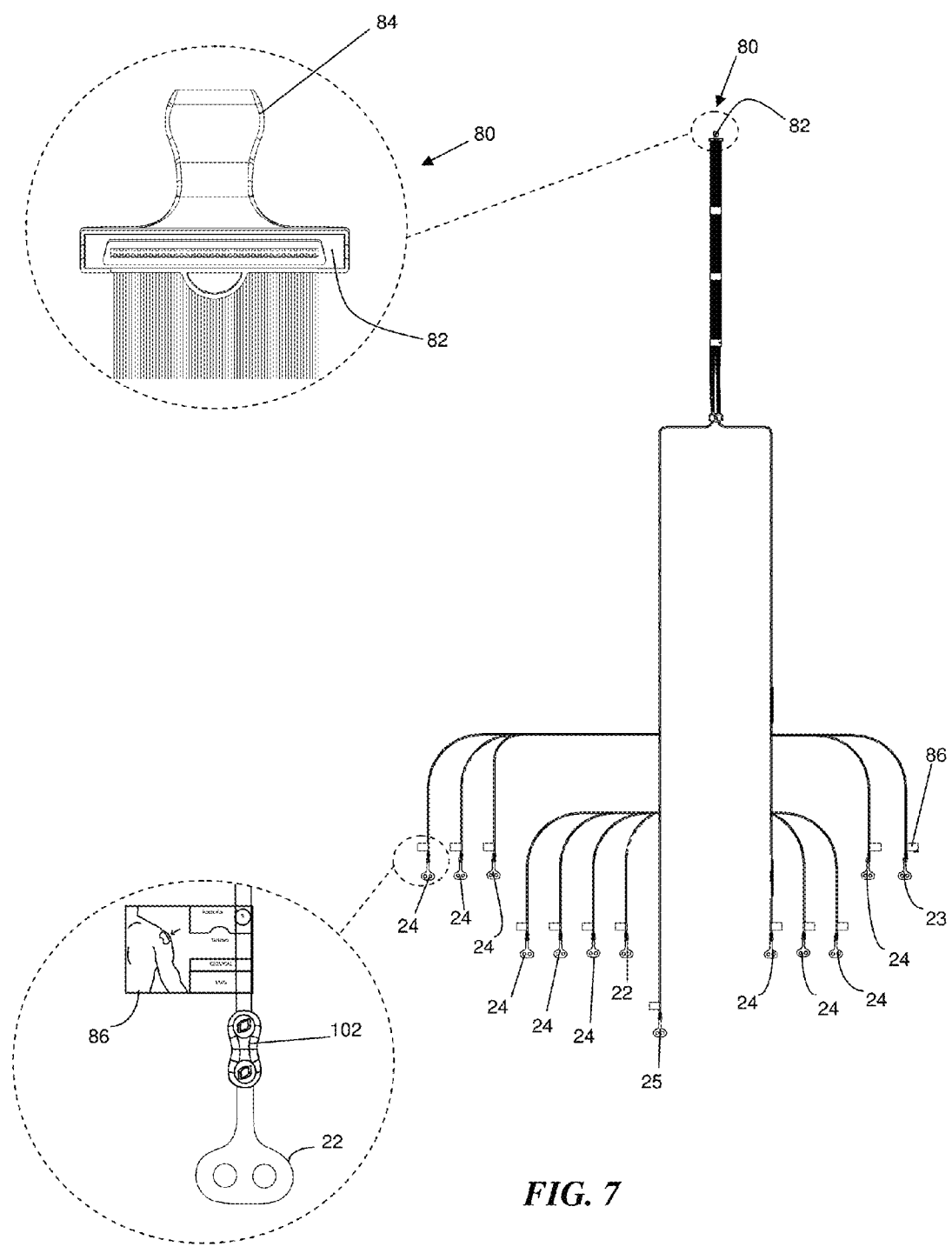
FIG. 7 is a top view of an electrode harness forming part of the neurophysiology system of FIG. 1.

As mentioned above, to simplify setup of the system 10, all of the recording electrodes 24 and stimulation electrodes 22 required to perform one of the various functional modes (including a common electrode 23 providing a ground reference to pre-amplifiers in the patient module 14, and an anode electrode 25 providing a return path for the stimulation current) are bundled together and provided in single electrode harness 80, as illustrated, by way of example only, in FIG. 7. Depending on the desired function or functions to be used during a particular procedure, different groupings of recoding electrodes 24 and stimulation electrodes 22 may be required. By way of example, the SSEP function requires more stimulating electrodes 22 than either the EMG or MEP functions, but also requires fewer recording electrodes than either of the EMG and MEP functions. To account for the differing electrode needs of the various functional modes, the neurophysiology system 10 may employ different harnesses 80 tailored for the desired modes. According to one embodiment, three different electrode harnesses 80 may be provided for use with the system 10, an EMG harness, an EMG/MEP harness, and an SSEP harness.

At one end of the harness 80 is the shaped connector 82. As described above, the shaped connector 82 interfaces with the shaped socket 72, 74, or 76 (depending on the functions harness 80 is provided for). Each harness 80 utilizes a shaped connector 82 that corresponds to the appropriate shaped socket 72, 74, 76 on the patient module 14. If the shapes of the socket and connector do not match the harness 80, connection to the patient module 14 cannot be established. According to one embodiment, the EMG and EMG/MEP harnesses both plug into the EMG/MEP harness port 72 and thus they both utilize the same shaped connector 82. FIGS. 8A-8C illustrate the various exemplary shape profiles used by the different harness ports 72, 74, 76 and connectors 82. FIG. 8A illustrates the half-circular shape associated with the EMG and EMG/MEP harness and port 72. FIG. 8B illustrates the rectangular shape utilized by the SSEP harness and port 74. Finally, FIG. 8C illustrates the triangular shape utilized by the Auxiliary harness and port 76. Each harness connector 82 includes a digital identification signal that identifies the type of harness 80 to the patient module 14. At the opposite end of the electrode harness 80 are a plurality of electrode connectors 102 linked to the harness connector 82 via a wire lead. Using the electrode connector 102, any of a variety of known electrodes may be used (e.g., surface dry gel electrodes, surface wet gel electrodes, and needle electrodes).

To facilitate easy placement of scalp electrodes used during MEP and SSEP modes, an electrode cap 81, depicted by way of example only in FIG. 10A may be used. The electrode cap 81 includes two recording electrodes 23 for SSEP monitoring, two stimulation electrodes 22 for MEP stimulation delivery, and an anode 23. Graphic indicators may be used on the electrode cap 81 to delineate the different electrodes. By way of example, lightning bolts may be used to indicate a stimulation electrode, a circle within a circle may be used to indicate recording electrodes, and a stepped arrow may be used to indicate the anode electrode. The anode electrode wire is colored white to further distinguish it from the other electrodes and is significantly longer that the other electrode wires to allow placement of the anode electrode on the patient's shoulder. The shape of the electrode cap 81 may also be designed to simplify placement. By way of example only, the cap 81 has a pointed end that may point directly toward the patient's nose when the cap 81 is centered on the head in the correct orientation. A single wire may connect the electrode cap 81 to the patient module 14 or electrode harness 80, thereby decreasing the wire population around the upper regions of the patient. Alternatively, the cap 81 may be equipped with a power supply and a wireless antenna for communicating with the system 10. FIG. 10B illustrates another example embodiment of an electrode cap 83 similar to cap 81. Rather than using graphic indicators to differentiate the electrodes, colored wires may be employed. By way of example, the stimulation electrodes 22 are colored yellow, the recording electrodes 24 are gray, and the anode electrode 23 is white. The anode electrode is seen here configured for placement on the patient's forehead. According to an alternate embodiment, the electrode cap (not shown) may comprise a strap or set of straps configured to be worn on the patient's head. The appropriate scalp recording and stimulation sites may be indicated on the straps. By way of example, the electrode cap may be imbued with holes overlying each of the scalp recording sites (for SSEP) and scalp stimulation sites (for MEP). According to a further example embodiment, the border around each hole may be color coded to match the color of an electrode lead wire designated for that site. In this instance, the recording and stimulation electrodes designated for the scalp are preferably one of a needle electrode and a corkscrew electrode that can be placed in the scalp through the holes in the cap.

In addition to or instead of color-coding the electrode lead wires to designated intended placement, the end of each wire lead next to the electrode connector 102 may be tagged with a label 86 that shows or describes the proper positioning of the electrode on the patient. The label 86 preferably demonstrates proper electrode placement graphically and textually. As shown in FIG. 9, the label may include, a graphic image showing the relevant body portion 88 and the precise electrode position 90. Textually, the label 86 may indicate the side 100 and muscle (or anatomic location) 96 for placement, the function of the electrode (e.g. stimulation, recording channel, anode, and reference—not shown), the patient surface (e.g. anterior or posterior), the spinal region 94, and the type of monitoring 92 (e.g. EMG, MEP, SSEP, by way of example only). According to one embodiment (set forth by way of example only), the electrode harnesses 80 are designed such that the various electrodes may be positioned about the patient (and preferably labeled accordingly) as described in Table 1 for Lumbar EMG, Table 2 for Cervical EMG, Table 3 for Lumbar/Thoracolumbar EMG and MEP, Table 4 for Cervical EMG and MEP, and Table 5 for SSEP:

TABLE 1

Lumbar EMG

| Electrode Type | Electrode Placement | Spinal Level |
| --- | --- | --- |
| Ground | Upper Outer Thigh | — |
| Anode | Latissimus Dorsi | — |
| Stimulation | Knee | — |
| Recording | Left Tibialis Anterior | L4, L5 |
| Recording | Left Gastroc. Medialis | S1, S2 |
| Recording | Left Vastus Medialis | L2, L3, L4 |
| Recording | Left Biceps Femoris | L5, S1, S2 |
| Recording | Right Biceps Femoris | L5, S1, S2 |
| Recording | Right Vastus Medialis | L2, L3, L4 |
| Recording | Right Gastroc. Medialis | S1, S2 |
| Recording | Right Tibialis Anterior | L4, L5 |

TABLE 2

Cervical EMG

| Electrode Type | Electrode Placement | Spinal Level |
| --- | --- | --- |
| Ground | Shoulder | — |
| Anode | Mastoid | — |
| Stimulation | Inside Elbow | — |
| Recording | Left Triceps | C7, C8 |
| Recording | Left Flexor Carpi Radialis | C6, C7, C8 |
| Recording | Left Deltoid | C5, C6 |
| Recording | Left Trapezius | C3, C4 |
| Recording | Left Vocal Cord | RLN |
| Recording | Right Vocal Cord | RLN |
| Recording | Right Trapezius | C3, C4 |
| Recording | Right Deltoid | C5, C6 |
| Recording | Right Flexor Carpi Radialis | C6, C7, C8 |
| Recording | Right Triceps | C7, C8 |

TABLE 3

Lumbar/Thoracolumbar EMG + MEP

| Electrode Type | Electrode Placement | Spinal Level |
| --- | --- | --- |
| Ground | Upper Outer Thigh | — |
| Anode | Latissimus Dorsi | — |
| Stimulation | Knee | — |
| Recording | Left Tibialis Anterior | L4, L5 |
| Recording | Left Gastroc. Medialis | S1, S2 |
| Recording | Left Vastus Medialis | L2, L3, L4 |
| Recording | Left Biceps Femoris | L5, S1, S2 |
| Recording | Left APB-ADM | C6, C7, C8, T1 |
| Recording | Right APB-ADM | C6, C7, C8, T1 |
| Recording | Right Biceps Femoris | L5, S1, S2 |
| Recording | Right Vastus Medialis | L2, L3, L4 |
| Recording | Right Gastroc. Medialis | S1, S2 |
| Recording | Right Tibialis Anterior | L4, L5 |

TABLE 4

Cervical EMG + MEP

| Electrode Type | Electrode Placement | Spinal Level |
| --- | --- | --- |
| Ground | Shoulder | — |
| Anode | Mastoid | — |
| Stimulation | Inside Elbow | — |
| Recording | Left Tibialis Anterior | L4, L5 |
| Recording | Left Flexor Carpi Radialis | C6, C7, C8 |
| Recording | Left Deltoid | C5, C6 |
| Recording | Left Trapezius | C3, C4 |
| Recording | Left APB-ADM | C6, C7, C8, T1 |
| Recording | Left Vocal Cord | RLN |
| Recording | Right Vocal Cord | RLN |
| Recording | Right APB-ADM | C6, C7, C8, T1 |
| Recording | Right Trapezius | C3, C4 |
| Recording | Right Deltoid | C5, C6 |
| Recording | Right Flexor Carpi Radialis | C6, C7, C8 |
| Recording | Right Tibialis Anterior | L4, L5 |

TABLE 5

SSEP

| Electrode Type | Electrode Placement | Spinal Level |
| --- | --- | --- |
| Ground | Shoulder | — |
| Stimulation | Left Post Tibial Nerve | — |
| Stimulation | Left Ulnar Nerve | — |
| Stimulation | Right Post Tibial Nerve | — |
| Stimulation | Right Ulnar Nerve | — |
| Recording | Left Popliteal Fossa | — |
| Recording | Left Erb's Point | — |
| Recording | Left Scalp Cp3 | — |
| Recording | Right Popliteal Fossa | — |
| Recording | Right Erb's Point | — |
| Recording | Right Scalp Cp4 | — |
| Recording | Center Scalp Fpz | — |
| Recording | Center Scalp Cz | — |
| Recording | Center Cervical Spine | — |

Figures 11, 12:
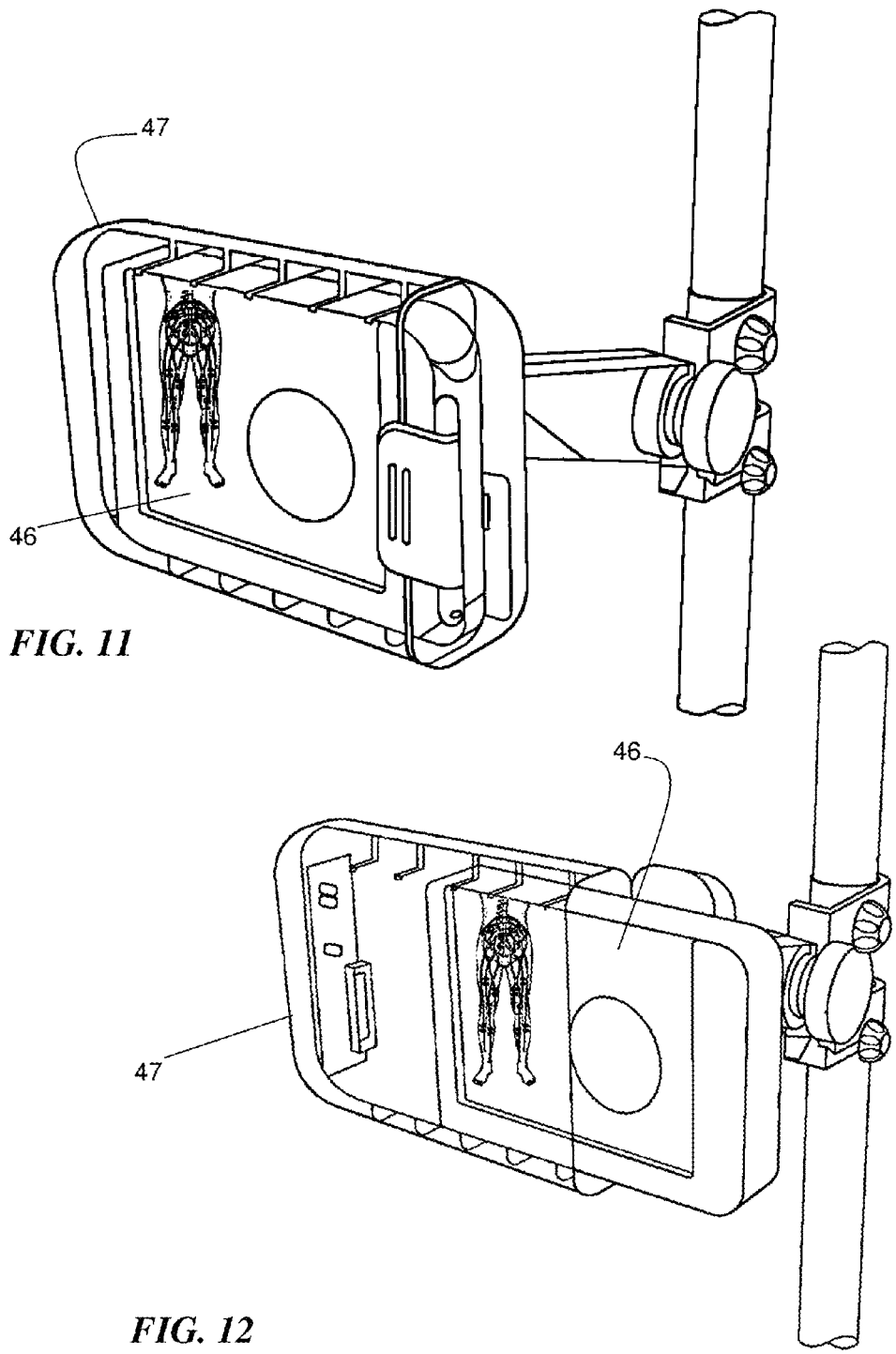
FIGS. 11-12 are perspective views of an example of a secondary display forming part of the neurophysiology system of FIG. 1.

As mentioned above, the neurophysiology monitoring system 10 may include a secondary display, such as for example only, the secondary display 46 illustrated in FIGS. 11-12. The secondary display 46 may be configured to display some or all of the information provided on main display 34. The information displayed to the user on the secondary display 34 may include, but is not necessarily limited to, alpha-numeric and/or graphical information regarding any of the selected function modes (e.g. SSEP Manual, SSEP Automatic, MEP Manual, MEP Automatic, Twitch Test, Basic Stimulated EMG, Dynamic Stimulated EMG, XLIF®, Free-Run EMG, and Navigated Guidance), attached accessories (e.g. stimulation probe 16, stimulation clip 18, tilt sensor 54), electrode harness or harnesses attached, impedance test results, myotome/EMG levels, stimulation levels, history reports, selected parameters, test results, etc. In one embodiment, the secondary display 46 may be configured to receive user input in addition to its display function. The secondary display 46 can thus be used as an alternate control point for the system 10. The control unit 12 and the secondary display 46 may be linked such that input may be received on from one display without changing the output shown on the other display. This would allow the surgeon to maintain focus on the patient and test results while still allowing other members of the OR staff to manipulate the system 10 for various purposes (e.g. inputting annotations, viewing history, etc.). The secondary display 46 may be battery powered. Advantageously, the secondary display 46 may be positioned inside the sterile field as well as outside the sterile field. For positioning within the sterile field a disposable sterile case 47 may be provided to house the display. Alternatively, the display 46 may be sterile bagged. Both the sterile case 47 and the secondary display 46 may be mounted to a pole, bed frame, light fixture, or other apparatus found near and/or in the surgical field. It is further contemplated that multiple secondary displays 46 may be linked to the control unit 12. This may effectively distribute neurophysiology information and control throughout the operating room. By way of example, a secondary display 46 may also be provided for the anesthesiologist. This may be particularly useful in providing the anesthesiologist with results from the Twitch Test and providing reminders about the use of paralytics, which may adversely affect the accuracy of the neurophysiology system 10. Wired or wireless technology may be utilized to link the secondary display 46 to the control unit 12.

Having described an example embodiment of the system 10 and the hardware components that comprise it, the neurophysiological functionality and methodology of the system 10 will now be described in further detail. Various parameters and configurations of the neurophysiology system 10 may depend upon the target location (i.e. spinal region) of the surgical procedure and/or user preference. In one embodiment, upon starting the system 10 the software will open to a startup screen, illustrated by way of example only, in FIG. 13.

The startup screen includes a profile selection window 160 from which the user may select from one of the standard profiles (e.g. "Standard Cervical," "Standard Thoracolumbar," and "Standard Lumbar") or any custom profiles that have been previously saved to the system. Profiles may be arranged for selection, alphabetically, by spinal region, or by other suitable criteria. Profiles may be saved to the control unit hard drive or to a portable memory device, such as for example, a USB memory drive, or on a web server.

Selecting a profile configures the system 10 to the parameters assigned for the selected profile (standard or custom). The availability of different function modes may depend upon the profile selected. By way of example only, selecting the cervical and thoracolumbar spinal regions may automatically configure the options to allow selection of the SSEP Manual, SSEP Automatic, MEP Manual, MEP Automatic, Twitch Test, Basic Stimulated EMG, Dynamic Stimulated EMG, XLIF®, Free-Run EMG, and Navigated Guidance modes, while selecting the lumbar region may automatically configure the options to allow selection of the Twitch Test, Basic, Difference, and Dynamic Stimulated EMG Tests, XLIF®, and Nerve Retractor modes. Default parameters associated with the various function modes may also depend on the profile selected, for example, the characteristics of the stimulation signal delivered by the system 10 may vary depending on the profile. By way of example, the stimulation signal utilized for the Stimulated EMG modes may be configured differently when a lumbar profile is selected versus when one of a thoracolumbar profile and a cervical profile.

As previously described above, each of the hardware components includes an identification tag that allows the control unit 12 to determine which devices are hooked up and ready for operation. In one embodiment, profiles may only be available for selection if the appropriate devices (e.g. proper electrode harness 80 and stimulation accessories) are connected and/or ready for operation. Alternatively, the software could bypass the startup screen and proceed directly to one of the functional modes based on the accessories and/or harnesses it knows are plugged in. The ability to select a profile based on standard parameters, and especially on customized preferences, may save significant time at the beginning of a procedure and provides for monitoring availability right from the start. Moving on from the startup screen, the software advances directly to an electrode test screen (for example, the electrode test screen of FIG. 15) and impedance tests, which are performed on every electrode as discussed above. When an acceptable impedance test has been completed, the system 10 is ready to begin monitoring and the software advances to a monitoring screen from which the neurophysiologic monitoring functions of the system 10 are performed.

The information displayed on the monitoring screen may include, but is not necessarily limited to, alpha-numeric and/or graphical information regarding any of the functional modes (e.g. SSEP Manual, SSEP Automatic, MEP Manual, MEP Automatic, Twitch Test, Basic Stimulated EMG, Dynamic Stimulated EMG, XLIF®, Free-Run EMG, and Navigated Guidance), attached accessories (e.g. stimulation probe 16, stimulation clip 18, tilt sensor 54), electrode harness or harnesses attached, impedance test results, myotome/EMG levels, stimulation levels, history reports, selected parameters, test results, etc. In one embodiment, set forth by way of example only, this information displayed on a main monitoring screen may include, but is not necessarily limited to the following components as set forth in Table 6.

TABLE 6

| Screen Component | Description |
| --- | --- |
| Patient Image/Electrode layout | An image of the human body or relevant portion thereof showing the electrode placement on the body, with labeled channel number tabs on each side (1-4 on the left and right). Left and right labels will show the patient orientation. The channel number tabs may be highlighted or colored depending on the specific function being performed. |
| Myotome & Level Names | A label to indicate the Myotome name and corresponding Spinal Level(s) associated with the channel of interest. |
| Test Menu | A hideable menu bar for selecting between the available functional modes. |
| Device Bar | A hideable bar displaying icons and/or names of devices connected to the patient module. |
| Display Area | Shows procedure-specific information including stimulation results. |
| Color Indication | Enhances stimulation results with a color display of green, yellow, or red corresponding to the relative safety level determined by the system. |
| Stimulation Bar | A graphical stimulation indicator depicting the present stimulation status (i.e. on or off and stimulation current level), as well as providing for starting and stopping stimulation |
| Event Bar | A hideable bar that shows the last up to a selected number of previous stimulation results, provides for annotation of results, and a chat dialogue box for communicating with remote participants. |
| EMG waveforms | EMG waveforms may be optionally displayed on screen along with the stimulation results. |

Figure 13:
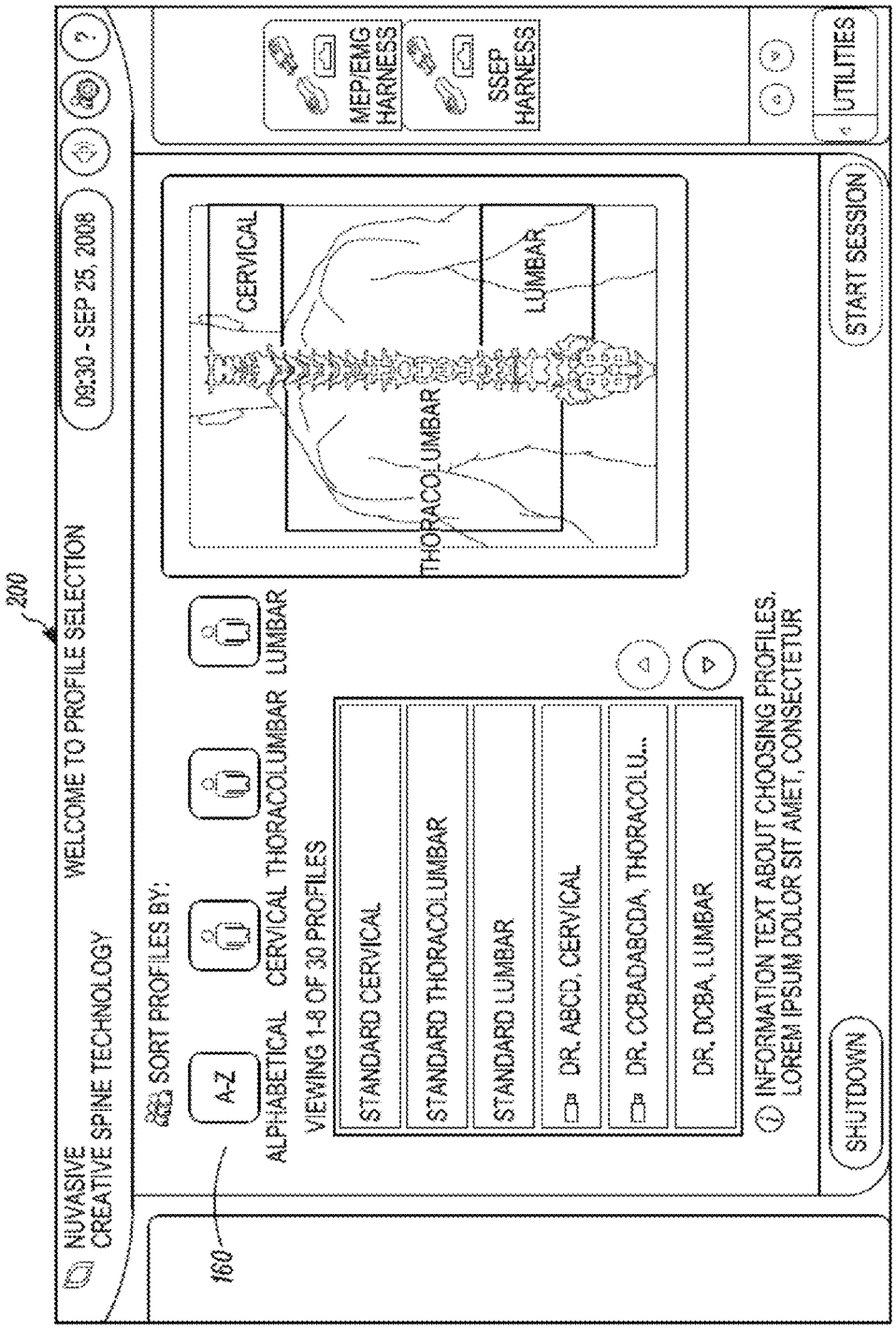
FIG. 13 is an exemplary screen display illustrating one embodiment of a general system setup screen forming part of the neurophysiology system of FIG. 1.
Figure 14:
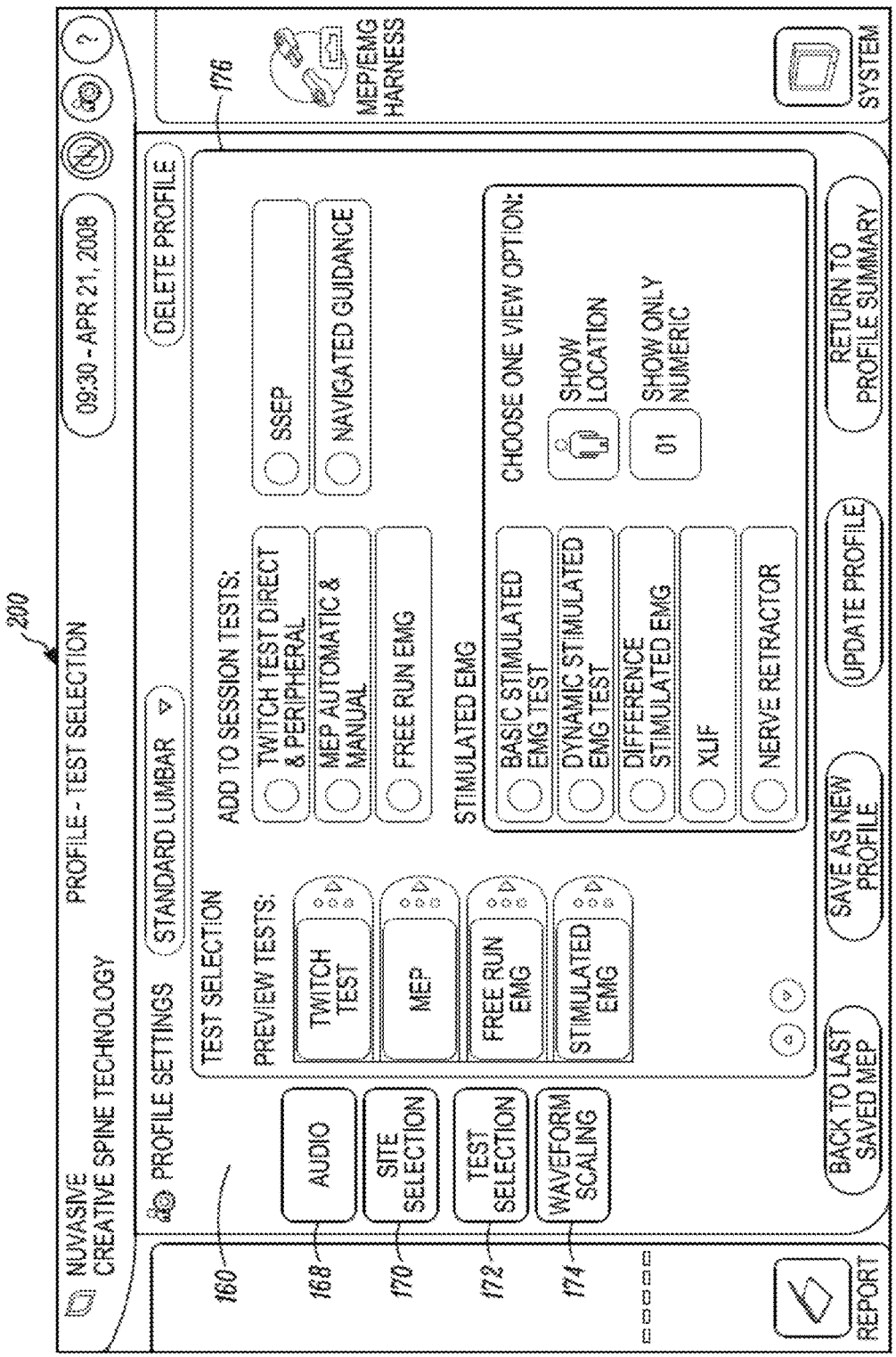
FIG. 14 is an exemplary screen display illustrating one embodiment of a detailed profile screen forming part of the neurophysiology system of FIG. 1.

From a profile setting window 160, illustrated by way of example only in FIG. 14, custom profiles can be created and saved. Beginning with one of the standard profiles, parameters may be altered by selecting one of the audio 168, site selection 170, test selection 172, and waveform scaling 174 buttons and making the changes until the desired parameters are set. By way of example only, profiles may be generated and saved for particular procedures (e.g. ACDF, XLIF®, and Decompression), particular individuals, and combinations thereof. Clicking on each button will display the parameter options specific to the selected button in a parameter window 176. The parameter options for the Test Selection Window are illustrated by way of example in FIG. 14. By way of example only, by selecting the Test Selection button, session tests may be added and viewing options may be changed. From within the test selection area, function-specific parameters for all available test functions (based on site selection, available devices, etc.) may be accessed and set according to need. One option that is available for multiple functions under the test selection button is the ability to select from three different viewing options. The user may choose to see results displayed in numeric form, on a body panel, and on a label that reflects the labels associated with each electrode, or any combination of the three. The user may also choose to see the actual waveforms. Selecting the Waveform Scaling button 174 allows the user to adjust the scale on which waveforms are displayed. By selecting the audio button 168 both the system audio and Free-Run audio may be adjusted. Selecting the site selection button 170 allows the opportunity to change from the site selected initially. Adjusting the site selection of the profile may alter the options available. By way of example, if the user changes the site selection from cervical to lumbar, the MEP function may no longer be selectable as an option. FIG. 13 is an example of a site selection screen. FIGS. 16-25 illustrate examples of the test selection tab for each of the test functions (e.g. SSEP Manual, SSEP Automatic, MEP Manual, MEP Automatic, Twitch Test, Basic Stimulated EMG, Dynamic Stimulated EMG, XLIF®, Free-Run EMG, and Navigated Guidance). Profiles may be saved directly on the control unit 12 or they may be saved to a portable memory device, or uploaded onto a web-server.

Figure 15:
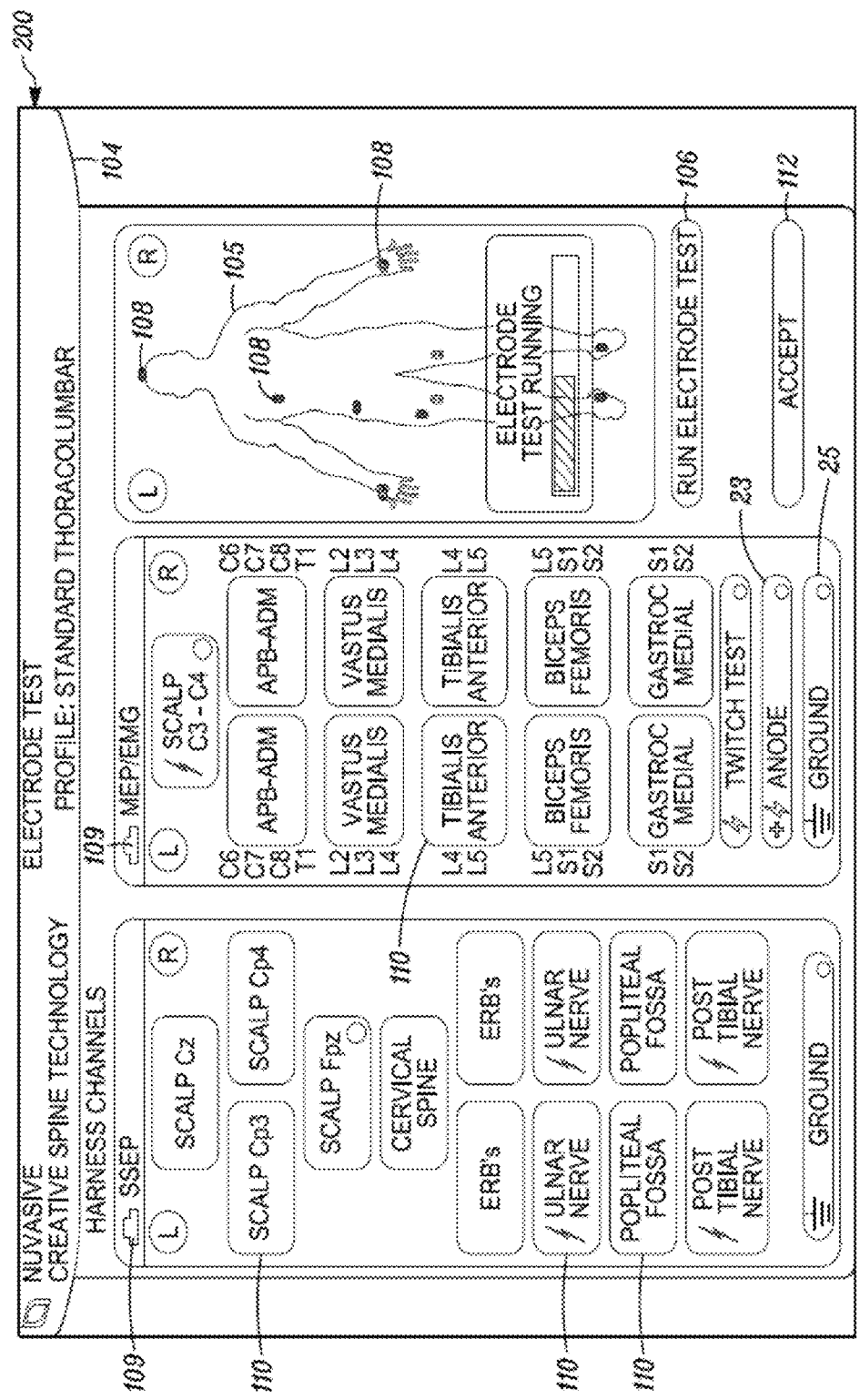
FIG. 15 is an exemplary screen display with features of an electrode test as implemented in one embodiment of an electrode test screen forming part of the neurophysiology system of FIG. 1.

Various features of the monitoring screen 200 of the GUI will now be described. The patient module 14 is configured such that the neurophysiology system 10 may conduct an impedance test under the direction of the control unit 12 of all electrodes once the system is set up and the electrode harness is connected and applied to the patient. After choosing the appropriate spinal site upon program startup (described below), the user is automatically directed to an electrode test. FIG. 15 illustrates, by way of example only, the features of the electrode test by graphical implementations of electrode test screens according to example embodiments of the GUI. The electrode test screen 104 includes a human figure graphic 105 with electrode position indicators 108. A harness indicator 109 displays the harness or harnesses 80 that are connected to the patient module 14. For each electrode on the harness or harnesses 80 in use, including the common 25 and anode 23 electrodes, there is a corresponding channel button 110. Preferably, the common 25 and anode 23 electrodes may be independently checked for acceptable impedance. To accomplish this, the anode 23 and common 25 are both provided as dual electrodes. At least one of the anode leads on the anode electrode is reversible. During the impedance check the reversible anode lead switches to a cathode such that the impedance between the leads can be measured. When the impedance test is complete the reversible lead switches back to an anode. The channel button 110 may be labeled with the muscle name or coverage area of the corresponding electrode. Stimulation electrodes may be denoted with a symbol or other indicator, such as by way of example only, a lightning bolt in order to distinguish the recording and stimulation electrodes. Selecting a channel button 110 will disable the associated channel. Disabled channels will not be tested for impedance and they will not be monitored for responses or errors unless reactivated (e.g. by again selecting the corresponding channel button 110). Upon selection of a start button 106 (entitled "Run Electrode Test"), the system 10 tests each electrode individually to determine the impedance value. If the impedance is determined to be within acceptable limits, the channel button 110 and corresponding electrode depiction on the human figure 108 turn green. If the impedance value for any electrode is not determined to be acceptable, the associated channel button 110 and electrode depiction turn red, alerting the user. Once the test is complete, selecting the Accept button 112 will open the main monitoring screen of system 10.

The functions performed by the neurophysiology system 10 may include, but are not necessarily limited to, the Twitch Test, Free-run EMG, Basic Stimulated EMG, Dynamic Stimulated EMG, XLIF®, Nerve Retractor, MEP Manual, MEP Automatic, and SSEP Manual, SSEP Automatic, and Navigated Guidance modes, all of which will be described briefly below. The Twitch Test mode is designed to assess the neuromuscular pathway via the so-called "train-of-four test" to ensure the neuromuscular pathway is free from muscle relaxants prior to performing neurophysiology-based testing, such as bone integrity (e.g. pedicle) testing, nerve detection, and nerve retraction. This is described in greater detail within PCT Patent App. No. PCT/US2005/036089, entitled "System and Methods for Assessing the Neuromuscular Pathway Prior to Nerve Testing," filed Oct. 7, 2005, the entire contents of which are hereby incorporated by reference as if set forth fully herein. The Basic Stimulated EMG Dynamic Stimulated EMG tests are designed to assess the integrity of bone (e.g. pedicle) during all aspects of pilot hole formation (e.g., via an awl), pilot hole preparation (e.g. via a tap), and screw introduction (during and after). These modes are described in greater detail in PCT Patent App. No. PCT/US2002/035047 entitled "System and Methods for Performing Percutaneous Pedicle Integrity Assessments," filed on Oct. 30, 2002, and PCT Patent App. No. PCT/US2004/025550, entitled "System and Methods for Performing Dynamic Pedicle Integrity Assessments," filed on Aug. 5, 2004, the entire contents of which are both hereby incorporated by reference as if set forth fully herein. The XLIF® mode is designed to detect the presence of nerves during the use of the various surgical access instruments of the neurophysiology system 10, including the pedicle access needle 26, k-wire 42, dilator 44, and retractor assembly 70. This mode is described in greater detail within PCT Patent App. No. PCT/US2002/022247, entitled "System and Methods for Determining Nerve Proximity, Direction, and Pathology During Surgery," filed on Jul. 11, 2002, the entire contents of which is hereby incorporated by reference as if set forth fully herein. The Nerve Retractor mode is designed to assess the health or pathology of a nerve before, during, and after retraction of the nerve during a surgical procedure. This mode is described in greater detail within PCT Patent App. No. PCT/US2002/030617, entitled "System and Methods for Performing Surgical Procedures and Assessments," filed on Sep. 25, 2002, the entire contents of which are hereby incorporated by reference as if set forth fully herein. The MEP Auto and MEP Manual modes are designed to test the motor pathway to detect potential damage to the spinal cord by stimulating the motor cortex in the brain and recording the resulting EMG response of various muscles in the upper and lower extremities. The SSEP function is designed to test the sensory pathway to detect potential damage to the spinal cord by stimulating peripheral nerves inferior to the target spinal level and recording the action potential from sensors superior to the spinal level. The MEP Auto, MEP manual, and SSEP modes are described in greater detail within PCT Patent App. No. PCT/US2006/003966, entitled "System and Methods for Performing Neurophysiologic Assessments During Spine Surgery," filed on Feb. 2, 2006, the entire contents of which is hereby incorporated by reference as if set forth fully herein. The SSEP Auto and SSEP manual modes are described in greater detail within PCT Patent App. No. PCT/US2009/005650, entitled "Neurophysiologic Monitoring System and Related Methods," filed on Oct. 15, 2009, the entire contents of which is hereby incorporated by reference as if set forth fully herein. The Navigated Guidance function is designed to facilitate the safe and reproducible use of surgical instruments and/or implants by providing the ability to determine the optimal or desired trajectory for surgical instruments and/or implants and monitor the trajectory of surgical instruments and/or implants during surgery. This mode is described in greater detail within PCT Patent App.

No. PCT/US2007/011962, entitled "Surgical Trajectory Monitoring System and Related Methods," filed on Jul. 30, 2007, the entire contents of which are incorporated herein by reference as if set forth fully herein. These functions will be explained now in brief detail.

Figure 16:
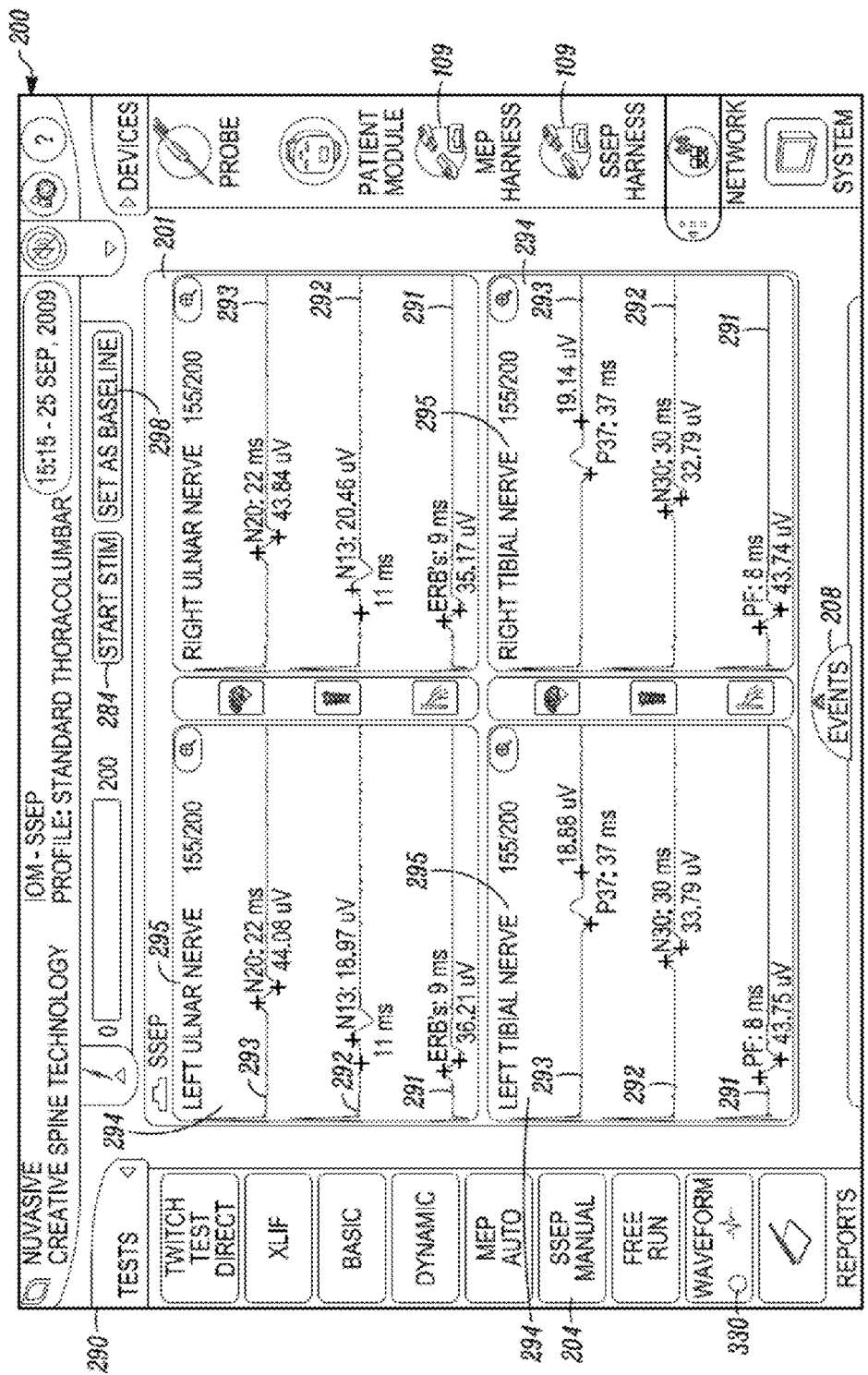
FIG. 16 is an exemplary screen display of a Manual SSEP monitoring screen forming part of the neurophysiology system of FIG. 1.

The neurophysiology system 10 performs assessments of spinal cord health using one or more of MEP Auto, MEP Manual, SSEP Auto, and SSEP Manual modes. FIG. 16 depicts an exemplary screen display for Manual mode of the SSEP monitoring function. A mode indicator tab 290 on the test menu 204 indicates that "SSEP Manual" is the selected mode. The center result area 201 is divided into four sub areas or channel windows 294, each one dedicated to displaying the signal response waveforms for one of the stimulation nerve sites. In the example shown, the system 10 displays the signal response waveforms associated with the left ulnar nerve, right ulnar nerve, left tibial nerve, and right tibial nerve. For each stimulated nerve site, the system 10 displays three signal response waveforms, representing the measurements made at three different recording sites. By way of example only, the three recording sites are a peripheral 291 (from a peripheral nerve proximal to the stimulation nerve), subcortical 292 (spine), and cortical 293 (scalp). It will be appreciated that SSEP stimulation may be applied to any number of peripheral sensory nerves and the recording sites may be located anywhere along the nervous system superior to the spinal level at risk during the procedure. Each nerve stimulation site includes a channel window 294. Provided in the channel window 294 is information including the nerve stimulation site 295, waveforms, and associated recording locations 291-293.

During SSEP mode, a single waveform response is generated for each stimulation signal. The stimulation signal is comprised of a predefined number of stimulation pulses firing at the selected stimulation frequency. By way of example only, the stimulation signal may include 300 pulses at a frequency of 4.1 Hz. The waveforms displayed by the system 10 represent an averaging of the 300 responses detected.

Figure 17:
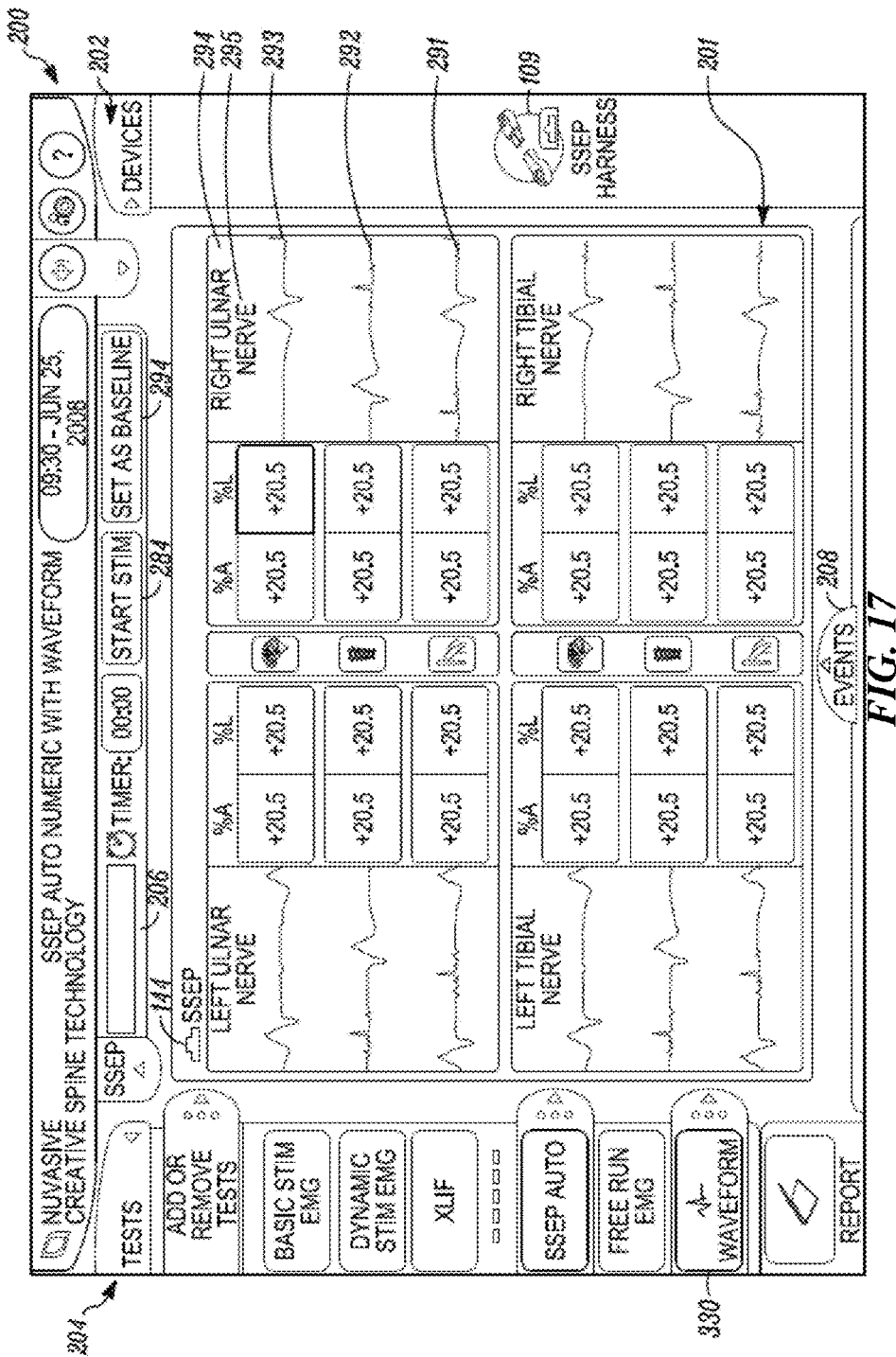
FIG. 17 is an exemplary screen display of an Automatic SSEP monitoring screen forming part of the neurophysiology system of FIG. 1.

In the Automatic SSEP mode, as shown, by way of example only in FIG. 17, the operator may simply select a stimulation current for each stimulation site and the system 10 monitors the health of the spinal cord by measuring the amplitude at the recording site of the response waveform when it reaches the recording sites and the latency period (the time the signal takes to travel from the stimulation site to the recording site). The system 10 compares amplitude measurements to a previously recorded baseline amplitude or the preceding measurement, and the difference between either the current measurement and the baseline or the current measurement and the preceding measurement is viewed on the display 26. Similarly, latency measurements are compared to a previously recorded baseline latency or the preceding measurement and the difference value is shown on the display 26. A decrease in amplitude or an increase in latency may alert the surgeon to potential damage in the spinal cord and corrective measures may be taken to avoid or mitigate such damage.

In addition to alerting the operator to any changes in the amplitude and/or latency of the SSEP signal response, it is further contemplated that the neurophysiology system 10 may assess the data from all the recording sites to interpret possible causes for changes in the SSEP response. The neurophysiology system 10 has pre-defined optimum ranges for each amplitude and latency cursor. The SSEP Automatic software program receives information as to the latency and amplitudes within the vicinity of these points (within some outer limits), and places the cursors in the high (peak) and low (trough) points of the waveform. Based on that information, the program may suggest potential reasons for the deviation. Furthermore, it may suggest potential actions to be taken to avoid danger. Table 7 illustrates the SSEP interpretation program in greater detail. It is still further contemplated that the neurophysiology system 10 may be communicatively linked with other equipment in the operating room, such as for example, anesthesia monitoring equipment. Data from this other equipment may be considered by the program to generate more accuracy and or better suggestions.

TABLE 7

| Neurophysiologic Event | Audio-visual Alert (Color) | SSEP Expert Text |
| --- | --- | --- |
| Cortical amplitude decrease: 0-25% from baseline | Green | No Warning |
| Cortical amplitude decrease: 26-49% from baseline | Yellow | "Some anesthetic agents may reduce the cortical response amplitude." |
| Cortical amplitude decrease: 50%-99% from baseline | Red | "Some anesthetic agents may reduce the cortical response amplitude." |
| Cortical amplitude decrease: 100% from baseline | Red | "Possible cortical ischemia." |
| Cortical latency increase: 0-5% from baseline | Green | No Warning |
| Cortical latency increase: 6-9% from baseline | Yellow | "Some anesthetic agents may increase the cortical response latency. Possible cortical ischemia." |
| Cortical latency increase: 10% or greater from baseline | Red | "Some anesthetic agents may increase the cortical response latency. Possible cortical ischemia." |
| Cortical response absent: | Red | "Some anesthetic agents may cause the cortical response to be absent. Possible cortical ischemia." |
| Subcortical amplitude decrease: 0%-25% from baseline | Green | No Warning |
| Subcortical amplitude decrease: 25%-49% from baseline | Yellow | "Possible muscle activity artifact. Possible cervical recording electrode issue." |
| Subcortical amplitude decrease: 50-99% from baseline or absent | Red | "Possible muscle activity artifact. Possible cervical recording issue." |
| 50% amplitude decrease, 10% latency increase in both cortical and subcortical responses, or absence in both cortical and subcortical responses: | Red | "Possible mechanical insult. Possible spinal cord ischemia." |

TABLE 7-continued

| Neurophysiologic Event | Audio-visual Alert (Color) | SSEP Expert Text |
|---|---|---|
| Peripheral amplitude decrease: greater than 50% or absent | Red | "Possible peripheral recording electrode issue." |
| Peripheral (Erb's Point) amplitude decrease: 0-25% from baseline | Green | No Warning (left or right) |
| Peripheral (Erb's Point) amplitude decrease: 26-49% from baseline | Yellow | "Possible peripheral recording electrode issue (Left Erb's Point)." "Possible peripheral recording electrode issue (Right Erb's Point)." |
| Peripheral (Erb's Point) amplitude decrease: 50%-100% from baseline | Red | "Possible peripheral recording electrode issue (Left Erb's Point)." "Possible peripheral recording electrode issue (Right Erb's Point)." |
| Peripheral (Popliteal Fossa) amplitude decrease: 0-25% from baseline | Green | No Warning (left or right) |
| Peripheral (Popliteal Fossa) amplitude decrease: 26-49% from baseline | Yellow | "Possible peripheral recording electrode issue (Left Popliteal Fossa)." "Possible peripheral recording electrode issue (Right Popliteal Fossa)." |
| Peripheral (Popliteal Fossa) amplitude decrease: 50%-100% from baseline | Red | "Possible peripheral recording electrode issue (Left Popliteal Fossa)." "Possible peripheral recording electrode issue (Right Popliteal Fossa)." |
| Peripheral (Erb's Point) latency increase: 0-5% from baseline | Green | No Warning (left or right) |
| Peripheral (Erb's Point) latency increase: 6-9% from baseline | Yellow | No Warning (left or right) |
| Peripheral (Erb's Point) latency increase: 10% or greater from baseline | Red | No Warning (left or right) |
| Peripheral (Popliteal Fossa) latency increase: 0-5% from baseline | Green | No Warning (left or right) |
| Peripheral (Popliteal Fossa) latency increase: 6-9% from baseline | Yellow | No Warning (left or right) |
| Peripheral (Popliteal Fossa) latency increase: 10% or greater from baseline | Red | No Warning (left or right) |
| Peripheral (Popliteal Fossa) and subcortical amplitude decrease: 0-25% from baseline | Green | "Possible muscle activity artifact. Possible cervical recording electrode issue." (left or right) |
| Peripheral (Popliteal Fossa) and subcortical amplitude decrease: 26%-100% from baseline | Yellow/ Red | "Possible cervical muscle activity artifact. Possible cervical recording electrode issue. Possible muscle activity artifact (posterior tibial nerve)." (left or right) |
| Peripheral (Erb's Point) and subcortical amplitude decrease: 0-25% from baseline | Green | "Possible muscle activity artifact. Possible cervical recording electrode issue." (left or right) |
| Peripheral (Erb's Point) and subcortical amplitude decrease: 26-99% from baseline | Yellow/Red | "Possible cervical muscle activity artifact. Possible cervical recording electrode issue. Possible muscle activity artifact (median nerve)." (left or right) |
| Decreased amplitude or absent response in all, peripheral (left Erb's point), subcortical, and cortical | Yellow/Red | "Possible stimulating electrode issue (left wrist)." |
| Decreased amplitude or absent in all, peripheral (right Erb's point), subcortical, and cortical | Yellow/Red | "Possible stimulating electrode issue (right wrist)." |
| Decreased amplitude or absent response in all peripheral (left Popliteal Fossa), subcortical, and cortical | Yellow/Red | "Possible stimulating electrode issue (left ankle)." |
| Decreased amplitude or absent response in all peripheral (right Popliteal Fossa), subcortical, and cortical | Yellow/Red | Possible stimulating electrode issue (right ankle)." |
| Increased latency or decreased amplitude in all, peripheral, subcortical, and cortical | Yellow/Red | "Possible systemic change (hypotension, hypothermia, hyperthermia). Possible peripheral nerve ischemia." (left or right) (posterior tibial or ulnar nerve) |

Figure 26:
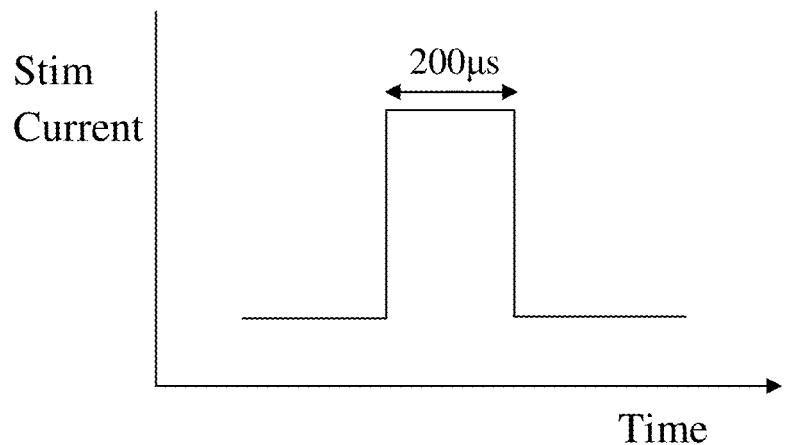
FIG. 26 is a graph illustrating a plot of a stimulation current signal comprising a train of pulses capable of producing a neuromuscular response (EMG) of the type shown in FIG. 27.
Figure 27:
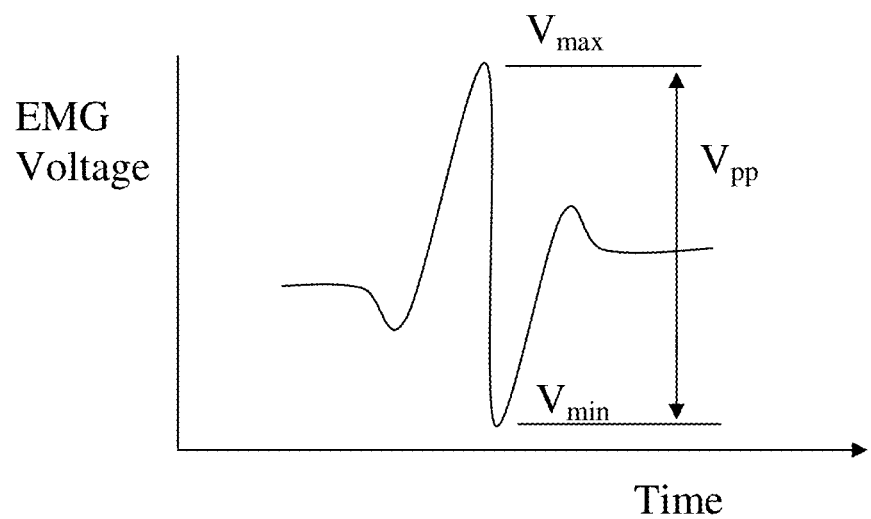
FIG. 27 is a graph illustrating a plot of the neuromuscular response of a given myotome over time based on a stimulation signal (such as shown in FIG. 26) transmitted to a nerve bundle coupled to the given myotome.
Figure 28:
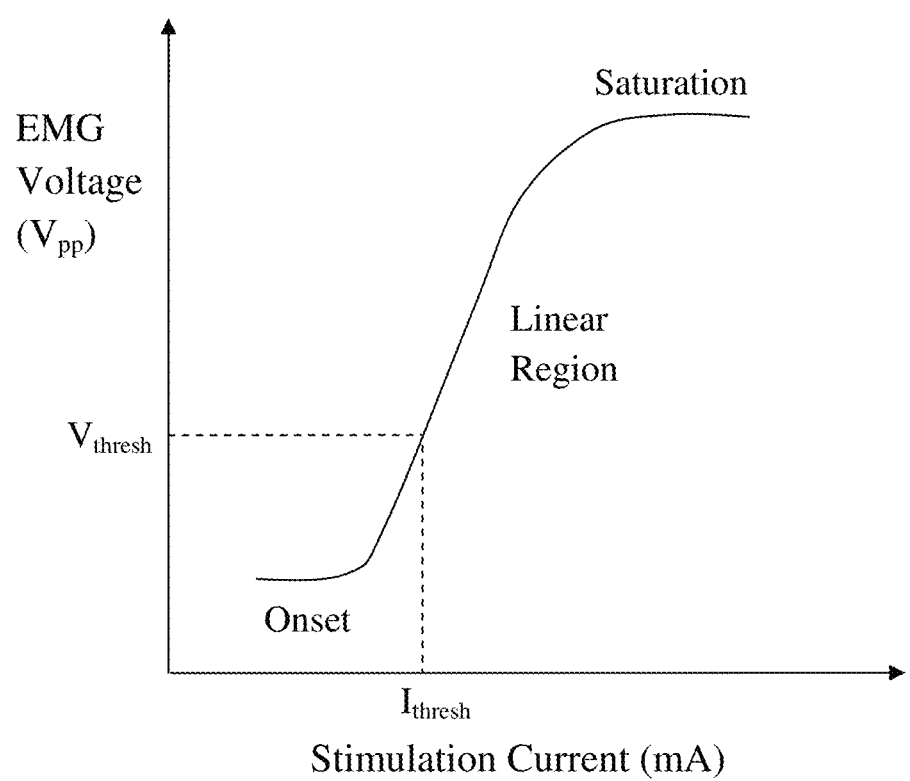
FIG. 28 is a graph illustrating a plot of EMG response peak-to-peak ($V_{pp}$) for each given stimulation current level ($I_{Stim}$) forming a stimulation current pulse according to the present invention (otherwise known as a "recruitment curve")

The neuromonitoring functionality of the surgical system 10 (except SSEP, which as discussed in greater detail in PCT Patent App. No. PCT/US2009/005650, entitled "Neurophysiologic Monitoring System and Related Methods, filed on Oct. 15, 2009) is based on assessing the evoked response of the various muscle myotomes monitored by the surgical system 10 in relation to a stimulation signal transmitted by the system 10. This is best shown in FIGS. 26-28, wherein FIG. 28 illustrates the resulting EMG of a monitored myotome in response to each pulse of the stimulation shown in FIG. 26.

A basic premise underlying the methods employed by the system 10 is that neurons and nerves have characteristic threshold current levels ($I_{Thresh}$) at which they will depolarize, resulting in detectable muscle activity. Below this threshold current, stimulation signals will not evoke a significant EMG response. Each EMG response can be characterized by a peak-to-peak voltage of $V_{pp}=V_{max}-V_{min}$ shown in FIG. 27. Once the stimulation threshold ($I_{Thresh}$) is reached, the evoked response is reproducible and increases with increasing stimulation until saturation is reached as shown in FIG. 28. This is known as a "recruitment curve." In one embodiment, a significant EMG response is defined as having a $V_{pp}$ of approximately 100 μV. The lowest signal current that evokes this threshold voltage ($V_{Thresh}$) is called $I_{Thresh}$. $I_{Thresh}$ increases as the degree of electrical communication between a stimulation signal and a nerve decreases and conversely, $I_{Thresh}$ decreases as the electrical communication increases between the nerve and stimulation pulse. Thus monitoring $I_{Thresh}$ provides valuable information for different nerve monitoring functions, including, but not necessarily limited to, motor evoked potential testing, pedicle screw testing, nerve proximity monitoring, and nerve pathology monitoring. Armed with the useful information conveyed by $I_{Thresh}$, the surgeon may detect a problem or potential problem and then act to avoid and/or mitigate the problem. Techniques for quickly determining $I_{Thresh}$ are described below.

Figure 18:
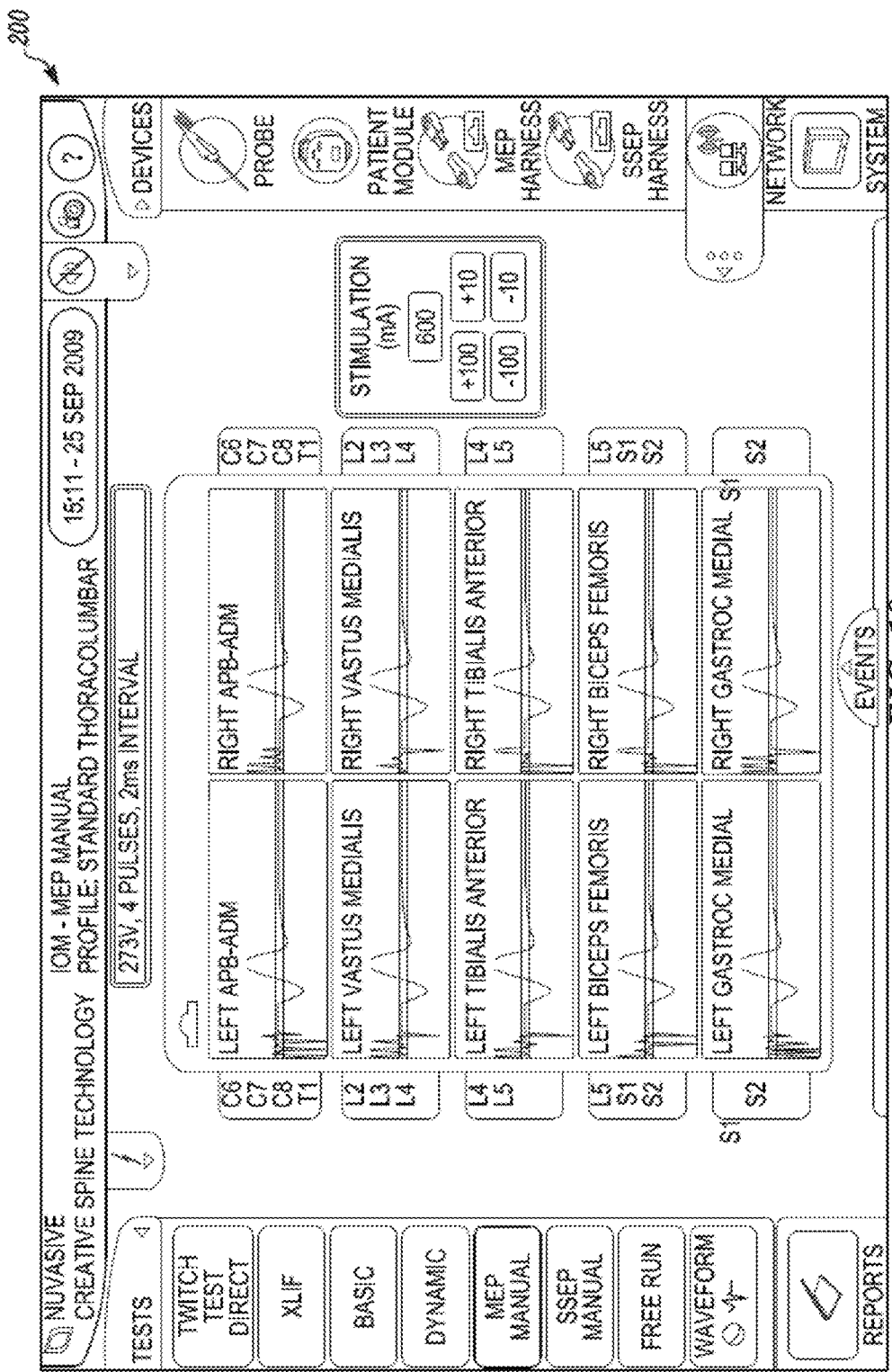
FIG. 18 is an exemplary screen display of a Manual MEP monitoring screen forming part of the neurophysiology system of FIG. 1.
Figure 19:
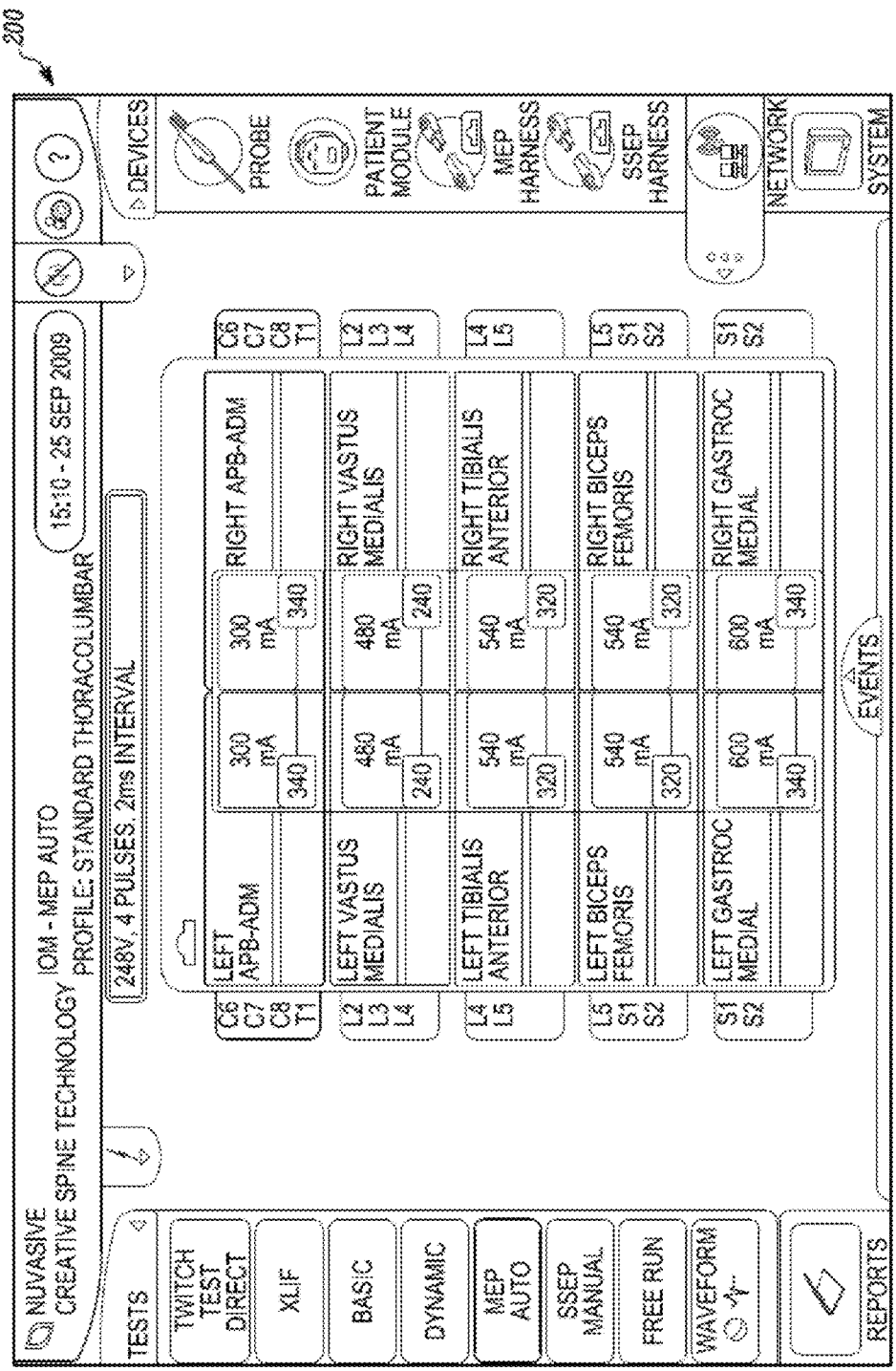
FIG. 19 is an exemplary screen display of an Automatic MEP monitoring screen forming part of the neurophysiology system of FIG. 1.

In MEP modes, stimulation signals are delivered to the motor cortex via patient module 14 and resulting responses are detected from various muscles in the upper and lower extremities. An increase in $I_{Thresh}$ from an earlier test to a later test may indicate a degradation of spinal cord function. Likewise, the absence of a significant EMG response to a given $I_{Stim}$ on a channel that had previously reported a significant response to the same or lesser $I_{Stim}$ is also indicative of a degradation in spinal cord function. These indicators are detected by the system in the MEP modes and reported to the surgeon. In MEP Auto mode the system determines the $I_{Thresh}$ baseline for each channel corresponding to the various monitored muscles, preferably early in the procedure, using the multi-channel algorithm described. Throughout the procedure subsequent tests may be conducted to again determine $I_{Thresh}$ for each channel. The difference between the resulting $I_{Thresh}$ values and the corresponding baseline are computed by the system 10 and compared against predetermined "safe" and "unsafe" difference values. The $I_{Thresh}$, baseline, and difference values are displayed to the user, along with any other indicia of the safety level determined (such as a red, yellow, green color code), on the display 34, as illustrated in FIG. 19. In MEP Manual mode, the user selects the stimulation current level and the system reports whether or not the stimulation signal evokes a significant response on each channel. Stimulation results may be shown on the display 34 in the form of "YES" and "NO" responses, or other equivalent indicia, as depicted in FIG. 18. Using either mode the surgeon may thus be alerted to potential complications with the spinal cord and any corrective actions deemed necessary may be undertaken at the discretion of the surgeon.

Figure 20:
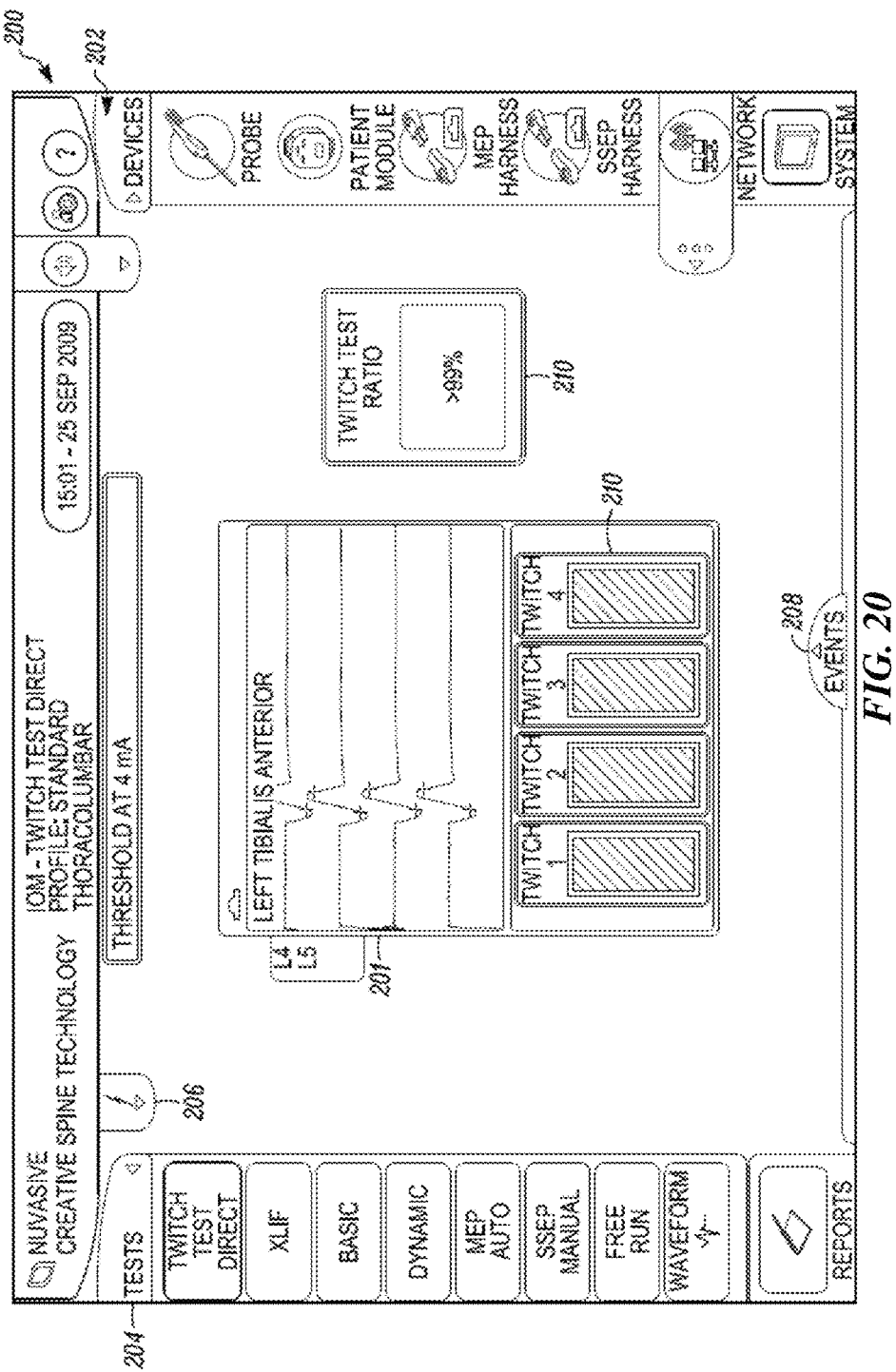
FIG. 20 is an exemplary screen display of a Twitch Test monitoring screen forming part of the neurophysiology system of FIG. 1.

The neurophysiology system 10 performs neuromuscular pathway (NMP) assessments, via Twitch Test mode, by electrically stimulating a peripheral nerve (preferably the peroneal nerve for lumbar and thoracolumbar applications and the median nerve for cervical applications) via stimulation electrodes 22 contained in the applicable electrode harness and placed on the skin over the nerve or by direct stimulation of a spinal nerve using a surgical accessory such as the probe 116. Evoked responses from the muscles innervated by the stimulated nerve are detected and recorded, the results of which are analyzed and a relationship between at least two responses or a stimulation signal and a response is identified. The identified relationship provides an indication of the current state of the NMP. The identified relationship may include, but is not necessarily limited to, one or more of magnitude ratios between multiple evoked responses and the presence or absence of an evoked response relative to a given stimulation signal or signals. With reference to FIG. 20, details of the test indicating the state of the NMP and the relative safety of continuing on with nerve testing are conveyed to the surgeon via GUI display 34. On the monitoring screen 200 utilized by the various functions performed by the system 10, function specific data is displayed in a center result area 201. The results may be shown as a numeric value 210, a highlighted label corresponding to the electrode labels 86, or (in the case of twitch test only) a bar graph of the stimulation results. On one side of center result area 201 is a collapsible device menu 202. The device menu displays a graphic representation of each device connected to the patient module 14. Opposite the device menu 202 there is a collapsible test menu 204. The test menu 204 highlights each test that is available under the operable setup profile and may be used to navigate between functions. A collapsible stimulation bar 206 indicates the current stimulation status and provides start and stop stimulation buttons (not shown) to activate and control stimulation. The collapsible event bar 208 stores all the stimulation test results obtained throughout a procedure. Clicking on a particular event will open a note box and annotations may be entered and saved with the response, for later inclusion in a procedure report. The event bar 208 also houses a chat box feature when the system 10 is connected to a remote monitoring system as described above. Within the result area 202 the twitch test specific results may be displayed.

It should be appreciated that while FIG. 20 depicts the monitoring screen 200 while the selected function is the Twitch Test, the features of monitoring screen 200 apply equally to all the functions. Result-specific data is displayed in a center result area 201. A large color saturated numeric value (not shown) is used to show the threshold result. Three different options are provided for showing the stimulation response level. First, the user can view the waveform. Second, a likeness of the color coded electrode harness label 86 may be shown on the display. Third, the color coded label 212 may be integrated with a body image. On one side of center result area 201 there is a collapsible device menu 202. The device menu displays a graphic representation of each device connected to the patient module 14. If a device is selected from the device menu 202, an impedance test may be initiated. Opposite the device menu 202 there is a collapsible test menu 204. The test menu 204 highlights each test that is available under the operable setup profile and may be used to navigate between functions. A collapsible stimulation bar 206 indicates the current stimulation status and provides start and stop stimulation buttons (not shown) to activate and control stimulation. The collapsible event bar 208 stores all the stimulation test results obtained throughout a procedure so that the user may review the entire case history from the monitoring screen. Clicking on a particular event will open a note box and annotations may be entered and saved with the response, for later inclusion in a procedure report chronicling all nerve monitoring functions conducted during the procedure as well as the results of nerve monitoring. In one embodiment the report may be printed immediately from one or more printers located in the operating room or copied to any of a variety of memory devices known in the prior art, such as, by way of example only, a floppy disk, and/or USB memory stick. The system 10 may generate either a full report or a summary report depending on the particular needs of the user. In one embodiment, the identifiers used to identify the surgical accessories to the patient module may also be encoded to identify their lot number or other identifying information. As soon as the accessory is identified, the lot number may be automatically added to the report. Alternatively, hand held scanners can be provided and linked to the control unit 12 or patient module 14. The accessory packaging may be scanned and again the information may go directly to the procedure report. The event bar 208 also houses a chat box feature when the system 10 is connected to a remote monitoring system to allow a user in the operating room to contemporaneously communicate with a person performing the associated neuromonitoring in a remote location.

The neurophysiology system 10 may test the integrity of pedicle holes (during and/or after formation) and/or screws (during and/or after introduction) via the Basic Stimulation EMG and Dynamic Stimulation EMG tests. To perform the Basic Stimulation EMG a test probe 116 is placed in the screw hole prior to screw insertion or placed on the installed screw head and a stimulation signal is applied. The insulating character of bone will prevent the stimulation current, up to a certain amplitude, from communicating with the nerve, thus resulting in a relatively high $I_{Thresh}$, as determined via the basic threshold hunting algorithm described below. However, in the event the pedicle wall has been breached by the screw or tap, the current density in the breach area will increase to the point that the stimulation current will pass through to the adjacent nerve roots and they will depolarize at a lower stimulation current, thus $I_{Thresh}$ will be relatively low. The system described herein may exploit this knowledge to inform the practitioner of the current $I_{Thresh}$ of the tested screw to determine if the pilot hole or screw has breached the pedicle wall.

In Dynamic Stim EMG mode, test probe 116 may be replaced with a clip 18 which may be utilized to couple a surgical tool, such as for example, a tap member 28 or a pedicle access needle 26, to the neurophysiology system 10. In this manner, a stimulation signal may be passed through the surgical tool and pedicle integrity testing can be performed while the tool is in use. Thus, testing may be performed during pilot hole formation by coupling the access needle 26 to the neurophysiology system 10, and during pilot hole preparation by coupling the tap 28 to the system 10. Likewise, by coupling a pedicle screw to the neurophysiology system 10 (such as via pedicle screw instrumentation), integrity testing may be performed during screw introduction.

In both Basic Stimulation EMG mode and Dynamic Stimulation EMG mode, the signal characteristics used for testing in the lumbar testing may not be effective when monitoring in the thoracic and/or cervical levels because of the proximity of the spinal cord to thoracic and cervical pedicles. Whereas a breach formed in a pedicle of the lumbar spine results in stimulation being applied to a nerve root, a breach in a thoracic or cervical pedicle may result in stimulation of the spinal cord instead, but the spinal cord may not respond to a stimulation signal the same way the nerve root would. To account for this, the surgical system 10 is equipped to deliver stimulation signals having different characteristics based on the region selected. By way of example only, when the lumbar region is selected, stimulation signals for the stimulated EMG modes comprise single pulse signals. On the other hand, when the thoracic and cervical regions are selected the stimulation signals may be configured as multipulse signals.

Figure 21:
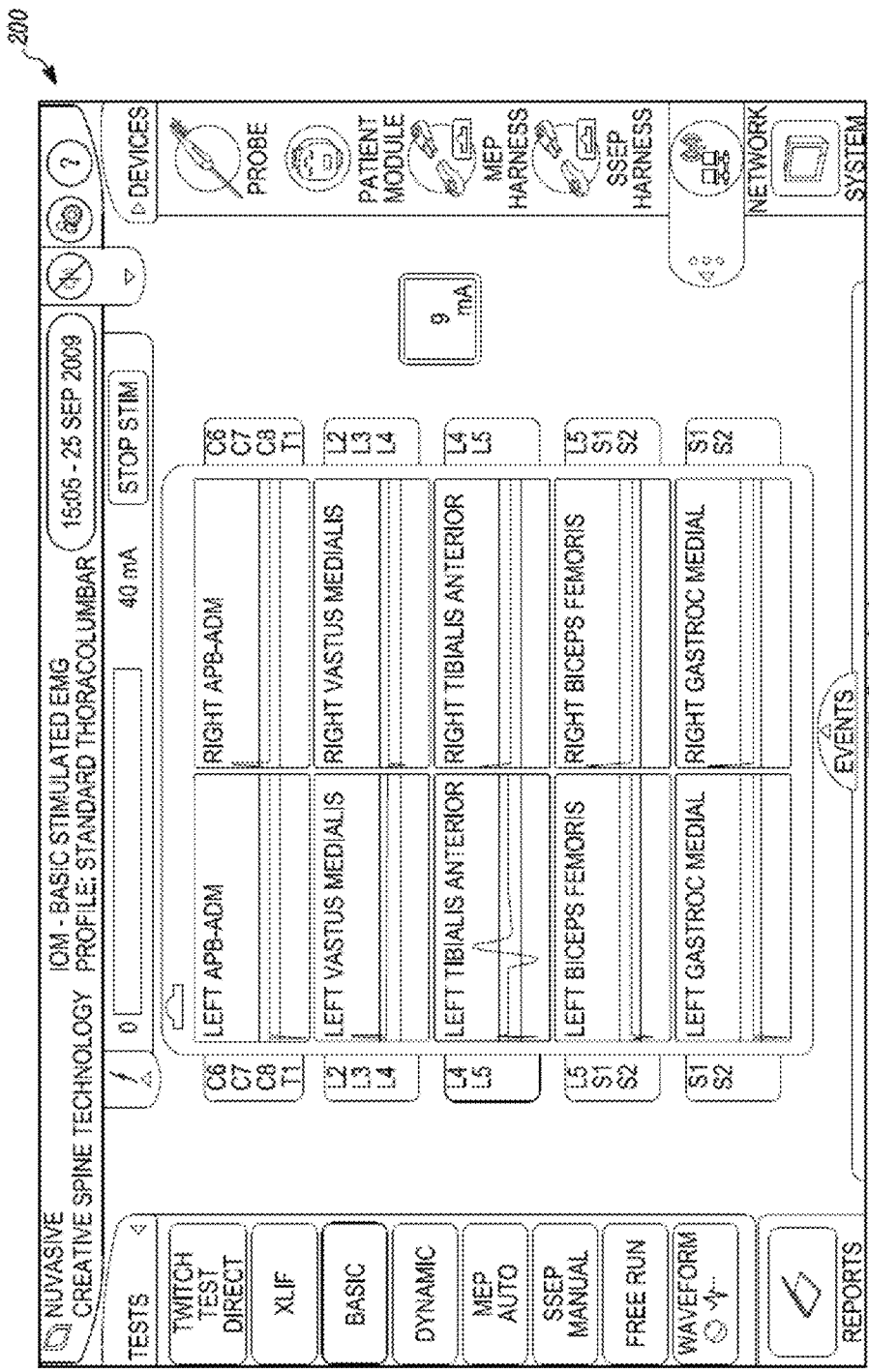
FIG. 21 is an exemplary screen display of a Basic Stimulation EMG monitoring screen forming part of the neurophysiology system of FIG. 1.
Figure 22:
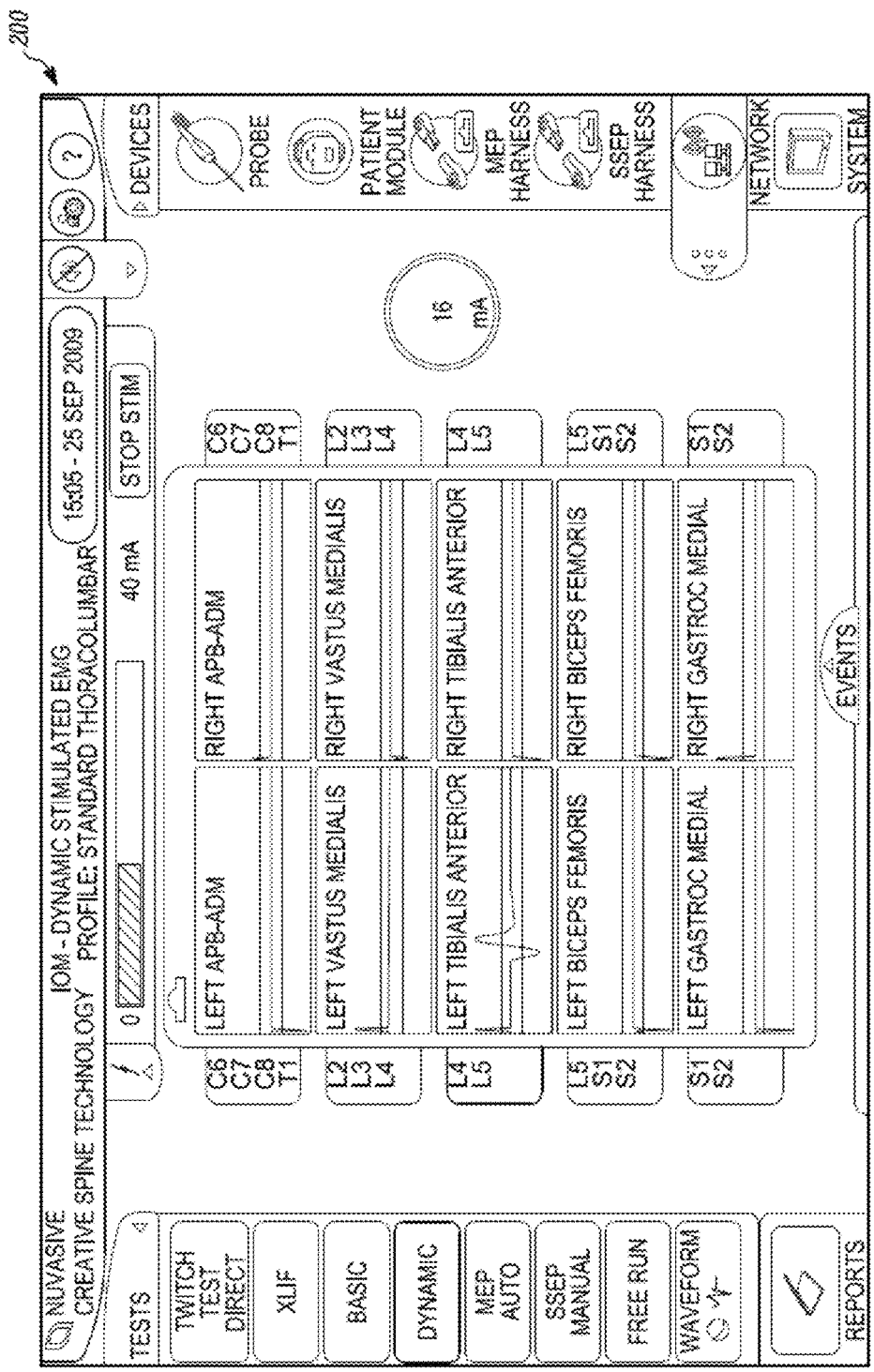
FIG. 22 is an exemplary screen display of a Dynamic Stimulation EMG monitoring screen forming part of the neurophysiology system of FIG. 1.

Stimulation results (including but not necessarily limited to at least one of the numerical $I_{Thresh}$ value and color coded safety level indication) and other relevant data are conveyed to the user on at least main display 34, as illustrated in FIGS. 21 and 22. FIG. 21 illustrates the monitoring screen 200 with the Basic Stimulation EMG test selected. FIG. 22 illustrates the monitoring screen 200 with the Dynamic Stimulation EMG test selected. In one embodiment of the various screw test functions (e.g. Basic and Dynamic), a green level corresponds to a threshold range of greater than 10 milliamps (mA), a yellow level corresponds to a stimulation threshold range of 7-10 mA, and a red level corresponds to a stimulation threshold range of 6 mA or below. EMG channel tabs may be selected via the touch screen display 26 to show the $I_{Thresh}$ of the corresponding nerves. Additionally, the EMG channel possessing the lowest $I_{Thresh}$ may be automatically highlighted and/or colored to clearly indicate this fact to the user.

Figure 23:
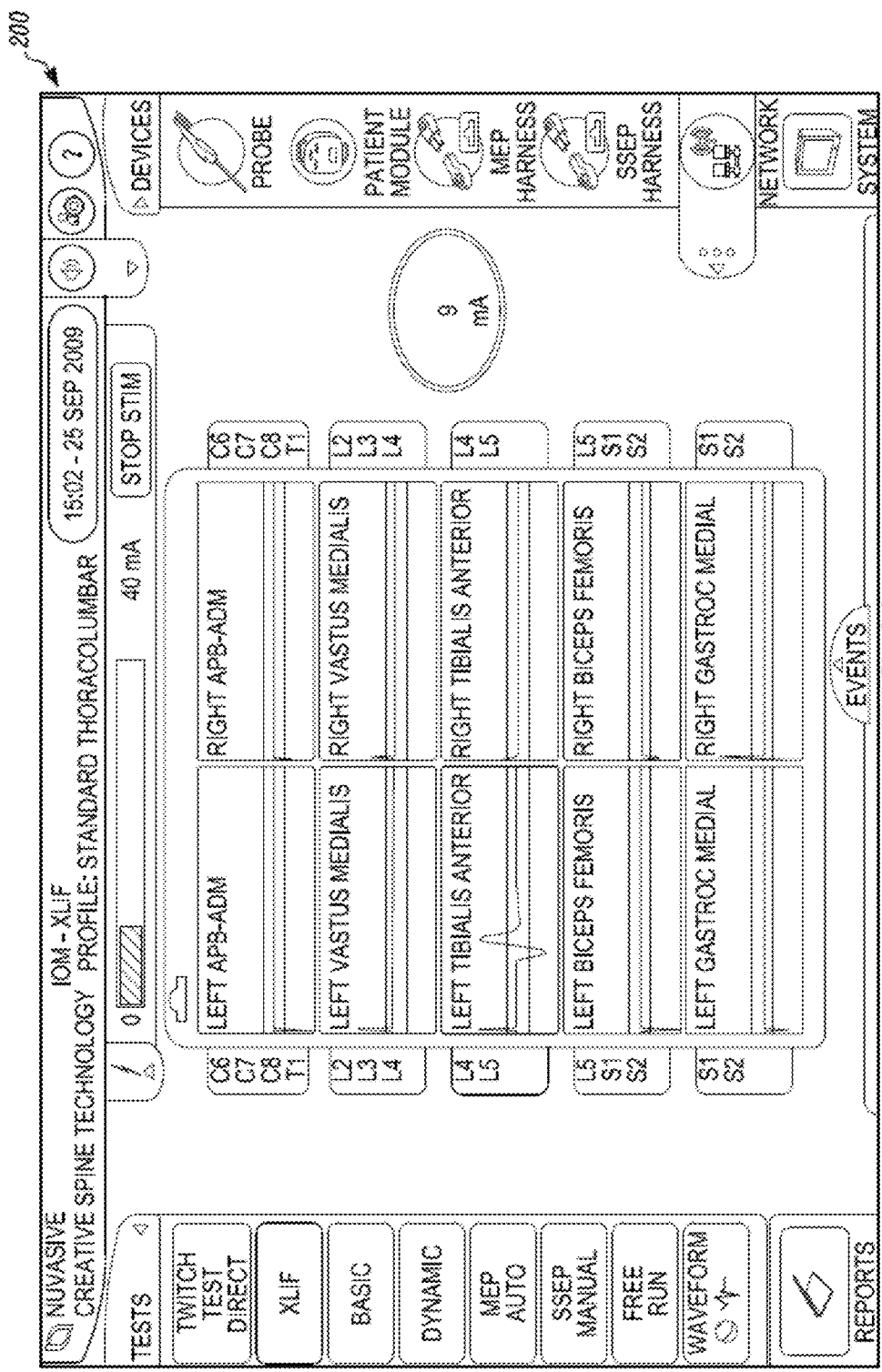
FIG. 23 is an exemplary screen display of a Nerve Surveillance EMG monitoring screen forming part of the neurophysiology system of FIG. 1.

The neurophysiology system 10 may perform nerve proximity testing, via the XLIF® mode, to ensure safe and reproducible access to surgical target sites. Using the surgical access components 26-32, the system 10 detects the existence of neural structures before, during, and after the establishment of an operative corridor through (or near) any of a variety of tissues having such neural structures which, if contacted or impinged, may otherwise result in neural impairment for the patient. The surgical access components 26-32 are designed to bluntly dissect the tissue between the patient's skin and the surgical target site. Dilators of increasing diameter, which are equipped with one or more stimulating electrodes, are advanced towards the target site until a sufficient operating corridor is established to advance retractor 32 to the target site. As the dilators are advanced to the target site electrical stimulation signals are emitted via the stimulation electrodes. The stimulation signal will stimulate nerves in close proximity to the stimulation electrode and the corresponding EMG response is monitored. As the stimulation electrode gets closer to the nerve, the stimulation current required to evoke a muscle response decreases because the resistance caused by human tissue will decrease, and it will take less current to cause nervous tissue to depolarize. $I_{Thresh}$ is calculated, using the basic threshold hunting algorithm described below, providing a measure of the communication between the stimulation signal and the nerve and thus giving a relative indication of the proximity between access components and nerves. An example of the monitoring screen 200 with XLIF® mode active is depicted in FIG. 23. In a preferred embodiment, a green or safe level corresponds to a stimulation threshold range of 10 mA or greater, a yellow level denotes a stimulation threshold range of 5-9 mA, and a red level denotes a stimulation threshold range of 4 mA or below.

Figure 24:
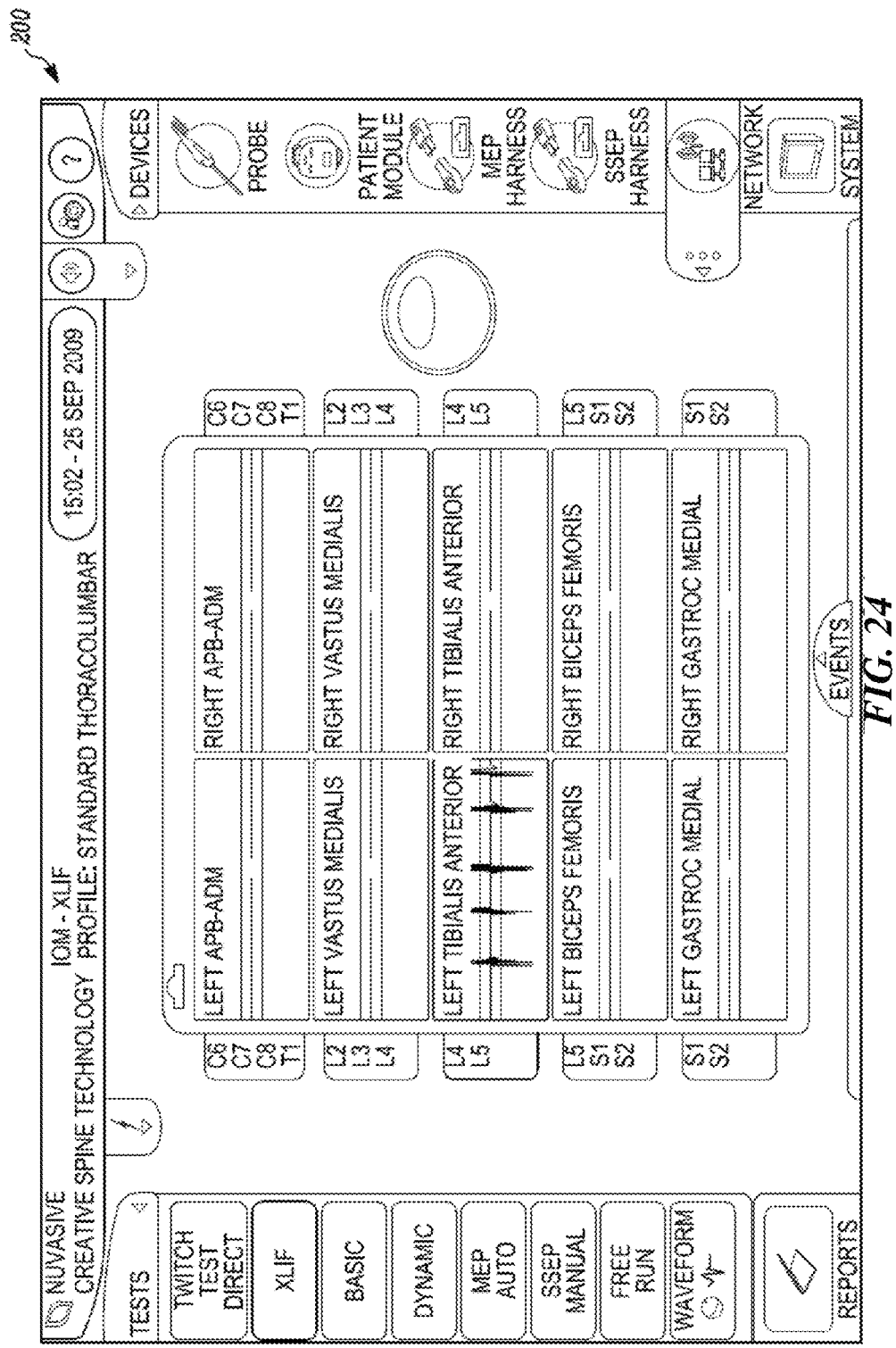
FIG. 24 is an exemplary screen display of a Free-Run EMG monitoring screen forming part of the neurophysiology system of FIG. 1.

The neurophysiology system 10 may also conduct free-run EMG monitoring while the system is in any of the above-described modes. Free-run EMG monitoring continuously listens for spontaneous muscle activity that may be indicative of potential danger to a nerve. The system 10 may automatically cycle into free-run monitoring after 5 seconds (by way of example only) of inactivity. Initiating a stimulation signal in the selected mode will interrupt the free-run monitoring until the system 10 has again been inactive for five seconds, at which time the free-run begins again. An example of the monitoring screen 200 with Free-run EMG active is depicted in FIG. 24.

The neurophysiology system 10 may also perform a navigated guidance function. The navigated guidance feature may be used by way of example only, to ensure safe and reproducible pedicle screw placement by monitoring the axial trajectory of surgical instruments used during pilot hole formation and/or screw insertion. Preferably, EMG monitoring may be performed simultaneously with the navigated guidance feature. To perform the navigated guidance, an angle-measuring device (hereafter "tilt sensor") 54 is connected to the patient module 14 via one of the accessory ports 62. The tilt sensor measures its angular orientation with respect to a reference axis (such as, for example, "vertical" or "gravity") and the control unit displays the measurements. Because the tilt sensor is attached to a surgical instrument, the angular orientation of the instrument may be determined as well, enabling the surgeon to position and maintain the instrument along a desired trajectory during use. In general, to orient and maintain the surgical instrument along a desired trajectory during pilot hole formation, the surgical instrument is advanced to the pedicle (through any of open, mini-open, or percutaneous access) while oriented in the zero-angle position. The instrument is then angulated in the sagittal plane until the proper cranial-caudal angle is reached. Maintaining the proper cranial-caudal angle, the surgical instrument may then be angulated in the transverse plane until the proper medial-lateral angle is attained. Once the control unit 12 indicates that both the medial-lateral and cranial caudal angles are matched correctly, the instrument may be advanced into the pedicle to form the pilot hole, monitoring the instrument's angular trajectory until the hole formation is complete.

Figure 25:
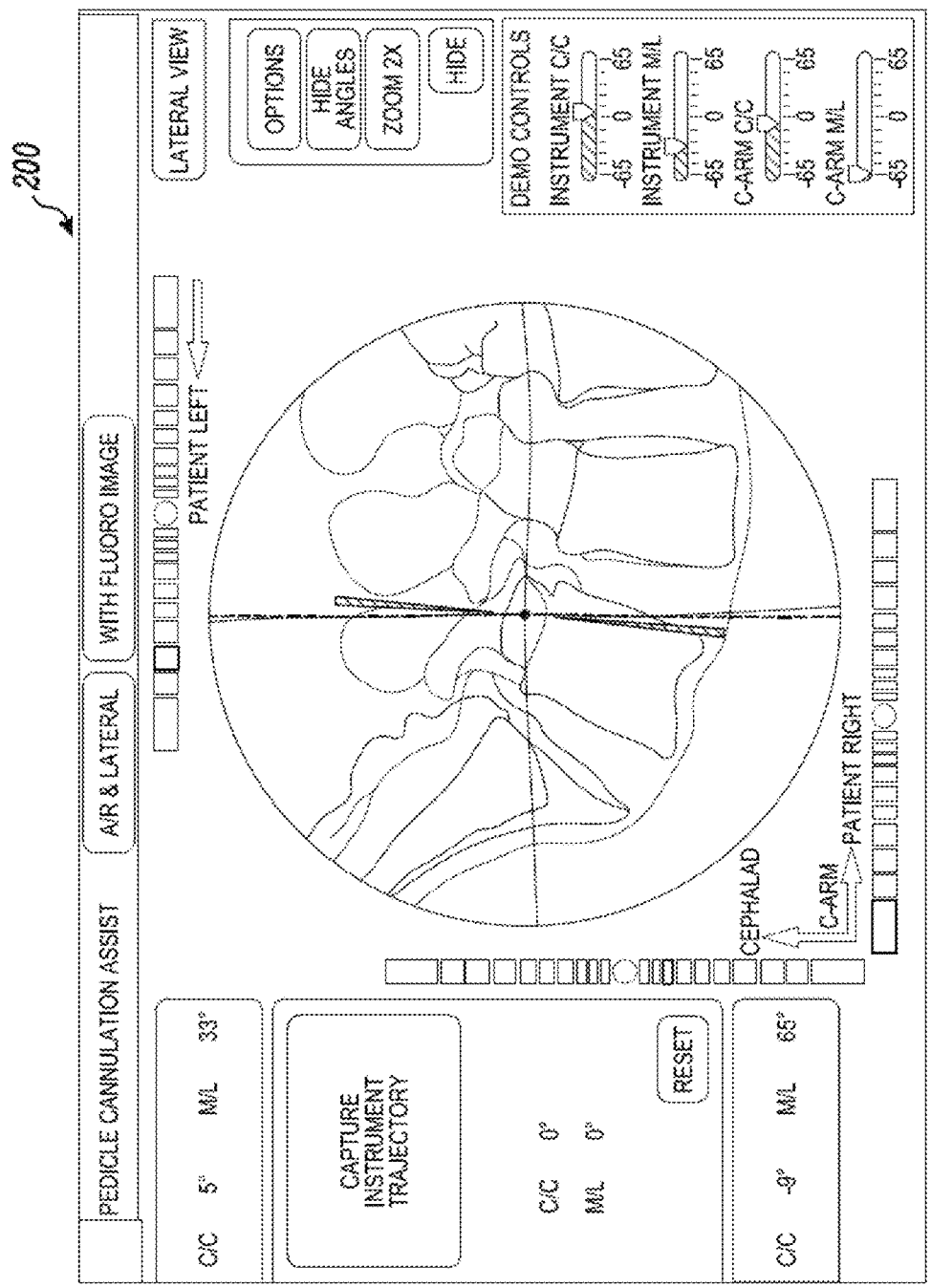
FIG. 25 is an exemplary screen display of a Navigated Guidance screen forming part of the neurophysiology system of FIG. 1.

The control unit 12 may communicate any of numerical, graphical, and audio feedback corresponding to the orientation of the tilt sensor in the sagittal plane (cranial-caudal angle) and in the transverse plane (medial-lateral angle). The medial-lateral and cranial-caudal angle readouts may be displayed simultaneously and continuously while the tilt sensor is in use, or any other variation thereof (e.g. individually and/or intermittently). FIG. 25 illustrates, by way of example only, one embodiment of a GUI screen for the Navigated Guidance function. The angular orientation of the instrument is displayed along with a color coded targeting scheme to help the user find the desired angle.

Figure 30:
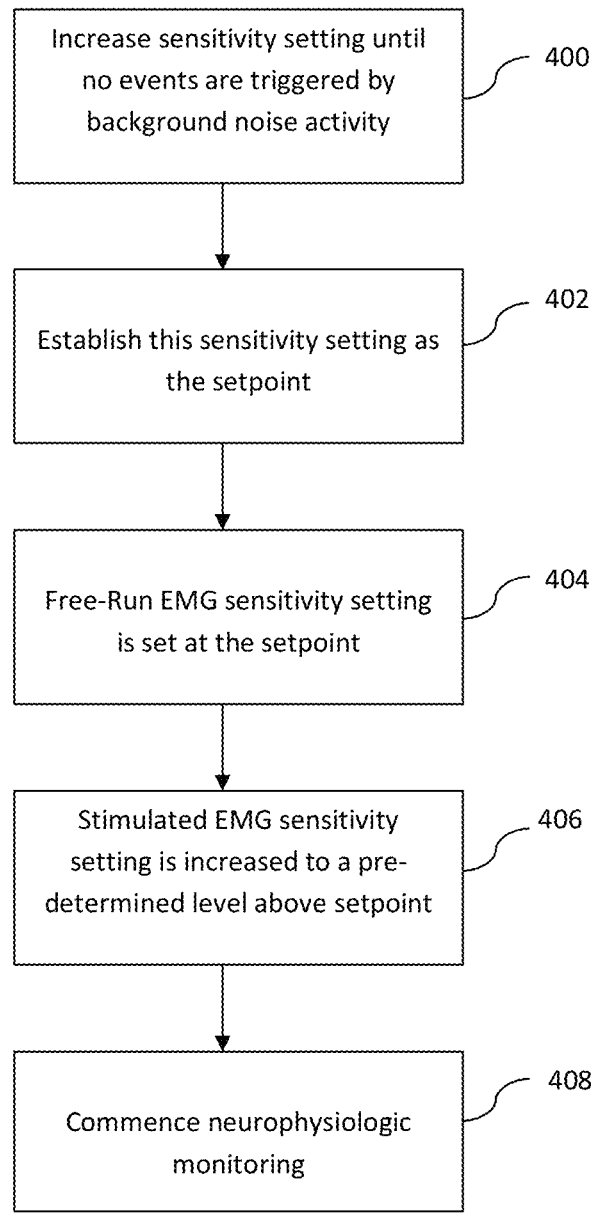
FIG. 30 is a flowchart indicating the steps involved in an amplitude discrimination algorithm according to one example embodiment.

Now, with reference to FIG. 30, there is shown a flowchart containing the steps of an amplitude discrimination algorithm according to one exemplary embodiment. The amplitude discrimination algorithm may be employed by the system when free-run EMG testing is performed concurrently with a stimulated EMG technique to quickly discern between simultaneous background activity (non-physiologic or physiologic) and evoked neurophysiologic activity. Prior to commencing monitoring, the sensitivity setting on the neurophysiology system 10 is increased, either manually or automatically, until there are no events triggered by background noise in the EMG recording channel (step 400). This sensitivity setting represents the setpoint (step 402). The free-run EMG threshold sensitivity setting is automatically set to the setpoint (step 404). Then, the stimulated EMG threshold sensitivity setting is automatically increased to a predetermined level above the setpoint (step 406).

Figure 31:
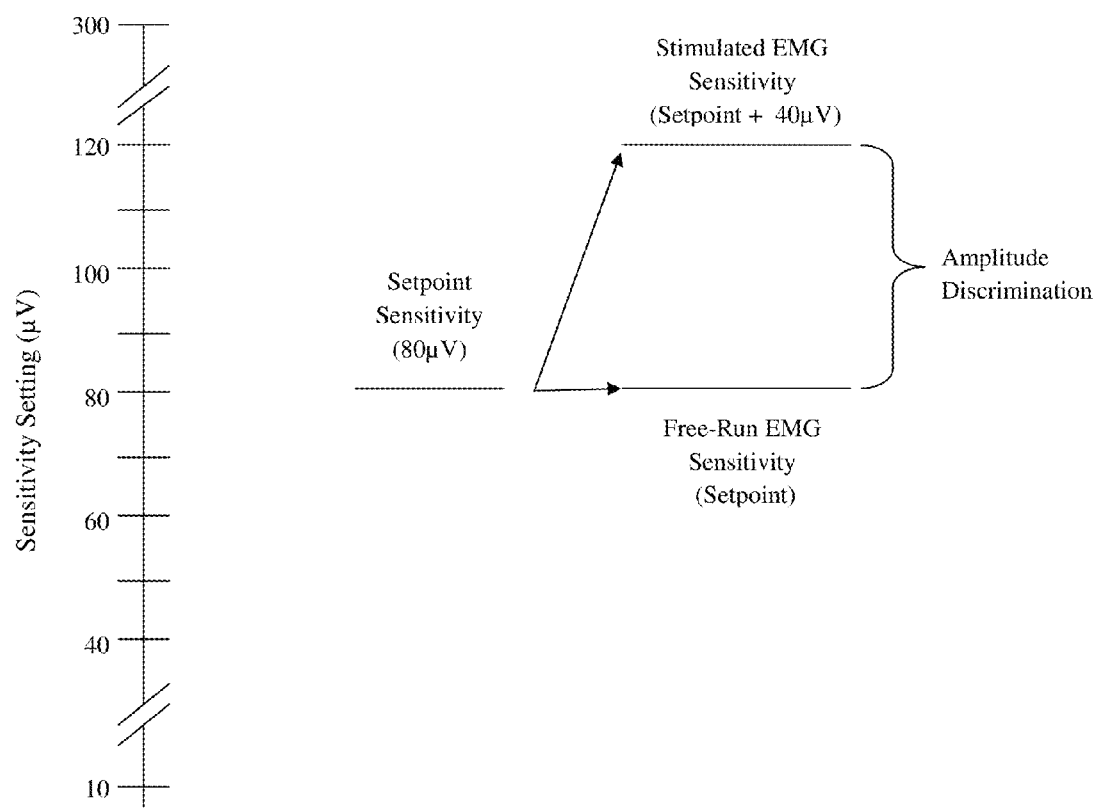
FIG. 31 is a diagram depicting one example embodiment of a fixed increase method of an amplitude discrimination algorithm according to the method of FIG. 30.

According to one embodiment (as illustrated in FIG. 31), this predetermined level can be a fixed increase (i.e., a predetermined voltage increase from the setpoint). It is contemplated that the fixed increase can be any number within the range of 1-1000 µV from the setpoint sensitivity setting. However, for illustrative purposes only, FIG. 31 shows a predetermined level of fixed increase of 40 µV and a setpoint set at 80 µV, representing the sensitivity setting at which all background noise activity ceases. From that setpoint (80 µV), the stimulated EMG threshold sensitivity is automatically increased by the fixed increase value of 40 µV to get 120 µV. It is contemplated that the stimulated EMG threshold sensitivity setting may be displayed on the display 34 as either the automatically adjusted sensitivity setting, the setpoint sensitivity setting, or both. Table 8 illustrates the effects of the amplitude discrimination algorithm on free-run EMG threshold voltages and stimulated EMG threshold voltages according to the fixed increased method, for an exemplary range of sensitivity settings. Once all sensitivity levels have been optimally determined, the neurophysiologic monitoring commences (step 408).

TABLE 8

| Fixed Increase Method (40 µV increase) | | |
|---|---|---|
| Sensitivity Setting (µV) | Free Run EMG $V_{pp}$ Threshold Voltage (µV) | Stimulated EMG $V_{pp}$ Threshold Voltage (µV) |
| 20 | 20 | 60 |
| 30 | 30 | 70 |
| 40 | 40 | 80 |
| 50 | 50 | 90 |
| 60 | 60 | 100 |
| 70 | 70 | 110 |
| 80 (default or normal) | 80 | 120 |
| 90 | 90 | 130 |
| 100 | 100 | 140 |
| 110 | 110 | 150 |
| 120 | 120 | 160 |
| 130 | 130 | 170 |
| 140 | 140 | 180 |
| 150 | 150 | 190 |
| 160 | 160 | 200 |
| 170 | 170 | 210 |
| 180 | 180 | 220 |
| 190 | 190 | 230 |
| 200 | 200 | 240 |
| 210 | 210 | 250 |
| 220 | 220 | 260 |
| 230 | 230 | 270 |
| 240 | 240 | 280 |
| 250 | 250 | 290 |
| 260 | 260 | 300 |
| 270 | 270 | 310 |
| 280 | 280 | 320 |
| 290 | 290 | 330 |
| 300 | 300 | 340 |

According to a further embodiment, the amplitude discrimination algorithm of FIG. 30 may also include a calculation to account for any increase (however minimal) in current intensity necessary to elicit a CMAP equal or greater than the increased $V_{pp}$ necessary for optimizing the stimulated EMG testing results.

Figure 29:
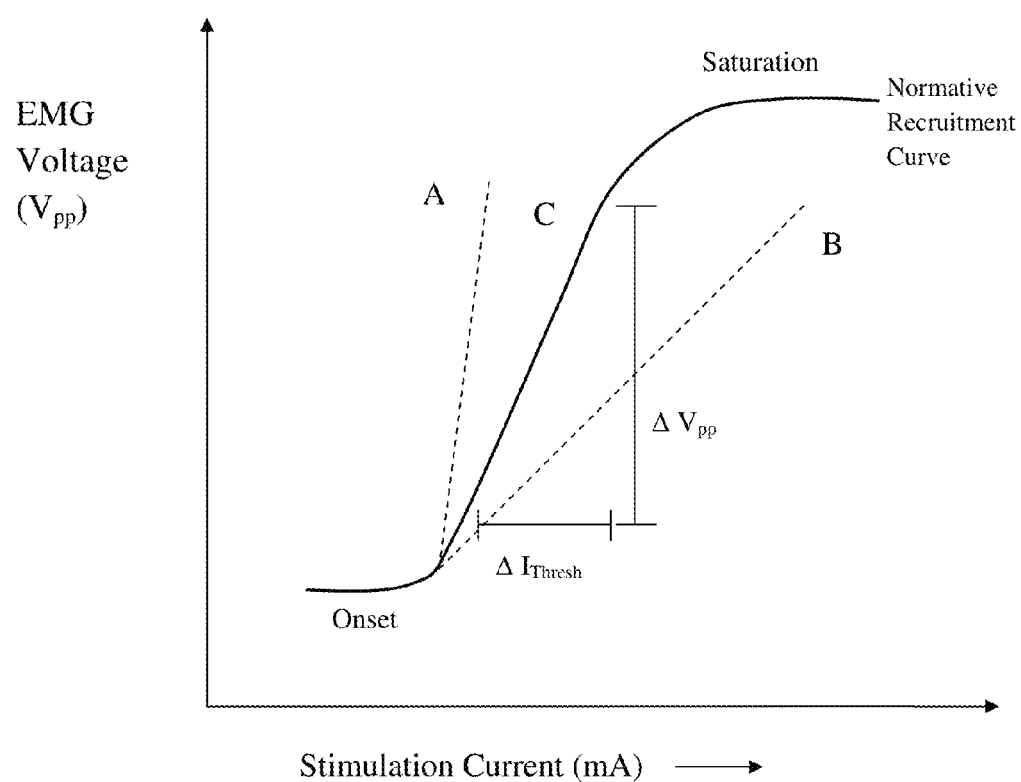
FIG. 29 is a graph illustrating a plot of the outer boundaries of normal recruitment curves and a normative recruitment curve.

The ability to correct the $I_{Thresh}$ results may be based in part on evaluating and selecting a normative range for the slope of the linear region of the recruitment curve ($\Delta V_{pp}/\Delta I_{stim}$). As highlighted in FIG. 28 and explained above, every muscle exhibits a generally S-shaped recruitment curve as its corresponding nerve is stimulated with increasing intensity. As depicted in FIG. 29, however, the slope of the linear region of the recruitment curve varies to some extent from person to person, or nerve to nerve. By way of example only, one person (or nerve) might require less current intensity to approach saturation, which would present a steeper slope from onset to saturation. Conversely, another person (or nerve) might require a larger intensity increase to approach saturation, which would present a shallower slope from onset to saturation. Clinical measurements of recruitment curves of the normal population may be taken and normative data can be used to derive the range of normal slopes of the linear region of the recruitment curve. As indicated in FIG. 29, linear region A represents the maximum observed slope and linear region B represents the minimum observed slope among the normal population. From this range, a normalized recruitment curve can be selected. Thus, taken together, slopes A and B represent the outer bounds of the linear regions of recruitment curves. From this range, a normative recruitment curve (with a middle value linear region slope) can be selected, as represented by normative slope C. This normative recruitment curve slope can be used in conjunction with known adjusted sensitivity settings ($V_{pp}$ thresholds) to make stimulation threshold correction determinations. Alternatively, the recruitment curve slope of the particular nerve being stimulated may be measured and that value used in place of a normative value.

For purposes of illustration only, an assumption has been made that the normalized recruitment curve slope is experientially determined to be 50 µV/mA. In accordance with the steps disclosed above, the sensitivity setting is increased until there is no background noise activity in the EMG channel ($V_{pp(Setpoint)}$). For illustrative purposes, suppose that the $V_{pp}$ (Setpoint) is determined to be 100 µV. Supposing also that, under the fixed increase method of the amplitude discrimination algorithm as explained above, the desired fixed increase is 100 µV above the setpoint. Then, the adjusted sensitivity setting ($V_{pp(Adjusted)}$) is 200 µV (100 µV set point+100 µV fixed increase). Next assume that, using the adjusted sensitivity setting in accordance with the amplitude discrimination algorithm, the stimulated EMG testing results in an $I_{Thresh}$ determined using the adjusted sensitivity level ($I_{Thresh(Adjusted)}$) of 14 mA. Because the adjusted sensitivity setting was increased above the setpoint to account for unwanted background noise contamination, the $I_{Thresh}$ can now be "corrected" back to the threshold that would have been observed at a $V_{pp(Setpoint)}$ of 100 µV. One such correction can be calculated as:

$$I_{Thresh(Corrected)} = I_{Thresh(Adjusted)} + \frac{(V_{pp(Setpoint)} - V_{pp(Adjusted)})}{(\Delta V_{pp(Normative)} / \Delta I_{(Normative)})}$$

$$I_{Thresh(Corrected)} = 14 \text{ mA} + \frac{(100 \text{ µV} - 200 \text{ µV})}{(50 \text{ µV/mA})}$$

$$I_{Thresh(Corrected)} = 12 \text{ mA}$$

Therefore, the $I_{Thresh(Corrected)}$ is 12 mA. That is, 12 mA is the stimulus intensity that would have been required to elicit a significant $V_{pp}$ response at the lower sensitivity setting of 100 µV. However, by adjusting for the noise and then correcting back, a high-quality $I_{Thresh}$ reading is obtained without any concomitant noise contamination of the response.

Figure 32:
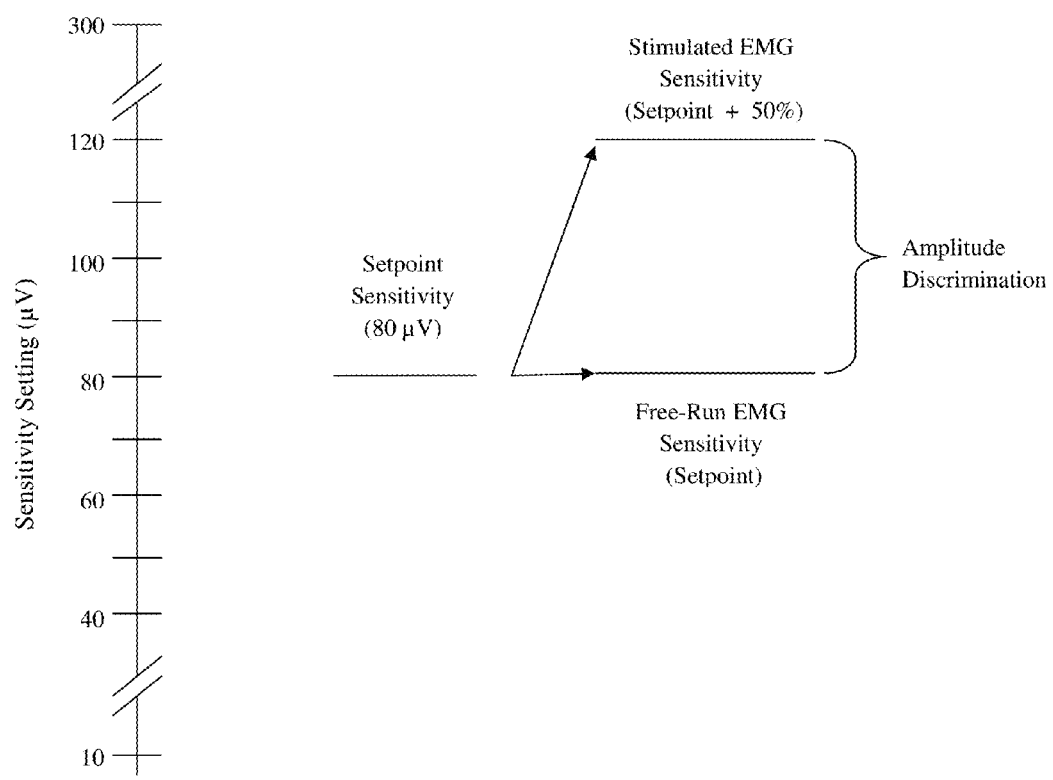
FIG. 32 is a diagram depicting one example embodiment of a percent increase method of an amplitude discrimination algorithm according to the method of FIG. 30.

According to an alternate embodiment (as illustrated in FIG. 32), the predetermined level increase of the amplitude discrimination algorithm (FIG. 30) may be a percent increase (i.e., a predetermined percentage increase in voltage from the setpoint). It is contemplated that the percentage increase can be within the range of 10%-400% from the setpoint sensitivity setting. However, for illustrative purposes only, FIG. 31 shows a predetermined level of percentage increase of 50% and a setpoint set at 80 µV, representing the sensitivity setting for which all background noise activity ceases. From that setpoint (80 µV), the stimulated EMG threshold sensitivity is automatically increased by the percentage increase of 50% to 120 µV. It is contemplated that the stimulated EMG threshold sensitivity setting may be displayed on the display 34 as either the automatically adjusted sensitivity setting or the setpoint sensitivity setting or both. Table 9 illustrates the effects of the amplitude discrimination algorithm on free-run EMG threshold voltages and stimulated EMG threshold voltages according to the percent increased method, for an exemplary range of sensitivity settings. Once all sensitivity levels have been optimally determined, the neurophysiologic monitoring commences (step 408).

TABLE 9

Percent Increase Method (50% increase)

| Sensitivity Setting (µV) | Free Run EMG $V_{pp}$ Threshold Voltage (µV) | Stimulated EMG $V_{pp}$ Threshold Voltage (µV) |
|---|---|---|
| 20 | 20 | 30 |
| 30 | 30 | 45 |
| 40 | 40 | 60 |
| 50 | 50 | 75 |
| 60 | 60 | 90 |
| 70 | 70 | 105 |
| 80 (default or normal) | 80 | 120 |
| 90 | 90 | 135 |
| 100 | 100 | 150 |
| 110 | 110 | 165 |
| 120 | 120 | 180 |
| 130 | 130 | 195 |
| 140 | 140 | 210 |
| 150 | 150 | 225 |
| 160 | 160 | 240 |
| 170 | 170 | 255 |
| 180 | 180 | 270 |
| 190 | 190 | 285 |
| 200 | 200 | 300 |
| 210 | 210 | 315 |
| 220 | 220 | 330 |
| 230 | 230 | 345 |
| 240 | 240 | 360 |
| 250 | 250 | 375 |
| 260 | 260 | 390 |
| 270 | 270 | 405 |
| 280 | 280 | 420 |
| 290 | 290 | 435 |
| 300 | 300 | 450 |

According to a further embodiment, the amplitude discrimination algorithm may include the further step of applying corrective measurements to the stimulated EMG results as described in detail above. Assuming a similar exemplary calculation (with a normalized recruitment curve slope of 50 µV/mA), the sensitivity setting is increased until there is no background noise activity in the EMG channel ($V_{pp(Setpoint)}$ of 100 µV). Under the percentage increase method of the amplitude discrimination algorithm of FIG. 32, assume the desired percentage increase is 100% above the setpoint (100 µV). Therefore, the adjusted sensitivity setting ($V_{pp(Adjusted)}$) is 200 µV (100 µV set point+100% percent increase above 100 µV). Using the adjusted sensitivity setting in accordance with the amplitude discrimination algorithm, the stimulated EMG testing results in an $I_{Thresh(Adjusted)}$ of 14 mA. Because the adjusted sensitivity setting was increased above the setpoint to account for unwanted background noise contamination, the $I_{Thresh}$ can now be "corrected" back to the threshold that would have been observed at a $V_{pp(Setpoint)}$ of 100 µV. One such correction can be calculated as:

$$I_{Thresh(Corrected)} = I_{Thresh(Adjusted)} + \frac{(V_{pp(Setpoint)} - V_{pp(Adjusted)})}{(\Delta V_{pp(Normative)} / \Delta I_{(Normative)})}$$

$$I_{Thresh(Corrected)} = 14 \text{ mA} + \frac{(100 \text{ }\mu V - 200 \text{ }\mu V)}{(50 \text{ }\mu V/\text{mA})}$$

$$I_{Thresh(Corrected)} = 12 \text{ mA}$$

Therefore, the $I_{Thresh(Corrected)}$ is 12 mA. That is, 12 mA is the stimulus intensity that would have been required to elicit a significant $V_{pp}$ response at the lower sensitivity setting of 100 µV. However, by adjusting for the noise and then correcting back, a high-quality $I_{Thresh}$ reading is obtained without any concomitant noise contamination of the response.

Figure 33:
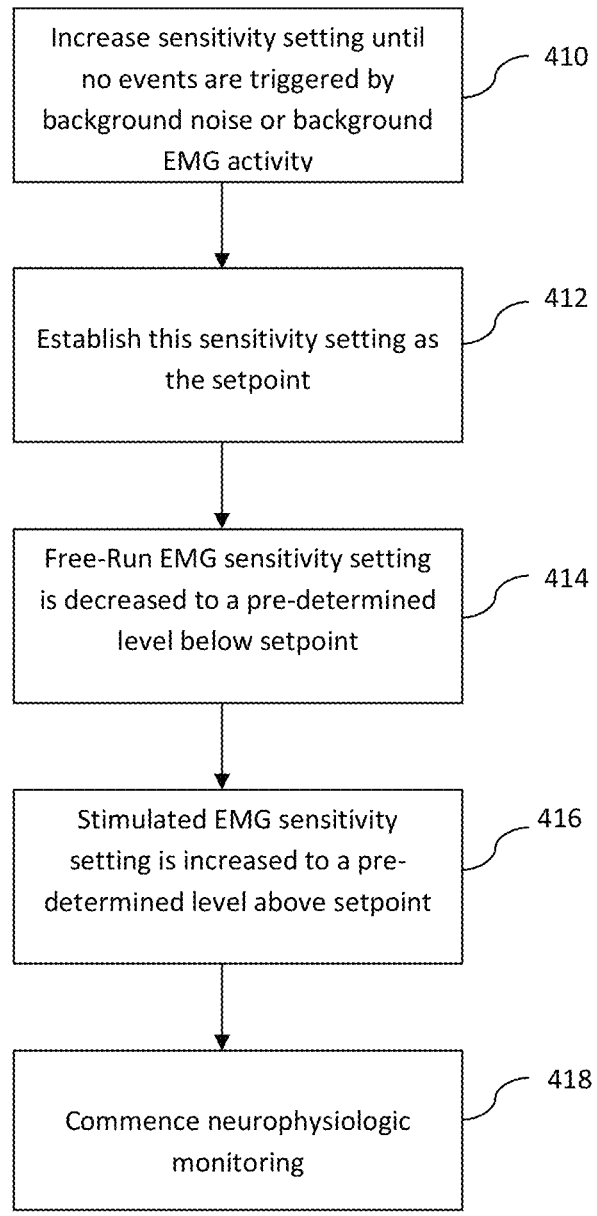
FIG. 33 is a flowchart indicating the steps involved in an amplitude discrimination algorithm according to another example embodiment.

FIG. 33 is a flowchart indicating the steps used in an amplitude discrimination algorithm according to another exemplary embodiment. Prior to commencing monitoring, the sensitivity setting on the neurophysiology system 10 is increased until there are no events triggered by background noise or background neurophysiologic activity in the EMG recording channel (step 410). This sensitivity setting represents the setpoint (step 412). To verify that the appropriate setpoint has been chosen, a delay may preferably be employed to ensure that there has, in fact, been no additional background neurophysiologic activity. The delay may be a predetermined length of time between 1 and 10 seconds. For illustrative purposes only, the delay may be 5 seconds. Then, the stimulated EMG threshold sensitivity setting is automatically increased to a predetermined level above the setpoint (step 414). Also after the delay, the free-run EMG threshold sensitivity setting is automatically decreased to a predetermined level below the setpoint (step 416).

Figure 34:
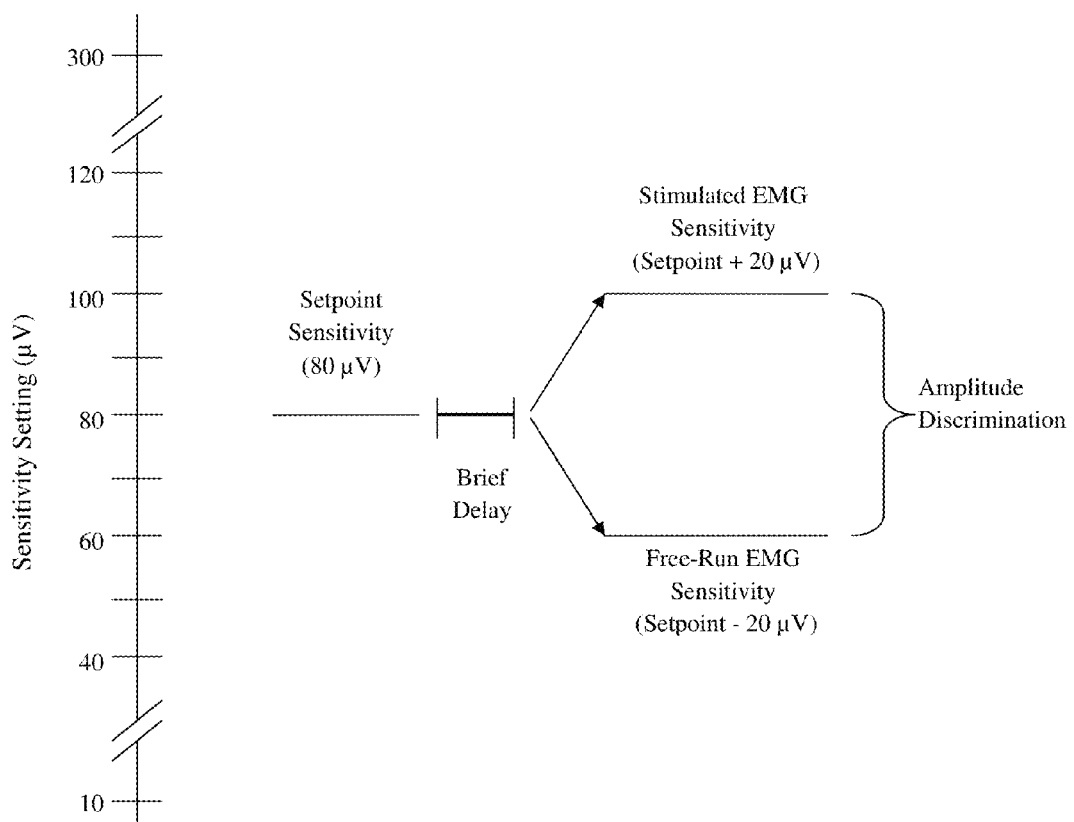
FIG. 34 is a diagram depicting one example embodiment of a fixed offset level method of an amplitude discrimination algorithm according to the method of FIG. 33.

According to one embodiment (as illustrated in FIG. 34), the predetermined level increase of the amplitude discrimination algorithm (FIG. 33) may be a fixed offset (i.e., a predetermined fixed offset in voltage from the setpoint). It is contemplated that the fixed offset level can be within the range of 1-200 µV from the setpoint sensitivity setting. However, for illustrative purposes only, FIG. 34 shows a predetermined fixed offset level increase of 20 µV and a setpoint set at 80 µV, representing the sensitivity setting for which all background noise and background neurophysiologic activity ceases. From that setpoint (80 µV), the free-run EMG threshold sensitivity is automatically decreased by the fixed offset level of 20 µV to 60 µV and the stimulated EMG threshold sensitivity is automatically increased by the fixed offset level of 20 µV to 100 µV. It is contemplated that the stimulated EMG threshold sensitivity setting may be displayed on the display 34 as either the automatically adjusted sensitivity setting or the setpoint sensitivity setting or both. Table 10 illustrates the effects of the amplitude discrimination algorithm on free-run EMG threshold voltages and stimulated EMG threshold voltages according to the fixed offset method, for an exemplary range of sensitivity settings. While the fixed offsets for the free-run and stimulated EMG threshold sensitivities are illustrated in FIG. 34 and Table 10 as equal, they may be different. For example, the free-run EMG threshold sensitivity may, by way of example only, have a fixed offset of 10 µV and the stimulated EMG threshold sensitivity may, by way of example only, have a fixed offset of 30 µV. Once all sensitivity levels have been optimally determined, the neurophysiologic monitoring commences (step 418).

TABLE 10

| | Fixed Offset Method (20 µV offset) | |
|---|---|---|
| Sensitivity Setting (µV) | Free Run EMG $V_{pp}$ Threshold Voltage (µV) | Stimulated EMG $V_{pp}$ Threshold Voltage (µV) |
| 20 | 0 | 40 |
| 30 | 10 | 50 |
| 40 | 20 | 60 |
| 50 | 30 | 70 |
| 60 | 40 | 80 |
| 70 | 50 | 90 |
| 80 (default or normal) | 60 | 100 |
| 90 | 70 | 110 |
| 100 | 80 | 120 |
| 110 | 90 | 130 |
| 120 | 100 | 140 |
| 130 | 110 | 150 |
| 140 | 120 | 160 |
| 150 | 130 | 170 |
| 160 | 140 | 180 |
| 170 | 150 | 190 |
| 180 | 160 | 200 |
| 190 | 170 | 210 |
| 200 | 180 | 220 |
| 210 | 190 | 230 |
| 220 | 200 | 240 |
| 230 | 210 | 250 |
| 240 | 220 | 260 |
| 250 | 230 | 270 |
| 260 | 240 | 280 |
| 270 | 250 | 290 |
| 280 | 260 | 300 |
| 290 | 270 | 310 |
| 300 | 280 | 320 |

According to a further embodiment, the amplitude discrimination algorithm may include the further step of applying corrective measurements to the stimulated EMG results as described in detail above. Assuming a similar exemplary calculation (with a normalized recruitment curve slope of 50 µV/mA), the sensitivity setting is increased until there is no background noise activity or background neurophysiologic activity in the EMG channel ($V_{pp(Setpoint)}$ of 100 µV). Under the fixed offset level method of the amplitude discrimination algorithm of FIG. 34, assume the desired fixed offset level above the setpoint is 100 µV. Therefore, the adjusted sensitivity setting ($V_{pp(Adjusted)}$) is 200 µV (100 µV set point+100 µV fixed offset). Using the adjusted sensitivity setting in accordance with the amplitude discrimination algorithm, the stimulated EMG testing results in an $I_{Thresh(Adjusted)}$ of 14 mA. Because the adjusted sensitivity setting was increased above the setpoint to account for unwanted background contamination, the $I_{Thresh}$ can now be "corrected" back to the threshold that would have been observed at a $V_{pp(Setpoint)}$ of 100 µV. One such correction can be calculated as:

$$I_{Thresh(Corrected)} = I_{Thresh(Adjusted)} + \frac{(V_{pp(Setpoint)} - V_{pp(Adjusted)})}{(\Delta V_{pp(Normative)} / \Delta I_{(Normative)})}$$

$$I_{Thresh(Corrected)} = 14 \text{ mA} + \frac{(100 \text{ }\mu V - 200 \text{ }\mu V)}{(50 \text{ }\mu V/\text{mA})}$$

$$I_{Thresh(Corrected)} = 12 \text{ mA}$$

Therefore, the $I_{Thresh(Corrected)}$ is 12 mA. That is, 12 mA is the stimulus intensity that would have been required to elicit a significant $V_{pp}$ response at the lower sensitivity setting of 100 µV. However, by adjusting for the noise and then correcting back, a high-quality $I_{Thresh}$ reading is obtained without any concomitant noise contamination of the response.

Figure 35:
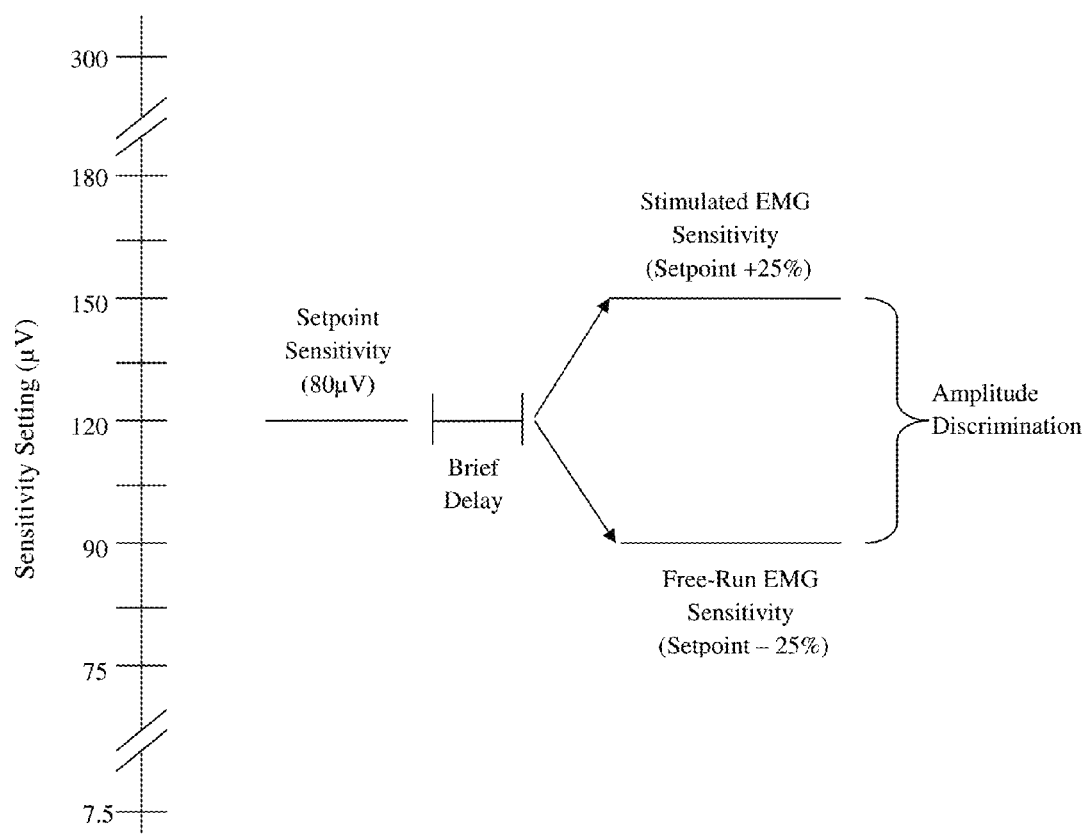
FIG. 35 is a diagram depicting one example embodiment of a percent offset level method of an amplitude discrimination algorithm according to the method of FIG. 33.
Figure 36A:
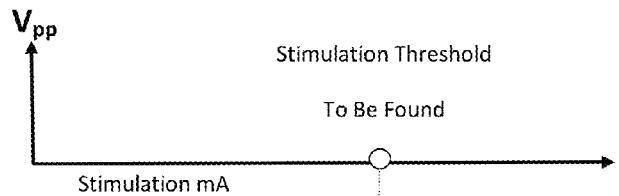
FIGS. 36 A-D are graphs illustrating the fundamental steps of a rapid current threshold-hunting algorithm according to one embodiment of the present invention.
Figure 36B:
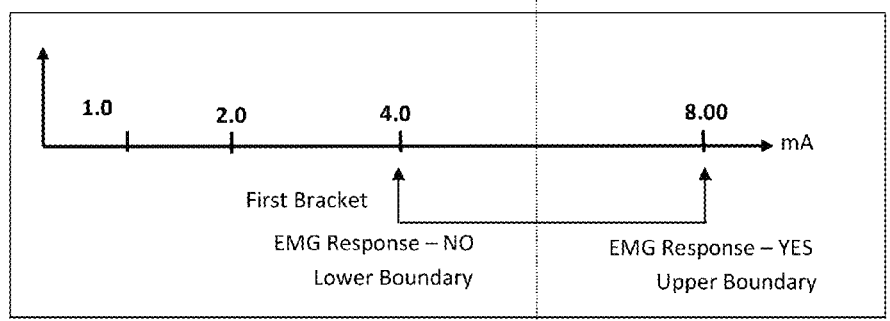
Figure 36C:
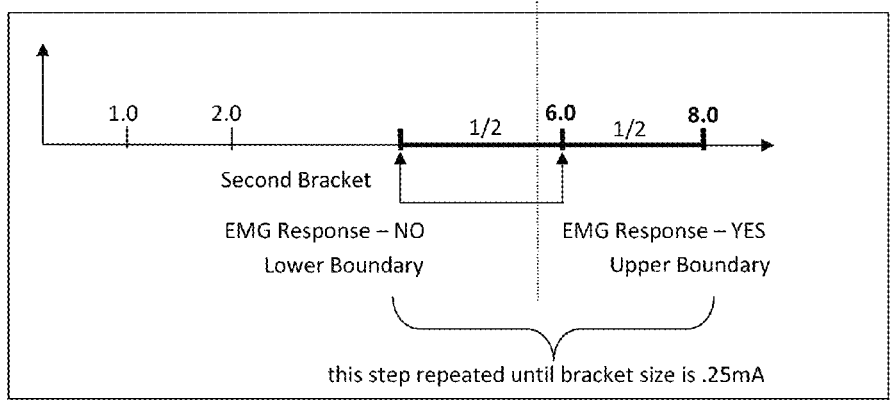
Figure 36D:
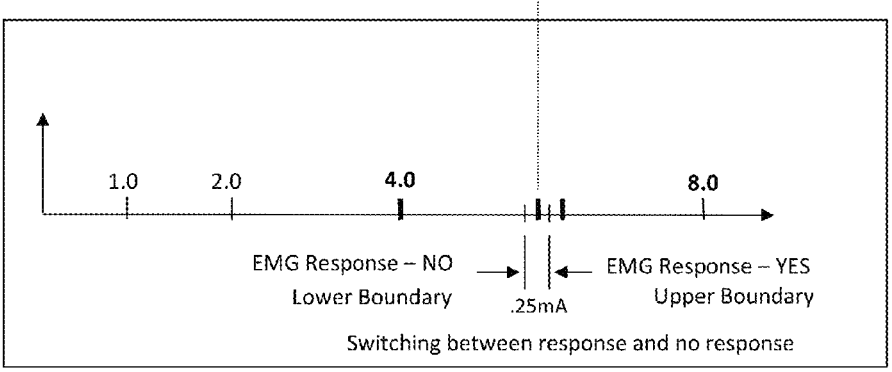

According to another embodiment (as illustrated in FIG. 35), the predetermined level increase of the amplitude discrimination algorithm (FIG. 33) may be a percent offset (i.e., a predetermined percentage offset in voltage from the setpoint). It is contemplated that the percentage offset level can be within the range of 10-400% from the setpoint sensitivity setting. However, for illustrative purposes only, FIG. 35 shows a predetermined percentage offset level of 25% and a setpoint set at 80 µV, representing the sensitivity setting for which all background noise and background neurophysiologic activity ceases. From that setpoint (80 µV), the free-run EMG threshold sensitivity is automatically decreased by the percentage offset level of 25% to 60 µV and the stimulated EMG threshold sensitivity is automatically increased by the percentage offset level of 25% to 120 µV. It is contemplated that the stimulated EMG threshold sensitivity setting may be displayed on the display 34 as either the automatically adjusted sensitivity setting or the setpoint sensitivity setting or both. Table 11 illustrates the effects of the amplitude discrimination algorithm on free-run EMG threshold voltages and stimulated EMG threshold voltages according to the percent offset method, for an exemplary range of sensitivity settings. While the percent offsets for the free-run and stimulated EMG threshold sensitivities are illustrated in FIG. 35 and Table 11 as equal, they may be different. For example, the free-run EMG threshold sensitivity may, by way of example only, have a percent offset of 10% and the stimulated EMG threshold sensitivity may, by way of example only, have a percent offset of 30%. Once all sensitivity levels have been optimally determined, the neurophysiologic monitoring commences (step 418).

TABLE 11

Percent Offset Method (25% offset)

| Sensitivity Setting (µV) | Free Run EMG $V_{pp}$ Threshold (µV) | Stimulated EMG $V_{pp}$ Threshold (µV) |
|---|---|---|
| 20 | 15.0 | 25.0 |
| 30 | 22.5 | 37.5 |
| 40 | 30.0 | 50.0 |
| 50 | 37.5 | 62.5 |
| 60 | 45.0 | 75.0 |
| 70 | 52.5 | 87.5 |
| 80 (default or normal) | 60.0 | 100.0 |
| 90 | 67.5 | 112.5 |
| 100 | 75.0 | 125.0 |
| 110 | 82.5 | 137.5 |
| 120 | 90.0 | 150.0 |
| 130 | 97.5 | 162.5 |
| 140 | 105.0 | 175.0 |
| 150 | 112.5 | 187.5 |
| 160 | 120.0 | 200.0 |
| 170 | 127.5 | 212.5 |
| 180 | 135.0 | 225.0 |
| 190 | 142.5 | 237.5 |
| 200 | 150.0 | 250.0 |
| 210 | 157.5 | 262.5 |
| 220 | 165.0 | 275.0 |
| 230 | 172.5 | 287.5 |
| 240 | 180.0 | 300.0 |
| 250 | 187.5 | 312.5 |
| 260 | 195.0 | 325.0 |
| 270 | 202.5 | 337.5 |
| 280 | 210.0 | 350.0 |
| 290 | 217.5 | 362.5 |
| 300 | 225.0 | 375.0 |

According to a further embodiment, the amplitude discrimination algorithm may include the further step of applying corrective measurements to the stimulated EMG results as described in detail above. Assuming a similar exemplary calculation (with a normalized recruitment curve slope of 50 µV/mA), the sensitivity setting is increased until there is no background noise activity or background neurophysiologic activity in the EMG channel ($V_{pp(Setpoint)}$ of 100 µV). Under the percent offset method of the amplitude discrimination algorithm of FIG. 35, assume the desired percent offset above the setpoint is 100%. Therefore, the adjusted sensitivity setting ($V_{pp(Adjusted)}$) is 200 µV (100 µV set point+100% percent offset of 100 µV). Using the adjusted sensitivity setting in accordance with the amplitude discrimination algorithm, the stimulated EMG testing results in an $I_{Thresh(Adjusted)}$ of 14 mA. Because the adjusted sensitivity setting was increased above the setpoint to account for unwanted background contamination, the $I_{Thresh}$ can now be "corrected" back to the threshold that would have been observed at a $V_{pp(Setpoint)}$ of 100 µV. One such correction can be calculated as:

$$I_{Thresh(Corrected)} = I_{Thresh(Adjusted)} + \frac{(V_{pp(Setpoint)} - V_{pp(Adjusted)})}{(\Delta V_{pp(Normative)}/\Delta I_{(Normative)})}$$

$$I_{Thresh(Corrected)} = 14 \text{ mA} + \frac{(100 \text{ µV} - 200 \text{ µV})}{(50 \text{ µV/mA})}$$

$$I_{Thresh(Corrected)} = 12 \text{ mA}$$

Therefore, the $I_{Thresh(Corrected)}$ is 12 mA. That is, 12 mA is the stimulus intensity that would have been required to elicit a significant $V_{pp}$ response at the lower sensitivity setting of 100 µV. However, by adjusting for the noise and then correcting back, a high-quality $I_{Thresh}$ reading is obtained without any concomitant noise contamination of the response.

The amplitude discrimination algorithm may be of particular use when stimulated EMG is used to perform static pedicle integrity testing, dynamic pedicle integrity testing, nerve proximity detection, and neuromuscular pathway assessments. In these modalities, it is oftentimes desirable to perform free-run EMG monitoring during or in between testing in these modalities. During these instances where free-run EMG and stimulated EMG testing are simultaneously performed, utilization of the amplitude discrimination algorithm in accordance with one of the fixed increase method of FIG. 31, the percent increase method of FIG. 32, the fixed offset method of FIG. 34, and the percent offset method of FIG. 35, may decrease the likelihood of false positives in stimulated EMG recordings associated with background EMG activity and background EMG noise "contamination." Use of any of these four methods also decreases the likelihood of false negatives in free-run EMG recordings because the optimal sensitivity setting for free-run EMG recordings is not sacrificed for high-quality stimulated EMG responses. Decreasing the incidence of false positives and negatives may promote confidence in the neurophysiologic monitoring system and provide opportunities for improved patient outcomes.

The amplitude discrimination algorithm may also be of particular use during MEP monitoring. When surgical procedures are performed in close proximity of the spinal cord, potential damage to the spinal cord is a concern. Consequences of spinal cord damage may range from a slight loss of sensation to complete paralysis of the extremities, depending on the location and extent of damage. MEP monitoring generally involves monitoring the transmission of an electrical signal along the spinal cord as measured by EMG responses in distal muscles of the target extremities. High amounts of background noise may taint MEP recordings causing a neurophysiologist or a neurophysiology system to indicate there is a positive MEP response when in actuality, it is merely background noise (false negative). Therefore, the algorithm may be employed to discriminate between the background noise in the EMG channels and the presence of an MEP response.

Having described the amplitude discrimination algorithm to help accurately detect events surpassing the voltage threshold, techniques for quickly finding $I_{Thresh}$ are described. FIGS. 36 A-D illustrate, by way of example only, the principles of a threshold hunting algorithm of the present invention used to quickly find $I_{Thresh}$. The method for finding $I_{Thresh}$ utilizes a bracketing method and a bisection method. The bracketing method quickly finds a range (bracket) of stimulation currents that must contain $I_{Thresh}$ and the bisection method narrows the bracket until $I_{Thresh}$ is known within a specified accuracy. If the stimulation current threshold, $I_{Thresh}$, of a channel exceeds a maximum stimulation current, that threshold is considered out of range.

FIGS. 36 A-D illustrate the bracketing feature of the threshold hunting algorithm of the present invention. Stimulation begins at a minimum stimulation current, such as (by way of example only) 1 mA. It will be appreciated that the relevant current values depend in part on the function performed (e.g. high currents are used for MEP and low currents are generally used for other functions) and the current values described here are for purposes of example only and may in actuality be adjusted to any scale. The level of each subsequent stimulation is doubled from the preceding stimulation level until a stimulation current recruits (i.e. results in an EMG response with a $V_{pp}$ greater or equal to $V_{Thresh}$). The first stimulation current to recruit (8 mA in FIG. 36 B), together with the last stimulation current to have not recruited (4 mA in FIG. 36 B), forms the initial bracket.

FIGS. 36 C-D illustrate the bisection feature of the threshold hunting algorithm of the present invention. After the threshold current $I_{Thresh}$ has been bracketed (FIG. 36 B), the initial bracket is successively reduced via bisection to a predetermined width, such as (by way of example only) 0.25 mA. This is accomplished by applying a first bisection stimulation current that bisects (i.e. forms the midpoint of) the initial bracket (6 mA in FIG. 36 C). If this first bisection stimulation current recruits, the bracket is reduced to the lower half of the initial bracket (e.g. 4 mA and 6 mA in FIG. 36 C). If this first bisection stimulation current does not recruit, the bracket is reduced to the upper half of the initial bracket (e.g. 6 mA and 8 mA in FIG. 36 C). This process is continued for each successive bracket until $I_{Thresh}$ is bracketed by stimulation currents separated by the predetermined width (which, in this case, is 0.25 mA). In this example shown, this would be accomplished by applying a second bisection stimulation current (forming the midpoint of the second bracket, or 5 mA in this example). Because this second bisection stimulation current is below $I_{Thresh}$, it will not recruit. As such, the second bracket will be reduced to the upper half thereof (5 mA to 6 mA), forming a third bracket. A third bisection stimulation current forming the mid-point of the third bracket (5.50 mA in this case) will then be applied. Because this third bisection stimulation current is below $I_{Thresh}$, it will not recruit. As such, the third bracket will be reduced to the upper half thereof (5.50 mA to 6 mA), forming a fourth bracket. A fourth bisection stimulation current forming the mid-point of the fourth bracket (5.75 mA in this case) will then be applied. Because the fourth bisection stimulation current is above $I_{Thresh}$, it will recruit. The final bracket is therefore between 5.50 mA and 5.75 mA. Due to the "response" or recruitment at 5.50 mA and "no response" or lack of recruitment at 5.75 mA, it can be inferred that $I_{Thresh}$ is within this range. In one embodiment, the midpoint of this final bracket may be defined as $I_{Thresh}$, however, any value falling within the final bracket may be selected as $I_{Thresh}$ without departing from the scope of the present invention. Depending on the active mode, the algorithm may stop after finding $I_{Thresh}$ for the first responding channel (i.e. the channel with the lowest $I_{Thresh}$) or the bracketing and bisection steps may be repeated for each channel to determine $I_{Thresh}$ for each channel. In one embodiment, this multiple channel $I_{Thresh}$ determination may be accomplished by employing the additional steps of the multi-channel threshold detection algorithm, described below.

Additionally, in the "dynamic" functional modes, including, but not necessarily limited to Dynamic Stimulation EMG and XLIF®, the system may continuously update the stimulation threshold level and indicate that level to the user. To do so, the threshold hunting algorithm does not repeatedly determine the $I_{Thresh}$ level anew, but rather, it determines whether stimulation current thresholds are changing. This is accomplished, as illustrated in FIG. 36 D, by a monitoring phase that involves switching between stimulations at lower and upper ends of the final bracket. If the threshold has not changed then the lower stimulation current should not evoke a response, while the upper end of the bracket should. If either of these conditions fail, the bracket is adjusted accordingly. The process is repeated for each of the active channels to continue to assure that each threshold is bracketed. If stimulations fail to evoke the expected response three times in a row, then the algorithm transitions back to the bracketing state in order to reestablish the bracket. In the event a change in $I_{Thresh}$ is detected during the monitoring phase, the user may be alerted immediately via the screen display and/or audio feedback. By way of example only, the color shown on the display corresponding to the previous $I_{Thresh}$ can be altered to a neutral color (e.g. black, grey, etc. . . . ) as soon as the change in $I_{Thresh}$ is detected but before the new $I_{Thresh}$ value is determined. If an audio tone is used to represent a particular safety level, the tone can cease as soon as the change in detected. Once the new $I_{Thresh}$ value is determined the color and/or audio tone can be altered again to signify the value.

Figure 37:
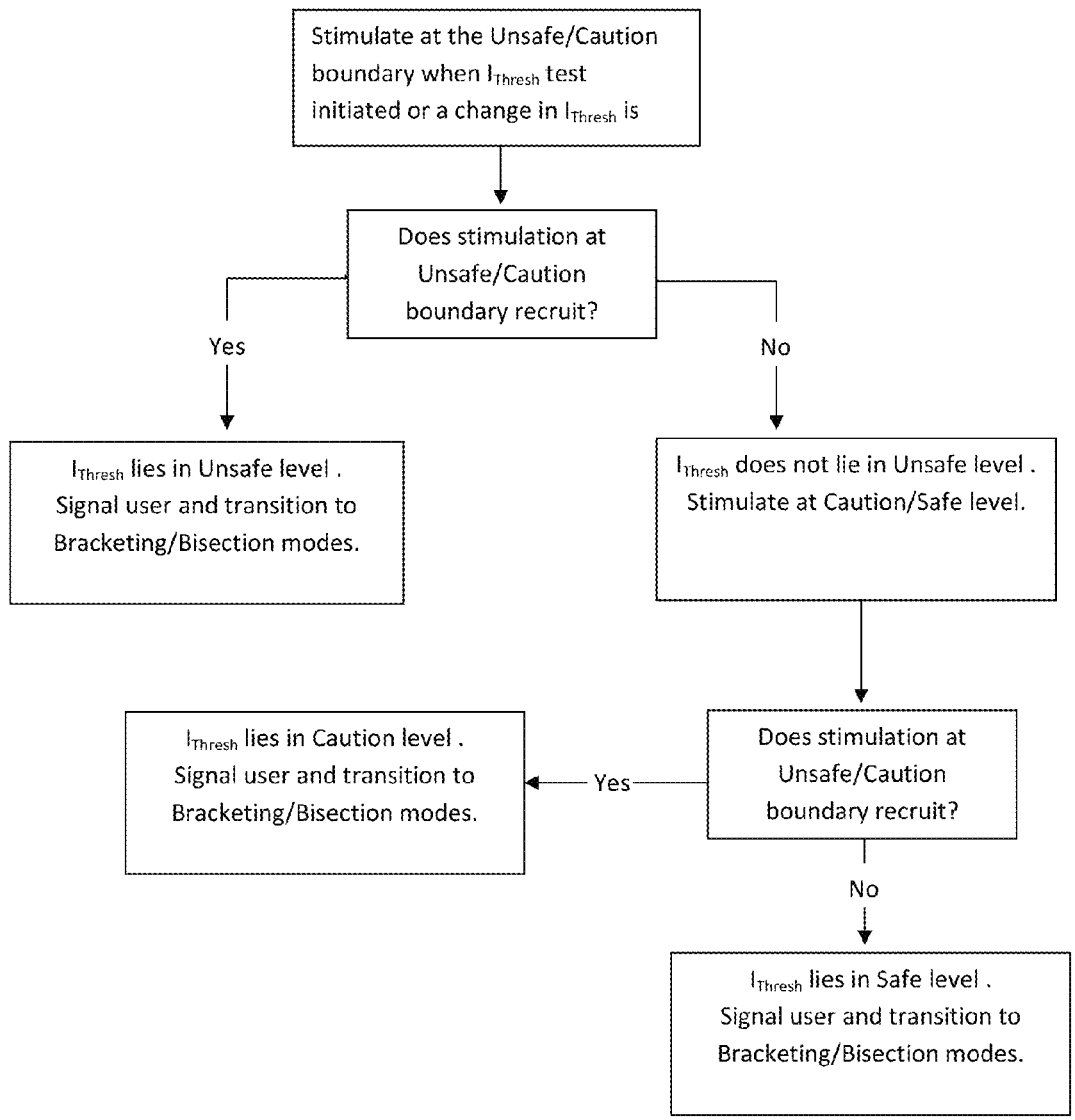
FIG. 37 is block diagram illustrating the steps of an initiation sequence for determining a relevant safety level prior to determining a precise threshold value according to an alternate embodiment of the threshold hunting algorithm of FIG. 36 A-D.

In an alternative embodiment, rather than beginning by entering the bracketing phase at the minimum stimulation current and bracketing upwards until $I_{Thresh}$ is bracketed, the threshold hunting algorithm may begin by immediately determining the appropriate safety level and then entering the bracketing phase. The algorithm may accomplish this by initiating stimulation at one or more of the boundary current levels. By way of example only, and with reference to FIG. 37, the algorithm may begin by delivering a stimulation signal at the boundary between the unsafe (e.g. red) and caution (e.g. yellow) levels. If the safety level is not apparent after the first stimulation, the algorithm may stimulate again at the boundary between the caution (e.g. yellow) and safe (e.g. green) levels. Once the safety level is known (i.e. after the first stimulation if the safety level is red, or, after the second stimulation if the safety level is yellow or green) the screen display may be updated to the appropriate color and/or coded audio signals may be emitted. As the screen display is updated, the algorithm may transition to the bracketing and bisection phases to determine the actual $I_{Thresh}$ value. When the $I_{Thresh}$ value is determined the display may be updated again to reflect the additional information. In dynamic modes, if the monitoring phase detects a change in $I_{Thresh}$, the algorithm will again stimulate at the boundary level(s) as necessary and update the color and/or audio signals before transitioning to the bracketing and bisection phases to determine the new $I_{Thresh}$.

The multi-channel threshold hunting algorithm reduces the number stimulations required to complete the bracketing and bisection steps when $I_{Thresh}$ is being found for multiple channels. The multi-channel algorithm does so by omitting stimulations for which the result is predictable from the data already acquired. When a stimulation signal is omitted, the algorithm proceeds as if the stimulation had taken place. However, instead of reporting an actual recruitment result, the reported result is inferred from previous data. This permits the algorithm to proceed to the next step immediately, without the time delay associated with a stimulation signal.

Regardless of what channel is being processed for $I_{Thresh}$, each stimulation signal elicits a response from all active channels. That is to say, every channel either recruits or does not recruit in response to a stimulation signal (again, a channel is said to have recruited if a stimulation signal evokes an EMG response deemed to be significant on that channel, such as $V_{pp}$ of approximately 100 µV). These recruitment results are recorded and saved for each channel. Later, when a different channel is processed for $I_{Thresh}$, the saved data can be accessed and, based on that data, the algorithm may omit a stimulation signal and infer whether or not the channel would recruit at the given stimulation current.

There are two reasons the algorithm may omit a stimulation signal and report previous recruitment results. A stimulation signal may be omitted if the selected stimulation current would be a repeat of a previous stimulation. By way of example only, if a stimulation current of 1 mA was applied to determine $I_{Thresh}$ for one channel, and a stimulation at 1 mA is later required to determine $I_{Thresh}$ for another channel, the algorithm may omit the stimulation and report the previous results. If the specific stimulation current required has not previously been used, a stimulation signal may still be omitted if the results are already clear from the previous data. By way of example only, if a stimulation current of 2 mA was applied to determine $I_{Thresh}$ for a previous channel and the present channel did not recruit, when a stimulation at 1 mA is later required to determine $I_{Thresh}$ for the present channel, the algorithm may infer from the previous stimulation that the present channel will not recruit at 1 mA because it did not recruit at 2 mA. The algorithm may therefore omit the stimulation and report the previous result.

Figure 38:
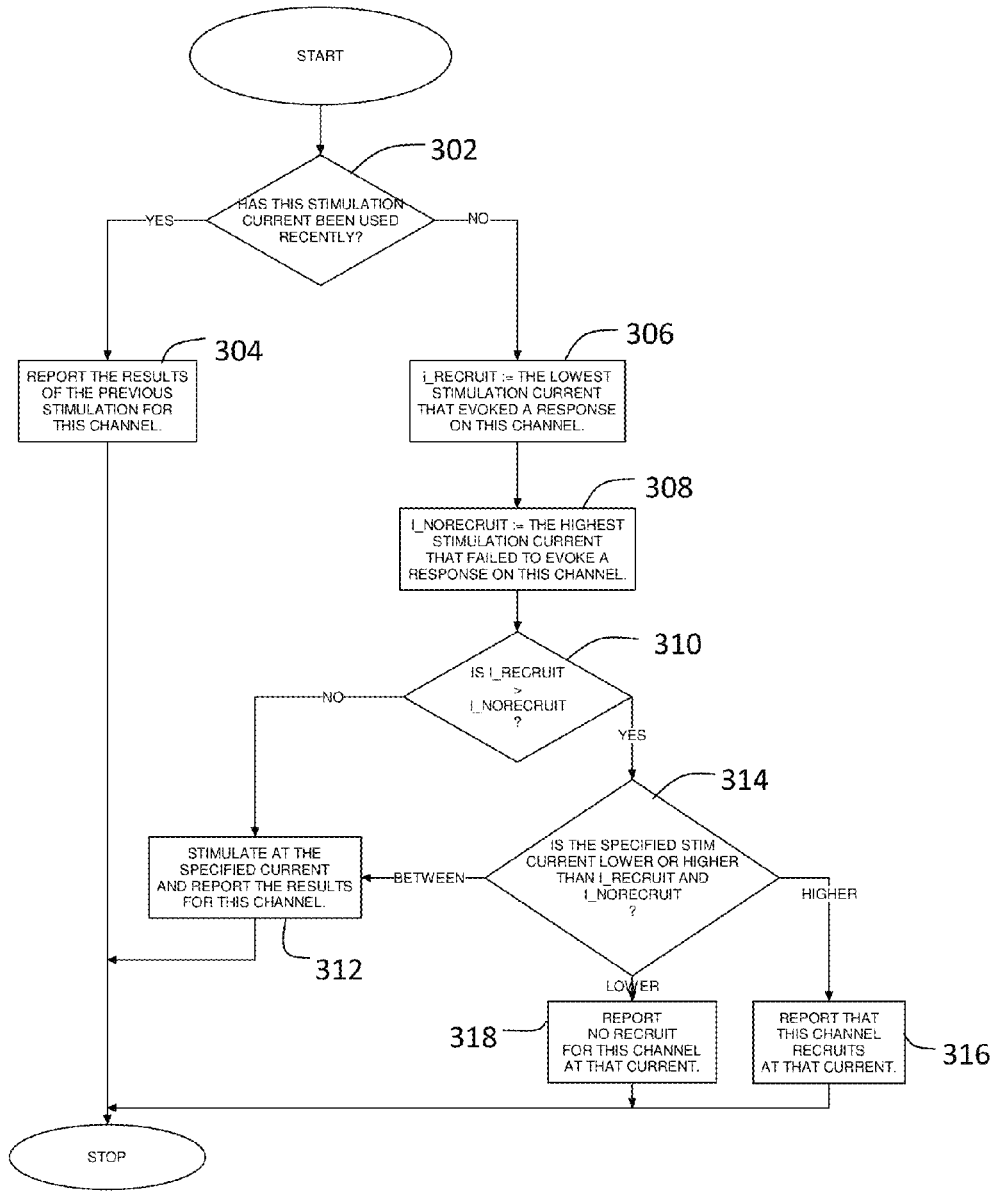
FIG. 38 is a flowchart illustrating the method by which a multi-channel hunting algorithm determines whether to perform or omit a stimulation.

FIG. 38 illustrates (in flowchart form) a method by which the multi-channel threshold hunting algorithm determines whether to stimulate, or not stimulate and simply report previous results. The algorithm first determines if the selected stimulation current has already been used (step 302). If the stimulation current has been used, the stimulation is omitted and the results of the previous stimulation are reported for the present channel (step 304). If the stimulation current has not been used, the algorithm determines $I_{recruit}$ (step 306) and $I_{norecruit}$ (step 308) for the present channel. $I_{recruit}$ is the lowest stimulation current that has recruited on the present channel. $I_{norecruit}$ is the highest stimulation current that has failed to recruit on the present channel. The algorithm next determines whether $I_{recruit}$ is greater than $I_{norecruit}$ (step 310). An $I_{recruit}$ that is not greater than $I_{norecruit}$ is an indication that changes have occurred to $I_{thresh}$ on that channel. Thus, previous results may not be reflective of the present threshold state and the algorithm will not use them to infer the response to a given stimulation current. The algorithm will stimulate at the selected current and report the results for the present channel (step 312). If $I_{recruit}$ is greater than $I_{norecruit}$, the algorithm determines whether the selected stimulation current is higher than $I_{recruit}$, lower than $I_{norecruit}$, or between $I_{recruit}$ and $I_{norecruit}$ (step 314). If the selected stimulation current is higher than $I_{recruit}$, the algorithm omits the stimulation and reports that the present channel recruits at the specified current (step 316). If the selected stimulation current is lower than $I_{norecruit}$, the algorithm infers that the present channel will not recruit at the selected current and reports that result (step 318). If the selected stimulation current falls between $I_{recruit}$ and $I_{norecruit}$, the result of the stimulation cannot be inferred and the algorithm stimulates at the selected current and reports the results for the present channel (step 312). This method may be repeated until $I_{thresh}$ has been determined for every active channel.

In the interest of clarity, FIGS. 39 A-C demonstrate use of the multi-channel threshold hunting algorithm to determine $I_{Thresh}$ on only two channels. It should be appreciated, however, that the multi-channel algorithm is not limited to finding $I_{Thresh}$ for two channels, but rather it may be used to find $I_{Thresh}$ for any number of channels, such as (for example) eight channels according to a preferred embodiment of the neurophysiology system 10. With reference to FIG. 39 A, channel 1 has an $I_{Thresh}$ to be found of 6.25 mA and channel 2 has an $I_{Thresh}$ to be found of 4.25 mA. $I_{thresh}$ for channel 1 is found first as illustrated in FIG. 39 B, using the bracketing and bisection methods discussed above. Bracketing begins at the minimum stimulation current (for the purposes of example only) of 1 mA. As this is the first channel processed and no previous recruitment results exist, no stimulations are omitted. The stimulation current is doubled with each successive stimulation until a significant EMG response is evoked at 8 mA. The initial bracket of 4-8 mA is bisected, using the bisection method described above, until the stimulation threshold, $I_{Thresh}$, is contained within a final bracket separated by the selected width or resolution (again 0.25 mA). In this example, the final bracket is 6 mA-6.25 mA. $I_{thresh}$ may be defined as any point within the final bracket or as the midpoint of the final bracket (6.125 mA in this case). In either event, $I_{Thresh}$ is selected and reported as $I_{Thresh}$ for channel 1.

Once $I_{Thresh}$ is found for channel 1, the algorithm turns to channel 2, as illustrated in FIG. 39 C. The algorithm begins to process channel 2 by determining the initial bracket, which is again 4-8 mA. All the stimulation currents required in the bracketing state were used in determining $I_{Thresh}$ for channel 1. The algorithm refers back to the saved data to determine how channel 1 responded to the previous stimulations. From the saved data, the algorithm may infer that channel 2 will not recruit at stimulation currents of 1, 2, and 4 mA, and will recruit at 8 mA. These stimulations are omitted and the inferred results are displayed. The first bisection stimulation current selected in the bisection process (6 mA in this case), was previously used and, as such, the algorithm may omit the stimulation and report that channel 2 recruits at that stimulation current. The next bisection stimulation current selected (5 mA in this case) has not been previously used and, as such, the algorithm must determine whether the result of a stimulation at 5 mA may still be inferred. In the example shown, $I_{recruit}$ and $I_{norecruit}$ are determined to be 6 mA and 4 mA, respectively. Because 5 mA falls in between $I_{recruit}$ and $I_{norecruit}$, the algorithm may not infer the result from the previous data and, as such, the stimulation may not be omitted. The algorithm then stimulates at 5 mA and reports that the channel recruits. The bracket is reduced to the lower half (making 4.50 mA the next bisection stimulation current). A stimulation current of 4.5 mA has not previously been used and, as such, the algorithm again determines $I_{recruit}$ and $I_{norecruit}$ (5 mA and 4 mA in this case). The selected stimulation current (4.5 mA) falls in between $I_{recruit}$ an $I_{norecruit}$ and, as such, the algorithm stimulates at 4.5 mA and reports the results. The bracket now stands at its final width of 0.25 mA (for the purposes of example only). $I_{thresh}$ may be defined as any point within the final bracket or as the midpoint of the final bracket (4.125 mA in this case). In either event, $I_{thresh}$ is selected and reported as $I_{Thresh}$ for channel 2.

Although the multi-channel threshold hunting algorithm is described above as processing channels in numerical order, it will be understood that the actual order in which channels are processed is immaterial. The channel processing order may be biased to yield the highest or lowest threshold first (discussed below) or an arbitrary processing order may be used. Furthermore, it will be understood that it is not necessary to complete the algorithm for one channel before beginning to process the next channel, provided that the intermediate state of the algorithm is retained for each channel. Channels are still processed one at a time. However, the algorithm may cycle between one or more channels, processing as few as one stimulation current for that channel before moving on to the next channel. By way of example only, the algorithm may stimulate at 10 mA while processing a first channel for $I_{Thresh}$. Before stimulating at 20 mA (the next stimulation current in the bracketing phase), the algorithm may cycle to any other channel and process it for the 10 mA stimulation current (omitting the stimulation if applicable). Any or all of the channels may be processed this way before returning to the first channel to apply the next stimulation. Likewise, the algorithm need not return to the first channel to stimulate at 20 mA, but instead may select a different channel to process first at the 20 mA level. In this manner, the algorithm may advance all channels essentially together and bias the order to find the lower threshold channels first or the higher threshold channels first. By way of example only, the algorithm may stimulate at one current level and process each channel in turn at that level before advancing to the next stimulation current level. The algorithm may continue in this pattern until the channel with the lowest $I_{Thresh}$ is bracketed. The algorithm may then process that channel exclusively until $I_{Thresh}$ is determined, and then return to processing the other channels one stimulation current level at a time until the channel with the next lowest $I_{Thresh}$ is bracketed. This process may be repeated until $I_{Thresh}$ is determined for each channel in order of lowest to highest $I_{Thresh}$. If $I_{Thresh}$ for more than one channel falls within the same bracket, the bracket may be bisected, processing each channel within that bracket in turn until it becomes clear which one has the lowest $I_{Thresh}$. If it becomes more advantageous to determine the highest $I_{Thresh}$ first, the algorithm may continue in the bracketing state until the bracket is found for every channel and then bisect each channel in descending order.

Figure 40A:
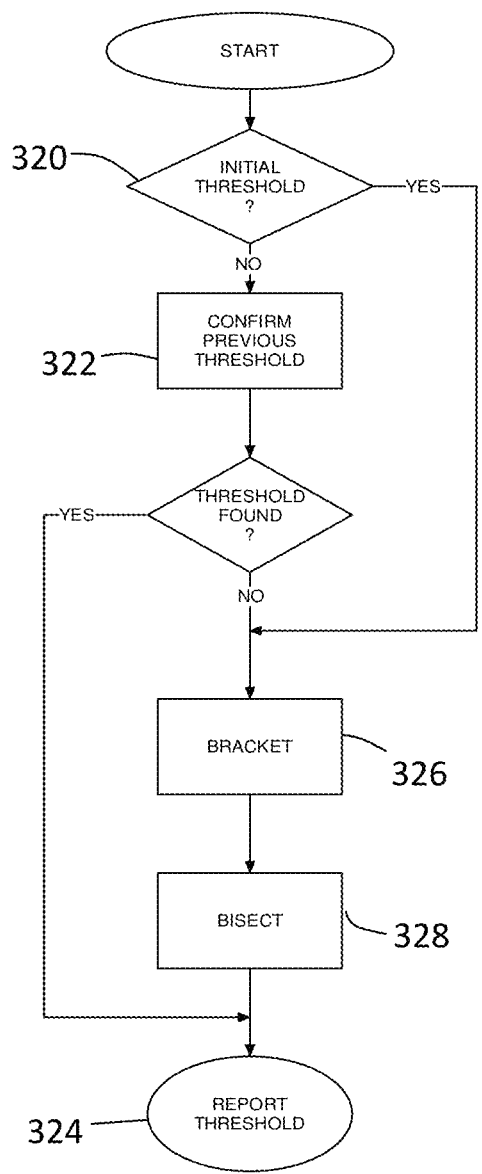
FIG. 40A is a flowchart illustrating the sequence employed by the algorithm to determine and monitor $I_{Thresh}$.
Figure 40B:
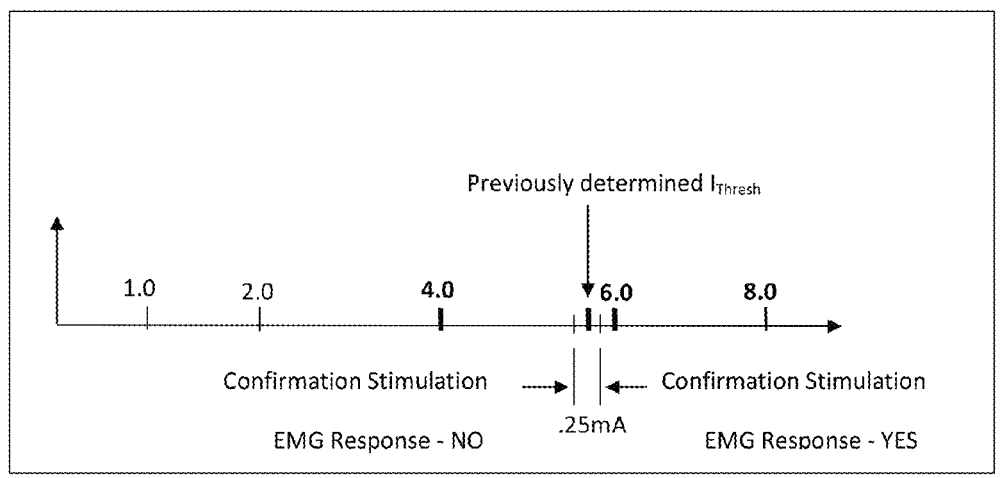
FIG. 40B is a graph illustrating the confirmation step employed by the algorithm to determine whether $I_{Thresh}$ has changed from a previous determination.

FIGS. 40 A-B illustrates a further feature of the threshold hunting algorithm of the present invention, which advantageously provides the ability to further reduce the number of stimulations required to find $I_{Thresh}$ when an $I_{Thresh}$ value has previously been determined for a specific channel. In the event that a previous $I_{Thresh}$ determination exists for a specific channel, the algorithm may begin by merely confirming the previous $I_{Thresh}$ rather than beginning anew with the bracketing and bisection methods. The algorithm first determines whether it is conducting the initial threshold determination for the channel or whether there is a previous $I_{Thresh}$ determination (step 320). If it is not the initial determination, the algorithm confirms the previous determination (step 322) as described below. If the previous threshold is confirmed, the algorithm reports that value as the present $I_{Thresh}$ (step 324). If it is the initial $I_{Thresh}$ determination, or if the previous threshold cannot be confirmed, then the algorithm performs the bracketing function (step 326) and bisection function (step 328) to determine $I_{Thresh}$ and then reports the value (step 324).

Although the hunting algorithm is discussed herein in terms of finding $I_{Thresh}$ (the lowest stimulation current that evokes a predetermined EMG response), it is contemplated that alternative stimulation thresholds may be useful in assessing the health of the spinal cord or nerve monitoring functions and may be determined by the hunting algorithm. By way of example only, the hunting algorithm may be employed by the system 10 to determine a stimulation voltage threshold, $V_{Stim(Thresh)}$. This is the lowest stimulation voltage (as opposed to the lowest stimulation current) necessary to evoke a significant EMG response, $V_{Thresh}$. Bracketing, bisection and monitoring states are conducted as described above for each active channel, with brackets based on voltage being substituted for the current based brackets previously described. Moreover, although described above within the context of MEP monitoring, it will be appreciated that the algorithms described herein may also be used for determining the stimulation threshold (current or voltage) for any other EMG related functions, including but not limited to pedicle integrity (screw test), nerve detection, and nerve root retraction.

While this invention has been described in terms of a best mode for achieving this invention's objectives, it will be appreciated by those skilled in the art that variations may be accomplished in view of these teachings without deviating from the spirit or scope of the present invention. For example, the present invention may be implemented using any combination of computer programming software, firmware or hardware. As a preparatory step to practicing the invention or constructing an apparatus according to the invention, the computer programming code (whether software or firmware) according to the invention will typically be stored in one or more machine readable storage mediums such as fixed (hard) drives, diskettes, optical disks, magnetic tape, semiconductor memories such as ROMs, PROMs, etc., thereby making an article of manufacture in accordance with the invention. The article of manufacture containing the computer programming code is used by either executing the code directly from the storage device, by copying the code from the storage device into another storage device such as a hard disk, RAM, etc. or by transmitting the code on a network for remote execution. As can be envisioned by one of skill in the art, many different combinations of the above may be used and accordingly the present invention is not limited by the specified scope.

What is claimed is:

1. A system for detecting and monitoring nerves during surgery, comprising:
   at least one electrode configured to detect activity from a muscle innervated by a nerve;
   a surgical accessory configured to transmit stimulation signals; and
   a control unit communicatively linked to said at least one EMG electrode and said accessory, the control unit being configured to perform free-run EMG monitoring by monitoring muscle activity detected by the at least one electrode, the control unit also being configured to perform stimulated EMG monitoring by directing delivery of stimulation signals from the surgical accessory, receiving neuromuscular response data from the at least one electrode, and determining a relationship between the stimulation signal and associated neuromuscular response activity,
   wherein the control unit further includes a selectable sensitivity setting for which a voltage sensitivity setting is selected, the selected sensitivity setting representing a minimum amplitude detected by the electrode recognized by the control unit as an event, and wherein the control unit applies a pre-determined differential sensitivity setting that differs from the selected sensitivity setting to activity associated with free-run EMG monitoring and activity associated with stimulated EMG monitoring.

2. The system of claim 1, wherein said neuromuscular responses comprise responses from at least one of static pedicle screw testing, dynamic pedicle screw testing, nerve proximity detection, nerve pathway assessments, manual motor evoked potentials, and automatic motor evoked potentials.

3. The system of claim 1, wherein said selectable sensitivity setting input is selectable through user intervention.

4. The system of claim 3, wherein said selectable sensitivity setting input is selectable based on at least one of background noise and background neurophysiologic activity.

5. The system of claim 1, wherein said sensitivity setting differential is achieved using a fixed increase differential.

6. The system of claim 1, wherein said differential sensitivity setting is achieved using percent increase differential.

7. The system of claim 1, wherein said sensitivity setting differential is achieved using a fixed offset differential.

8. The system of claim 1, wherein said sensitivity setting differential is achieved using a percent offset differential.

* * * * *